US008603784B2

(12) United States Patent
Brown et al.

(10) Patent No.: US 8,603,784 B2
(45) Date of Patent: Dec. 10, 2013

(54) INFECTIOUS CLONE OF HUMAN PARVOVIRUS B19 AND METHODS

(75) Inventors: Kevin Edward Brown, Kensington, MD (US); Ning Zhi, Rockville, MD (US); Peter Tijssen, Pointe-Claire (CA); Zoltan Zadori, Montreal (CA)

(73) Assignees: The United States of America, as represented by the Secretary, Department of Health and Human Services, Washington, DC (US); Institut National de Rechesche Scientifique, Quebec (CA)

( * ) Notice: Subject to any disclaimer, the term of this patent is extended or adjusted under 35 U.S.C. 154(b) by 516 days.

(21) Appl. No.: 12/569,848

(22) Filed: Sep. 29, 2009

(65) Prior Publication Data

US 2010/0136514 A1 Jun. 3, 2010

Related U.S. Application Data

(62) Division of application No. 10/887,770, filed on Jul. 9, 2004, now Pat. No. 7,598,071.

(51) Int. Cl.

| | |
|---|---|
| ***C12N 15/35*** | (2006.01) |
| *C12N 15/79* | (2006.01) |

(52) U.S. Cl.

USPC .................... 435/91.33; 435/320.1; 435/325; 435/235.1

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 6,632,670 | B1 | 10/2003 | Wadsworth et al. |
| 6,669,935 | B1 | 12/2003 | Oldfield et al. |
| 6,677,155 | B1 | 1/2004 | Sena-Esteves et al. |
| 6,743,772 | B1 | 6/2004 | Broliden et al. |
| 2004/0014220 | A1 | 1/2004 | Siebenkotten et al. |

OTHER PUBLICATIONS

Deng et al. International Journal of Microbiology, 1998, vol. 45, No. 3, pp. 173-184.*

Deiss et al. Virology 1990, vol. 175: pp. 247-254.*

Srivastava et al. PNAS 1989, vol. 86, pp. 8078-8082.*

Filippone at al., "VP1 u phospholipase activity is critical for infectivity of full-length parvovirus B19 genomic clones," Virology, vol. 374 No. 2, pp. 444-452 (May 2008).

Bowie at al., "Deciphering the Message in Protein Sequences: Tolerance to Amino Acid Substitutions," Science, vol. 247, No. 4948, pp. 1306-1310 (Mar. 1990).

GenBank Accession No. AY386330 dated Nov. 12, 2004.

GenBank Accession No. M13178 dated May 17, 1995.

GenBank Accession No. AF162273 dated Aug. 2, 1999.

GenBank Accession No. M24682 dated Aug. 3, 1993.

Berns, "Parvoviridae and Their Replication," Virology, Second Edition. Fields at al., Raven Press Ltd., NY, pp. 1743-1763 (1990).

Brodeur at al., "Mouse-Human Myeloma Partners for the Production of Heterohybridomas," Monoclonal Antibody Production Techniques and Applications, Marcel Dekker, Inc., NY, pp. 51-63 (1987).

Brown at al., "Molecular, cellular and clinical aspects of Parvovirus B19 infection," Crit. Rev. Oncol./Hematol., vol. 16, pp. 1-31 (1994).

Brown at al., "In vitro propagation of parvovirus B19 in primary foetal liver culture," J. Gen. Vir., vol. 72, No. 3, pp. 741-745 (1991).

Brown et al., "Erythrocyte P antigen: cellular receptor for B19 parvovirus," Science, vol. 262, pp. 114-117 (1993).

Brown et al., "Resistance to Parvovirus B19 Infection Due to Lack of Virus Receptor," N. Engl. J. Med., vol. 330, pp. 1192-1196 (1994).

Cotmore et al., "Characterisation and molecular cloning ofa human parvovirus genome," Science, vol. 226, pp. 1161-1165 (1986).

Deiss et al., "Cloning of the Human Parvovirus B19 Genome and Structural Analysis of Its Palindromic Termini," Virology, vol. 175, No. 1, pp. 247-254 (1990).

Dorsch et al., "The VP1 Unique Region of Parvovirus B19 and Its Constituent Phospholipase A2-Like Activity," Journal of Virology, vol. 76, No. 4, pp. 2014-2018 (2002).

Erdman et al., "Genetic diversity of human parvovirus B19: sequence analysis of the VP1/VP2 gene from multiple isolates", J. Gen. Virol., vol. 77, No. 11, pp. 2767-2774 (1996).

Evan et al., "Isolation of Monoclonal Antibodies Specific for Human *c-myc* Proto-Oncogene Product", Molecular and Cellular Biology, vol. 5, No. 12, pp. 3610-3616 (1985).

Fan et al., "The Small 11-kDa Protein from B19 Parvovirus Binds Growth Factor Receptor-Binding Protein 2 in Vitro in a Src Homology 3 Domain/Ligand-Dependent Manner", Virology, vol. 291, pp. 285-291 (2001).

Field et al., "Purification of a RAS-Responsive Adenylyl Cyclase Complex from *Saccharomyces cerevisiae* by Use of an Epitope Addition Method", Mol. Cell. Biol., vol. 8, No. 5, pp. 2159-2165 (1988).

Goding, "Production of Monoclonal Antibodies", Monoclonal Antibodies: Principles and Practice, Academic Press, pp. 59-103 (1986).

Harris, "Therapeutic Monoclonals", Biochem. Soc. Transactions, vol. 23, pp. 1035-1038 (1995).

Heegaard et al., "Human Parvovirus B19", Clinical Microbiology Reviews, vol. 15, No. 3, pp. 485-505 (2002).

Hemauer et al., "Sequence variability among different parvovirus B19 isolates", J. Gen. Virol., vol. 77, pp. 1781-1785 (1996).

Hopp et al., "A Short Polypeptide Marker Sequence Useful for Recombinant Protein Identification and Purification", BioTechnology, vol. 6, pp. 1204-1210 (1988).

(Continued)

*Primary Examiner* — Bao Li

(74) *Attorney, Agent, or Firm* — Edwards Wildman Palmer LLP; Peter F. Corless

(57) ABSTRACT

The invention relates to infectious clones of parvovirus B19, methods of cloning infectious B19 clones, and methods of cloning viral genomes that have secondary DNA structures that are unstable in bacterial cells. A B19 infectious clone and methods of producing B19 infectious clones are useful for producing infectious virus. Infectious virus is useful for identifying and developing therapeutically effective compositions for treatment and/or prevention of human parvovirus B19 infections.

10 Claims, 19 Drawing Sheets

(56) References Cited

OTHER PUBLICATIONS

Hurle et al., "Protein engineering techniques for antibody humanization", Curr. Op. Biotech, vol. 5, No. 4, pp. 428-433 (1994).
Jones et al., "Replacing the complementarity-determining regions in a human antibody with those from a mouse", Nature, vol. 321, pp. 522-525 (1986).
Kohler et al., "Continuous cultures of fused cells secreting antibody of predefined specifity", Nature, vol. 256, pp. 495-497 (1975).
Komatsu et al., "Establishment and Characterization of an Erythropoietin-Dependent Subline, UT-7/Epo, Derived From Human Leukemia Cell Line, UT-7", Blood, vol. 82, No. 2, pp. 456-464 (1993).
Kozbor et al., "A Human Hybrid Myeloma for Production of Human Monoclonal Antibodies", J. Immunol., vol. 133, No. 6, pp. 3001-3005 (1984).
Liu et al., "A block in full-length transcript maturation in cells nonpermissive for B19 parvovirus", Journal of Virology, vol. 66, No. 8, pp. 4686-4692 (1992).
Lutz-Freyermuth et al., "Quantitative determination that one of two potential RNA-binding domains of the A protein component of the U1 small nuclear ribonucleoprotein complex binds with high affinity to stem-loop II of U1 RNA", Proc. Natl. Acad. Sci. USA, vol. 87, pp. 6393-6397 (1990).
Martin et al., "GAP Domains Responsible for Ras p21-Dependent Inhibition of Muscarinic Atrial K+ Channel Currents", Science, vol. 255, pp. 192-194 (1992).
Miyagawa et al., "Infection of the erythroid cell line, KU812Ep6 with human parvovirus B19", J. Gen. Virol., vol. 83, pp. 45-54 (1999).
Mori et al., "Structure and mapping of the DNA of human parvovirus B19 ", J. Gen. Virol., vol. 68, pp. 2797-2806 (1987).
Munshi et al., "Successful Replication of Parvovirus B19 in the Human Megakaryocytic Leukemia Cell Line MB-02", J. or Virol., vol. 67, No. 1, pp. 562-566 (1993).
Ozawa et al., "Replication of the B19 Parvovirus in Human Bone Marrow Cell Cultures", Science, vol. 233, pp. 883-886 (1986).
Paborsky et al., "Mammalian cell transient expression of tissue factor for the production of antigen", Protein Engineering, vol. 3, No. 6, pp. 547-553 (1990).
Ponnazhagan et al., "Recombinant Human parvovirus B19 Vectors: Erythroid Cell-Specific Delivery and Expression of Transduced Genes", Journal of Virology, vol. 72, No. 6, pp. 5224-5230 (1998).
Presta, "Antibody Engineering", Curr. Op. Struct. Biol., vol. 2, pp. 593-596 (1992).
Riechmann et al., "Reshaping human antibodies for therapy", Nature, vol. 332, pp. 323-329 (1988).
Shade et al., "Nucleotide sequence and genome organization of human parvovirus B19 isolated from the serum of a child during aplastic crisis", J. Virol., vol. 58, pp. 921-936 (1986).
Shimomura et al., "First continuous propagation of B19 parvovirus in a cell line", Blood, vol. 79, pp. 18-24 (1992).
Skinner et al., "Use of the Glu-Glu-Phe C-terminal Epitope for Rapid Purification of the Catalytic Domain of Normal and Mutant *ras* GTPase-activating Proteins", J. Biol. Chem., vol. 266, No. 22, pp. 14163-14166 (1991).
Srivastava et al., "Constuction of a recombinant human parvovirus B19: Adeno-associated virus 2 (AAV) DNA inverted terminal repeats are functional in an AAV-B19 hybrid virus", Proc. Natl. Acad. Sci. USA, vol. 86, pp. 8078-8082 (1989).
St. Amand et al., "A Novel Protein Encoded by Small NRAs of Parvovirus B19", Virology, vol. 195, No. 2, pp. 448-455 (1993).
St. Amand et al., "Identification and Characterization of a Family of 11-kDa Proteins Encoded by the Human Parvovirus B19", Virology, vol. 192, pp. 121-131 (1993).
Summers et al., "Characterization of the genome of the agent of erythrocyte aplasia permits its classification as a human parvovirus", J. Gen. Virology, vol. 64, pp. 2527-2532 (1983).
Vaswani et al., "Humanized antibodies as potential therapeutic drugs", Ann. Allergy, Asthma & immunol., vol. 81, No. 2, pp. 105-115 (1998).
Yaegashi et al., "Propagation of human parvovirus B19 in primary culture of erythroid lineage cells derived from liver", J. Virology, vol. 63, No. 6, pp. 2422-2426 (1989).
Yoshimoto et al., "A second neutralizing epitope of B19 parvovirus implicates the spike region in the immune response", J. Virology, vol. 65, No. 12, pp. 7056-7060 (1991).
Zhi et al., "Construction and sequencing of an infectious clone of the human parvovirus B19", 22nd Annual Meeting American Society for Virology, available online Apr. 13, 2003.
Zhi et al., "Construction and sequencing of an infectious clone of the huma parvovirus B19", Virology, vol. 318, pp. 142-152 (2004).
Morita et al., "Human parvovirus B19 induces cell cycle arrest at G(2) phase with accumulation of Mitotic cyclins", Journal of Virology, vol. 75 No. 16, pp. 7555-7563 (2001).
Samulski et al., "A recombinant plasmid from which an infectious adeno-associated virus genome can be excised in vitro and its use to study viral replication", Journal of Virology, vol. 61, No. 10, pp. 3096-3101 (1987).
GenBank M29711 "Parvovirus B19 inverted terminal repeat, 3' end" (1993).

* cited by examiner

FIG. 2B

```
                10        20        30        40        50        60        70        80        90       100
1   --AAATCAGATGCCGCCGGTCGCCGCCGGTAGGCGGGACTTCCGGTACAAGATGCCGGACAATTACGTCATTTCCTGTGACGTCATTTCCTGTGACGTCA J35-flip
1   --AAATCAGATGCCGCCGGTCGCCGCCGGTAGGCGGGACTTCCGGTACAAGATGCCGGACAATTACGTCATTTCCTGTGACGTCATTTCCTGTGACGTCA J35-flop
1   -1AAATCAGATGCCGCCGGTCGCCGCCGGTAGGCGGGACTTCCGGTACAAGATGCCGGACAATTACGTCATTTCCTGTGACGTCATTTCCTGTGACGTCA Doiss-flip
1   -1AAATCAGATGCCGCCGGTCGCCGCCGGTAGGCGGGACTTCCGGTACAAGATGCCGGACAATTACGTCATTTCCTGTGACGTCATTTCCTGTGACGTCA Doiss-flop
1   -1AAATCAGATGCCGCCGGTCGCCGCCGGTAGGCGGGACTTCCGGTACAAGATGCCGGACAATTACGTCATTTCCTGTGACGTCATTTCCTGTGACGTCA HV-flop

               110       120       130       140       150       160       170       180       190       200
99  CTTCCGGTGGGCGGACTTCCGGAATTAGGGTTGGCTCTGGGCCAGCTTGCTTGGGGTTCCCTTGACACTAAGA-CAAGCGGCGCGCCGCTTGATCTTAG J35-flip
99  CTTCCGGTGGGCGGACTTCCGGAATTAGGGTTGGCTCTGGGCCAGC--GCTTGGGGTTGACGTGGCACTAAGA1CAAGCGGCGCGCCGCTTG-TCTTAG J35-flop
101 CTTCCGGTGGGCGGACTTCCGGAATTAGGGTTGGCTCTGGGCCAGC--GCTTGGGGTTGCCTTGACACTAAGA-CAAGCGGCGCGCCGCTTGATCTTAG Doiss-flip
101 CTTCCGGTGGGCGGACTTCCGGAATTAGGGTTGGCTCTGGGCCAGCTTGCTTGGGGTTGACGTGGCACTAAGA1CAAGCGGCGCGCCGCTTG-TCTTAG Doiss-flop
101 CTTCCGGTGGGCGGACTTCCGGAATTAGGGTTGGCTCTGGGCCAGCTTGCTTGGGGTTGCCTTGACACTAAGA-CAAGCGGCGCGCCGCTTG-TCTTAG HV-flop
```

FIG. 2B (continued)

```
             210       220       230       240       250       260       270       280       290       300
198 TGGCACGTCAACCCCAAGC--GCTGGCCCAGAGCCAACCCTAATTCCGGAAGTCCCGCCCACCCGAAGTGACGTCACAGGAAATGACGTCACAGGAAATG j35-flip
196 TGTCAAGACAACCCCAAGCAAGCTGGCCCAGAGCCAACCCTAATTCCGGAAGTCCCGCCCACCCGAAGTGACGTCACAGGAAATGACGTCACAGGAAATG j35-flop
198 TGGCACGTCAACCCCAAGCAAGCTGGCCCAGAGCCAACCCTAATTCCGGAAGTCCCGCCCACCCGAAGTGACGTCACAGGAAATGACGTCACAGGAAATG Doiss-flip
200 TGTCAAGACAACCCCAAGC--GCTGGCCCAGAGCCAACCCTAATTCCGGAAGTCCCGCCCACCCGAAGTGACGTCACAGGAAATGACGTCACAGGAAATG Doiss-flop
199 TGGCACGTCAACCCCAAGC--GCTGGCCCAGAGCCAACCCTAATTCCGGAAGTCCCGCCCACCCGAAGTGACGTCACAGGAAATGACGTCACAGGAAATG HV-flip

             310       320       330       340       350       360
296 ACGTAATTGTCCGCCATCTTGTACCGGAACTCCCGCCTACCGGCGGCGACCGGCGGCATCTGATTTGG j35-flip
296 ACGTAATTGTCCGCCATCTTGTACCGGAACTCCCGCCTACCGGCGGCGACCGGCGGCATCTGATTTGG j35-flop
298 ACGTAATTGTCCGCCATCTTGTACCGGAACTCCCGCCTACCGGCGGCGACCGGCGGCATCTGATTTGG Doiss-flip
298 ACGTAATTGTCCGCCATCTTGTACCGGAACTCCCGCCTACCGGCGGCGACCGGCGGCATCTGATTTGG Doiss-flop
297 ACGTAATTGTCCGCCATCTTGTACCGGAACTCCCGCCTACCGGCGGCGACCGGCGGCATCTGATTT   HV-flop
```

INFECTIOUS CLONE OF HUMAN PARVOVIRUS B19 AND METHODS

CROSS-REFERENCE TO RELATED APPLICATIONS

This application is a divisional of U.S. patent application Ser. No. 10/887,770, filed Jul. 9, 2004, now U.S. Pat. No. 7,598,071, the contents of which is incorporated herein by reference in its entirety.

STATEMENT OF RIGHTS TO INVENTIONS MADE UNDER FEDERALLY SPONSORED RESEARCH AND DEVELOPMENT

Part of the work performed during the development of this invention utilized United States government funds under the Division of Intramural Research, NHLBI.NIH.

BACKGROUND OF THE INVENTION

Human parvovirus B19 is the only member of the Parvoviridae family known to cause diseases in humans. Parvovirus B19 infection causes fifth disease in children, polyarthropathy syndromes in adults, transient aplastic crisis in patients with underlying chronic hemolytic anemia, and chronic anemia due to persistent infection in immunocompromised patients. Hydrops fetalis and fetal death have been reported after maternal infection with parvovirus B19 during pregnancy (Brown et al., 1994, Crit. Rev. Oncol./Hematol. 16:1-13).

Parvovirus B19 exhibits a selective tropism for erythroid progenitor cells. The virus can be cultured in erythroid progenitor cells from bone marrow, fetal liver cells, and cell lines such as UT7/Epo or KU812Ep6. (Ozawa et al., 1986, Science 233:883-886; Brown et al., 1991, J. Gen. Vir. 72:741-745; Komatsu et al., 1993, Blood 82:456-464; Shimomura et al., 1992, Blood 79:18-24; Miyagawa et al., 1999, J. Virol. Methods 83:45-54). Although the virus can be cultured in these cells very little virus is produced. The selective tropism of the virus is mediated in part by neutral glycolipid globoside (blood group P antigen), which is present on cells of the erythroid lineage (Brown et al., 1993, *Science,* 262:114-117). The presence of globoside on the surface of a cell is a determinant of viral tropism. Parvovirus B19 has a cytotoxic effect on erythroid progenitor cells in bone barrow and causes interruption of erythrocyte production. Human bone marrow cells that lack globoside on the cell surface are resistant to parvovirus B19 infection (Brown et al., 1994, *N. Engl. J. Med.,* 33:1192-1196).

The ends of the parvovirus B19 genome have long inverted repeats (ITR), which are imperfect palindromes that form double-stranded hairpins. The role of the ITRs in the parvovirus B19 viral life cycle is unknown due to the inability to produce an infectious clone containing complete ITR sequences. In other parvoviruses, ITRs play an important role in the viral life cycle: they serve as primers for the synthesis of the complementary strand of viral DNA and are essential for the replication, transcription, and packaging of virus DNA (Berns, K (1990) in Virology, eds. Fields et al. Raven Press Ltd, NY, pp 1743-1763). Previous attempts to produce an infectious clone of parvovirus B19 were unsuccessful due to deletions in the ITR sequences and the instability of the ITRs in bacterial cells (Deiss et al., 1990, Virology 175:247-254; Shade et al., 1986, J. Virol. 58:921-936). Methods of consistently producing infectious B19 parvovirus in cell culture are not known.

Thus, there remains a need to develop an infectious clone of parvovirus B19. A B19 infectious clone and methods of producing B19 infectious clones can be useful for producing infectious virus. Infectious virus is useful for identifying and developing therapeutically effective compositions for treatment and/or prevention of human parvovirus B19 infections, such as for example, antibodies, attenuated vaccines, and chimeric viral capsid proteins comprising antigenic epitopes.

SUMMARY OF THE INVENTION

One aspect of the invention is directed to methods of cloning a parvovirus B19 viral genome. Clones of viral genomes produced by the methods of the invention are useful for consistently producing infectious virus. Infectious virus is useful for identifying and developing therapeutically effective compositions for treatment and/or prevention of human parvovirus B19 infections, such as for example, antibodies, attenuated vaccines, and chimeric viral capsid proteins comprising antigenic epitopes.

The methods of cloning a parvovirus B19 viral genome generally employ introducing a vector comprising all or a portion of a parvovirus B19 genome into a prokaryotic cell that is deficient in at least one recombinase enzyme; incubating the cells at about 25° C. to 35° C.; and recovering the vector from the prokaryotic cells. An inverted terminal repeat (ITR) may be at the 5' end or 3' end or both of the viral genome. In an embodiment, the ITR comprises a nucleic acid sequence of SEQ ID NO:1 or SEQ ID NO:2. In addition to at least one ITR, the viral genome may comprise a nucleic acid sequence encoding at least one or all of VP2, nonstructural protein (NS), or 11-kDa protein. The bacterial cell may be recA1, endA, recB, and/or recJ deficient. In an embodiment, the bacterial cell comprises a genotype of e14-(McrA-)Δ (mcrCB-hsdSMR-mrr)171 endA1 supE44 thi-1 gyrA96 relA1 lac recB recJ sbcC umuC::Tn5 (Kanr) uvrC [F' proAB lacIqZ.M15 Tn10 (Tetr)]. Vectors that are useful in the methods of the invention include pBR322, p ProExHTb, pUc19 and pBluescript SK.

In some embodiments, the full length B19 genome is cloned by cloning at least two portions of the viral genome into separate vectors and recombining the two portions into a single vector. Preferably, two portions of the viral genome comprise an ITR at the end of the portion. The portions of the viral genome can be obtained by digesting the genome with a restriction enzyme that cuts the genome at a location between the ITRs. Preferably the restriction enzyme cuts the genome at a location at least about 800 nucleotides from the ITR. The portions may be cut and religated to reduce the vector size and eliminate undesired restriction sites. For example, the B19 genome may be digested with BamHI. The two fragments (right end genome fragment and left end genome fragment) generated by BamHI digestion are ligated into separate vectors and the full-length genome is generated by recombining the right end genome fragment and left end genome fragment into a single vector. In an embodiment, the full length genome comprises a nucleic acid sequence of SEQ ID NO:5.

The methods of producing or identifying an infectious clone or infectious virus of parvovirus B19 generally employ introducing a vector comprising all or a portion of a viral genome of parvovirus B19 into a population of cells, wherein the vector is present in at least about 15% of the cells; and incubating the cells under conditions to allow for viral replication. Preferably, the cells are eukaryotic cells, more preferably permissive cells such as for example erythroid progenitor cells, fetal liver cells, UT7/EPO cells, UT7/EPO-S1 cells, or KU812Ep6 cells. In some embodiments, the cells are cultured in vitro. Optionally, viral replication can be detected in the cells.

The vector may be introduced into the cells using standard transfection techniques known in the art. In an embodiment, the cells are transfected by electroporation or electrical nuclear transport. The viral genome preferably comprises an ITR sequence having a nucleic acid sequence of SEQ ID NO:1 or SEQ ID NO:2 and a nucleic acid sequence encoding one or more of 11-kDa protein, NS protein, VP1, VP2, or putative protein X. Preferably the ITRs are located at the 5' end or 3' end of the genome. In an embodiment, the infectious clone comprises a polynucleotide nucleic acid sequence of SEQ ID NO:5. Reproduction of the infectious clones produced by the methods of the invention can be detected by contacting permissive cells with supernatant from the population of cells and analyzing the contacted cells for spliced capsid transcripts or capsid proteins.

Another aspect of the invention is directed to isolated infectious parvovirus B19 clones. The clones may be produced by the methods of the invention. Infectious B19 clones are useful in diagnostic assays, identifying and developing therapeutically effective compositions for treatment and/or prevention of human parvovirus B19 infections, such as for example, antibodies, attenuated vaccines, and chimeric viral capsid proteins comprising antigenic epitopes. Preferably the clones comprise all or a portion of a parvovirus B19 genome and a replicable vector. The genome may comprise ITRs located at the 5' end and 3' end of the genome and a nucleic acid sequence encoding one or more of VP1, VP2, NS, 11-kDa protein, 7.5-kDa protein, or putative protein X. Preferably the viral genome comprises a polynucleotide having at least 90% nucleic acid sequence identity to SEQ ID NO:5 or SEQ ID NO:24. In an embodiment, the viral genome comprises a nucleotide sequence of SEQ ID NO:5.

The invention also encompasses using the infectious parvovirus B19 clone of the invention and/or host cells comprising the clone as immunogenic compositions to prepare vaccine components and/or to develop antibodies that can be used in diagnostic assays or to inhibit or antagonize B19 infection of cells. Host cell cultures comprising the parvovirus B19 clone can be heat inactivated and used as an immunogen. Passaging of an infectious clone in vitro can provide an attenuated strain of parvovirus B19 useful in vaccine compositions.

BRIEF DESCRIPTION OF THE DRAWINGS

FIG. 2B shows a comparison of nucleic acid sequences encoding the flip and flop forms of ITRs in B19 isolate J35 (SEQ ID NOS: 1 and 2), the B19 isolate reported by Deiss et al., 1990, *Virology,* 175:247-254 (SEQ ID NOS:3 and 4), and the flop form in B19-Hv (SEQ ID NO:37). Aligned positions are boxed in black. The numbering indicates the positions of nucleotides in the genomes of the respective B19 isolates.

FIG. 14 discloses SEQ ID NOS 39 and 40, respectively, in order of appearance.

DETAILED DESCRIPTION OF THE INVENTION

I. Definitions

Figure 1:
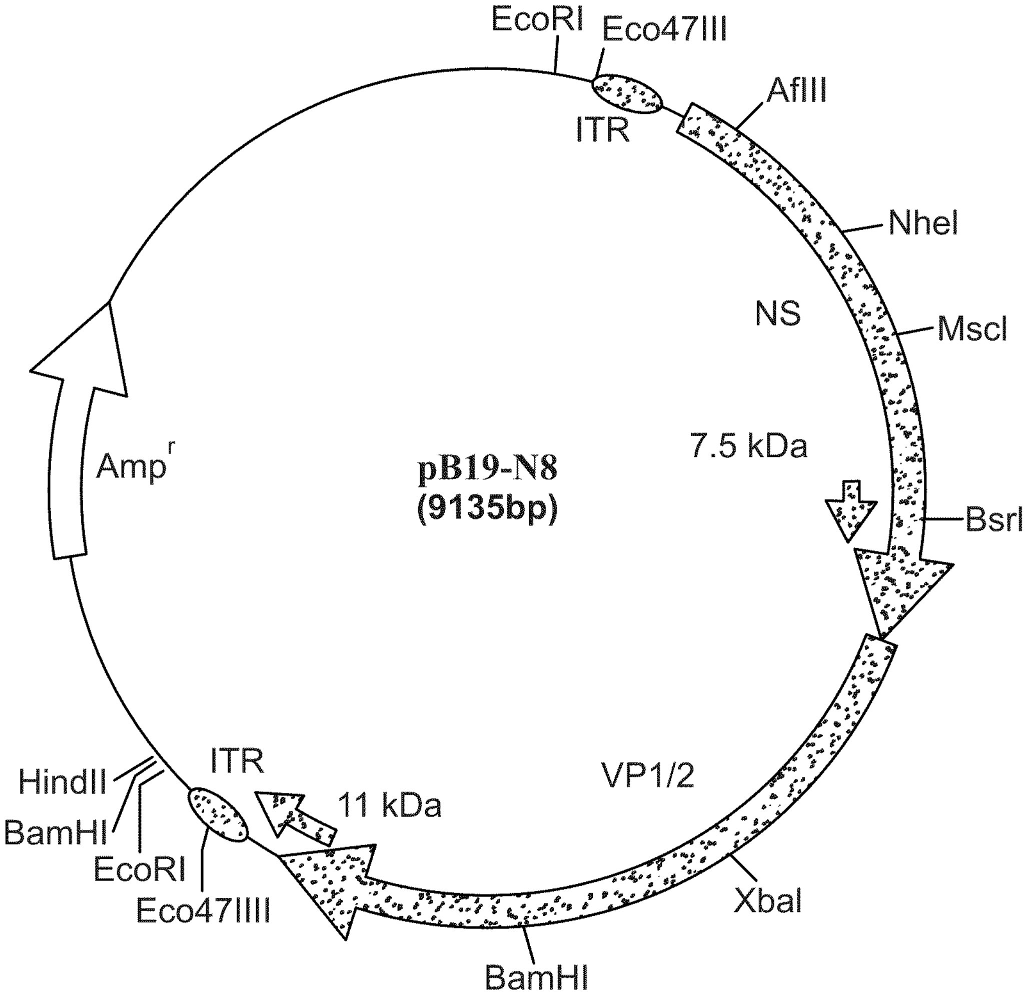
FIG. 1 shows a map of recombinant plasmid pB19-N8, which contains an insert comprising 4844 nucleotides of the B19 genome. The arrows indicate genes. Shaded arrows indicate genes in the B19 genome. The shaded circles at the 5' and 3' ends of the B19 genome indicate the ITR sequences.

The term "antibody" is used in the broadest sense and specifically includes, for example, single anti-parvovirus B19 monoclonal antibodies, anti-parvovirus B19 antibody compositions with polyepitopic specificity, single chain anti-parvovirus B19 antibodies, and fragments of anti-parvovirus B19 antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (Zapata et al., 1995, *Protein Eng.,* 8:1057-1062); single-chain antibody molecules; and multispecific antibodies formed from antibody fragments.

The term "binds specifically" refers to an antibody that binds parvovirus B19 and does not substantially bind other parvoviruses. In some embodiments, the antibody specifically binds a first B19 isolate and does not bind a second B19 isolate. For example, an antibody may specifically bind B19-Au and not bind B19-HV.

"Carriers" as used herein include pharmaceutically acceptable carriers, excipients, or stabilizers, which are nontoxic to the cell or mammal being exposed thereto at the dosages and concentrations, employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "parvovirus B19", "B19", "B19 virus", "B19 clone", or "B19 isolate" means an isolate, clone or variant B19 viral genome of parvovirus B19 of the family Parvoviridae including genotypes 1, 2, and 3. A naturally occurring isolate of parvovirus B19 of the invention has at least 90% nucleic acid identity to human parvovirus B19-Au (GenBank accession number M13178; SEQ ID NO:24), which lacks intact ITRs at both 5' and 3' ends of the genome (Shade et al., 1986, *J. Virol.,* 58:921-936). B19 has a non-enveloped, icosahedral capsid packaging a single-stranded DNA genome of approximately 5600 nucleotides. Transcription of the B19 genome is controlled by the single promoter p6 located at map unit 6, which regulates the synthesis of viral proteins including, but not limited to, nonstructural protein (NS), capsid proteins VP1 and VP2, 11-kDa protein, 7.5-kDa protein, and putative protein X. B19 viral DNA can be isolated from infected humans or cells or can be prepared as described herein. An embodiment of an isolate of parvovirus B19 has a nucleotide sequence of SEQ ID NO:5 (Table 1). In some embodiments, the B19 genome cloned into the vector may have from 1 to about 5 nucleotides deleted from the 5' end and/or 3' end of the full length viral genome. For example, the B19 genome (SEQ ID NO:5) cloned into pB19-4244 (FIG. 4) has 2 nucleic acids deleted from the 5' end and 3' end compared to the nucleic acid sequence of the full length genome (SEQ ID NO:38).

TABLE 1

| | | | | | | |
|---|---|---|---|---|---|---|
| 1 | aaatcaga | tgccgccggt | cgccgccggt | aggcgggact | tccggtacaa | gatggcggac |
| 59 | aattacgtca | tttcctgtga | cgtcatttcc | tgtgacgtca | cttccggtgg | gcgggacttc |
| 119 | cggaattagg | gttggctctg | ggccagcttg | cttggggttg | ccttgacact | aagacaagcg |
| 179 | gcgcgccgct | tgatcttagt | ggcacgtcaa | ccccaagcgc | tggcccagag | ccaaccctaa |
| 239 | ttccggaagt | cccgcccacc | ggaagtgacg | tcacaggaaa | tgacgtcaca | ggaaatgacg |
| 299 | taattgtccg | ccatcttgta | ccggaagtcc | cgcctaccgg | cggcgaccgg | cggcatctga |
| 359 | tttggtgtct | tcttttaaat | tttagcgggc | tttttcccg | ccttatgcaa | atgggcagcc |
| 419 | attttaagtg | ttttactata | attttattgg | tcagttttgt | aacggttaaa | atgggcggag |
| 479 | cgtaggcggg | gactacagta | tatatageac | agcactgccg | cagctctttc | tttctgggct |
| 539 | gctttttcct | ggactttctt | gctgtttttt | gtgagctaac | taacaggtat | ttatactact |
| 599 | tgttaatata | ctaacatgga | gctatttaga | ggggtgcttc | aagtttcttc | taatgttctg |
| 659 | gactgtgcta | acgataactg | gtggtgctct | ttactagatt | tagacacttc | tgactgggaa |
| 719 | ccactaactc | atactaacag | actaatggca | atatacttaa | gcagtgtggc | ttctaagctt |
| 779 | gaccttaccg | gggggccact | agcagggtgc | ttgtactttt | ttcaagcaga | atgtaacaaa |
| 839 | tttgaagaag | gctatcatat | tcatgtggtt | attgggggc | cagggttaaa | ccccagaaac |
| 899 | ctcacagtgt | gtgtagaggg | gttatttaat | aatgtacttt | atcactttgt | aactgaaaat |
| 959 | gtgaagctaa | aatttttgcc | aggaatgact | acaaaaggca | aatactttag | agatggagag |
| 1019 | cagtttatag | aaaactattt | aatgaaaaaa | atacctttaa | atgttgtatg | gtgtgttact |
| 1079 | aatattgatg | gatatataga | tacctgtatt | tctgctactt | ttagaagggg | agcttgccat |
| 1139 | gccaagaaac | cccgcattac | cacagccata | aatgatacta | gtagcgatgc | tggggagtct |
| 1199 | agcggcacag | gggcagaggt | tgtgccattt | aatgggaagg | gaactaaggc | tagcataaag |
| 1259 | tttcaaacta | tggtaaactg | gttgtgtgaa | aacagagtgt | ttacagagga | taagtggaaa |
| 1319 | ctagttgact | ttaaccagta | cactttacta | agcagtagtc | acagtggaag | ttttcaaatt |
| 1379 | caaagtgcac | taaaactagc | aatttataaa | gcaactaatt | tagtgcctac | tagcacattt |
| 1439 | ttattgcata | cagactttga | gcaggttatg | tgtattaaag | acaataaaat | tgttaaattg |
| 1499 | ttactttgtc | aaaactatga | ccccctattg | gtggggcagc | atgtgttaaa | gtggattgat |
| 1559 | aaaaaatgtg | gcaagaaaaa | tacactgtgg | ttttatgggc | cgccaagtac | aggaaaaaca |
| 1619 | aacttggcaa | tggccattgc | taaaagtgtt | ccagtatatg | gcatggttaa | ctggaataat |
| 1679 | gaaaactttc | catttaatga | tgtagcagga | aaaagcttgg | tggtctggga | tgaaggtatt |
| 1739 | attaagtcta | caattgtaga | agctgcaaaa | gccattttag | gcgggcaacc | caccagggta |
| 1799 | gatcaaaaaa | tgcgtggaag | tgtagctgtg | cctggagtac | ctgtggttat | aaccagcaat |
| 1859 | ggtgacatta | cttttgttgt | aagcgggaac | actacaacaa | ctgtacatgc | taaagcctta |
| 1919 | aaagagcgca | tggtaaagtt | aaactttact | gtaagatgca | gccctgacat | ggggttacta |
| 1979 | acagaggctg | atgtacaaca | gtggcttaca | tggtgtaatg | cacaaagctg | ggaccactat |
| 2039 | gaaaactggg | caataaacta | cacttttgat | ttccctggaa | ttaatgcaga | tgccctccac |
| 2099 | ccagacctcc | aaaccacccc | aattgtcaca | gacaccagta | tcagcagcag | tggtggtgaa |
| 2159 | agctctgaag | aactcagtga | aagcagcttt | tttaacctca | tcaccccagg | cgcctggaac |
| 2219 | actgaaaccc | cgcgctctag | tacgcccatc | cccgggacca | gttcaggaga | atcatttgtc |
| 2279 | ggaagcccag | tttcctccga | agttgtagct | gcatcgtggg | aagaagcctt | ctacacacct |
| 2339 | ttggcagacc | agtttcgtga | actgttagtt | ggggttgatt | atgtgtggga | cggtgtaagg |

TABLE 1-continued

| | | | | | | |
|---|---|---|---|---|---|---|
| 2399 | ggtttacctg | tgtgttgtgt | gcaacatatt | aacaatagtg | ggggaggctt | gggactttgt |
| 2459 | ccccattgca | ttaatgtagg | ggcttggtat | aatggatgga | aatttcgaga | atttacccca |
| 2519 | gatttggtgc | gatgtagctg | ccatgtggga | gcttctaatc | ccttttctgt | gctaacctgc |
| 2579 | aaaaaatgtg | cttacctgtc | tggattgcaa | agctttgtag | attatgagta | aagaaagtgg |
| 2639 | caaatggtgg | gaaagtgatg | atgaatttgc | taaagctgtg | tatcagcaat | ttgtggaatt |
| 2699 | ttatgaaaag | gttactggaa | cagacttaga | gcttattcaa | atattaaaag | atcattataa |
| 2759 | tatttcttta | gataatcccc | tagaaaaccc | atcctctctg | tttgacttag | ttgctcgcat |
| 2819 | taaaaataac | cttaaaaatt | ctccagactt | atatagtcat | cattttcaaa | gtcatggaca |
| 2879 | gttatctgac | cacccccatg | ccttatcatc | cagtagcagt | catgcagaac | ctagaggaga |
| 2939 | agatgcagta | ttatctagtg | aagacttaca | caagcctggg | caagttagcg | tacaactacc |
| 2999 | cggtactaac | tatgttgggc | ctggcaatga | gctacaagct | gggcccccgc | aaagtgctgt |
| 3059 | tgacagtgct | gcaaggattc | atgactttag | gtatagccaa | ctggctaagt | tgggaataaa |
| 3119 | tccatatact | cattggactg | tagcagatga | agagctttta | aaaaatataa | aaaatgaaac |
| 3179 | tgggtttcaa | gcacaagtag | taaaagacta | ctttacttta | aaaggtgcag | ctgcccctgt |
| 3239 | ggcccatttt | caaggaagtt | tgccggaagt | tcccgcttac | aacgcctcag | aaaaatacccc |
| 3299 | aagcatgact | tcagttaatt | ctgcagaagc | cagcactggt | gcaggagggg | ggggcagtaa |
| 3359 | tcctgtcaaa | agcatgtgga | gtgagggggc | cacttttagt | gccaactctg | tgacttgtac |
| 3419 | atttctaga | cagtttttaa | ttccatatga | cccagagcac | cattataagg | tgttttctcc |
| 3479 | cgcagcaagt | agctgccaca | atgccagtgg | aaaggaggca | aaggtttgca | ccattagtcc |
| 3539 | cataatggga | tactcaaccc | catggagata | tttagatttt | aatgctttaa | acttattttt |
| 3599 | ttcaccttta | gagtttcagc | acttaattga | aaattatgga | agtatagctc | ctgatgcttt |
| 3659 | aactgtaacc | atatcagaaa | ttgctgttaa | ggatgttaca | gacaaaactg | gagggggggt |
| 3719 | gcaggttact | gacagcacta | cagggcgcct | atgcatgtta | gtagaccatg | aatacaagta |
| 3779 | cccatatgtg | ttagggcaag | gtcaagatac | tttagcccca | gaacttccta | tttgggtata |
| 3839 | ctttcccct | caatatgctt | acttaacagt | aggagatgtt | aacacacaag | gaatttctgg |
| 3899 | agacagcaaa | aaattagcaa | gtgaagaatc | agcattttat | gttttggaac | acagttcttt |
| 3959 | tcagctttta | ggtacaggag | gtacagcaac | tatgtcttat | aagtttcctc | cagtgccccc |
| 4019 | agaaaattta | gagggctgca | gtcaacactt | ttatgagatg | tacaatccct | tatacggatc |
| 4079 | ccgcttaggg | gttcctgaca | cattaggagg | tgacccaaaa | tttagatctt | taacacatga |
| 4139 | agaccatgca | attcagcccc | aaaacttcat | gccagggcca | ctagtaaact | cagtgtctac |
| 4199 | aaaggaggga | gacagctcta | atactggagc | tgggaaagcc | ttaacaggcc | ttagcacagg |
| 4259 | tacctctcaa | aacactagaa | tatccttacg | cccggggcca | gtgtctcagc | cgtaccacca |
| 4319 | ctgggacaca | gataaatatg | tcacaggaat | aaatgctatt | tctcatggtc | agaccactta |
| 4379 | tggtaacgct | gaagacaaag | agtatcagca | aggagtgggt | agatttccaa | atgaaaaaga |
| 4439 | acagctaaaa | cagttacagg | gtttaaacat | gcacacctac | tttcccaata | aaggaaccca |
| 4499 | gcaatataca | gatcaaattg | agcgccccct | aatggtgggt | tctgtatgga | acagaagagc |
| 4559 | ccttcactat | gaaagccagc | tgtggagtaa | aattccaaat | ttagatgaca | gttttaaaac |
| 4619 | tcagtttgca | gccttaggag | gatggggttt | gcatcagcca | cctcctcaaa | tatttttaaa |
| 4679 | aatattacca | caaagtgggc | caattggagg | tattaaatca | atgggaatta | ctaccttagt |
| 4739 | tcagtatgcc | gtgggaatta | tgacagtaac | catgacattt | aaattggggc | cccgtaaagc |

TABLE 1-continued

| | | | | | | |
|---|---|---|---|---|---|---|
| 4799 | tacgggacgg | tggaatcctc | aacctggagt | atatcccccg | cacgcagcag | gtcatttacc |
| 4859 | atatgtacta | tatgacccta | cagctacaga | tgcaaaacaa | caccacagac | atggatatga |
| 4919 | aaagcctgaa | gaattgtgga | cagccaaaag | ccgtgtgcac | ccattgtaaa | cactccccac |
| 4979 | cgtgccctca | gccaggatgc | gtaactaaac | gcccaccagt | accacccaga | ctgtacctgc |
| 5039 | cccctcctat | acctataaga | cagcctaaca | caaaagatat | agacaatgta | gaatttaagt |
| 5099 | atttaaccag | atatgaacaa | catgttatta | gaatgttaag | attgtgtaat | atgtatcaaa |
| 5159 | atttagaaaa | ataaacgttt | gttgtggtta | aaaaattatg | ttgttgcgct | ttaaaaattt |
| 5219 | aaaagaagac | accaaatcag | atgccgccgg | tcgccgccgg | taggcgggac | ttccggtaca |
| 5279 | agatggcgga | caattacgtc | atttcctgtg | acgtcatttc | ctgtgacgtc | acttccggtg |
| 5339 | ggcggaactt | ccggaattag | ggttggctct | gggccagcgc | ttggggttga | cgtgccacta |
| 5399 | agatcaagcg | gcgcgccgct | tgtcttagtg | tcaaggcaac | cccaagcaag | ctggcccaga |
| 5459 | gccaacccta | attccggaag | tcccgcccac | cggaagtgac | gtcacaggaa | atgacgtcac |
| 5519 | aggaaatgac | gtaattgtcc | gccatcttgt | accggaagtc | ccgcctaccg | gcggcgaccg |
| 5579 | gcggcatctg | attt | | | | |

"Variants" of the parvovirus B19 viral genome refer to a sequence of a viral genome that differs from a reference sequence and includes "naturally occurring" variants as well as variants that are prepared by alteration of one more nucleotides. In some embodiments, when the viral genome has the sequence of a naturally occurring isolate, the reference sequence may be human parvovirus B19-Au (GeneBank accession number M13178; SEQ ID NO:24), which lacks intact ITRs at both 5' and 3' ends of the genome and the variant has at least 90% sequence identity to the reference sequence. In other cases, a variant may be prepared by altering or modifying the nucleic acid sequence of the viral genome including by addition, substitution, and deletion of nucleotides. In that case, the reference sequence can be that of parvovirus B19 comprising a polynucleotide sequence of SEQ ID NO:5. In some embodiments, a parvovirus genome has at least 90% sequence identity, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to that of a parvovirus B19 genome comprising a nucleic acid sequence of parvovirus B19 Au (GeneBank accession number M13178; SEQ ID NO:24) or a parvovirus B19 comprising a polynucleotide sequence of SEQ ID NO:5.

An "infectious clone" of parvovirus B19 as used herein refers to a full-length genome or portion of a genome of a parvovirus B19 isolate cloned into a replicable vector that provides for amplification of the viral genome in a cell. In some embodiments, a portion of the parvovirus B19 genome comprises or consists of nucleic acid sequence encoding at least one ITR, VP2, NS, and 11-kDa in a single replicable vector. In other embodiment, the viral genome is a full-length genome. The replicable vector provides for introduction and amplification of the viral genome in a wide variety of prokaryotic and eukaryotic cells The term "erythroid progenitor cell" as used herein refers to a red blood cell precursor cell that differentiates to produce red blood cells.

"Electrical nuclear transport" is a method of introducing nucleic acids into cells such as eukaryotic cells using an electrical current. In some embodiments, in electrical nuclear transport, a recombinant plasmid is transported into the nucleus of cells. Greater amounts of DNA are transported into the nucleus of dividing cells with electrical nuclear transport than may be expected by cell division alone, thereby substantially increasing the likelihood of integration of complete expression cassettes. Electrical nuclear transport methods and buffer systems are described in U.S. 20040014220.

The term "full length genome" refers to a complete coding sequence of a viral genome that comprises at least 75% or greater of the nucleotide sequence that forms the hairpin of the ITR at the 5' end and 3' end of the genome. In an embodiment, the coding sequence comprises nucleic acid sequence encoding VP1, VP2, NS, 11-kDa protein, 7.5-kDa protein, and putative protein X. In another embodiment, ITRs at each end of the full length clone may have 1 to about 5 deletions at each end and retain the ability to provide for replication and expression of viral proteins. In preferred embodiments, the ITR has at least about 94%, more preferably 95%, more preferable 96%, more preferably 97%, more preferably 98%, more preferably about 99%, and more preferably 100% of the sequence of that of viral genome isolated from nature, such as that of SEQ ID NO:5 or SEQ ID:24.

The terms fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

The term "infection" as used herein refers to the introduction B19 viral DNA into a cell wherein introduction of the viral DNA into the cell is mediated by B19 capsid. Cells are typically infected by contacting the cell with B19 virus. Infection of a cell by B19 virus may be determined by analyzing the cell for increase in viral DNA including by detecting the presence or increase of spliced capsid transcripts and/or unspliced NS transcripts and/or capsid proteins.

The term "immunogenic effective amount" of a parvovirus B19 or component of a parvovirus refers to an amount of a parvovirus B19 or component thereof that induces an immune response in an animal. The immune response may be determined by measuring a T or B cell response. Typically, the induction of an immune response is determined by the detection of antibodies specific for parvovirus B19 or component thereof.

An "isolated" antibody is an antibody that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source. Preferably, the isolated nucleic is free of association with all components with which it is naturally associated. An isolated nucleic acid molecule is other than in the form or setting in which it is found in nature. Isolated nucleic acid molecules encoding, for example, B19 genome or B19 viral proteins therefore are distinguished from nucleic acid molecules encoding B19 viral proteins or a B19 genome as it may exist in nature. In an embodiment, the B19 genome comprises a nucleic acid sequence encoding one or more of 11-kDa protein, VP1, VP2, NS, 7.5-kDa protein, and protein X. In another embodiment, the polynucleotides have a nucleotide sequence that encodes a B19 genome that has greater than 99% nucleic acid sequence identity to SEQ ID NO:5 (Table 1). Preferably, the polynucleotide encodes an infectious clone of parvovirus B19.

"ITR" or "ITR sequence" refers to an inverted terminal repeat of nucleotides in a nucleic acid such as a viral genome. The ITRs include an imperfect palindrome that allows for the formation of a double stranded hairpin with some areas of mismatch that form bubbles. The ITRs serve as a primer for viral replication and contain a recognition site for NS protein that may be required for viral replication and assembling. In some embodiments, the location and number of the bubbles or areas of mismatch are conserved as well as the NS binding site. The NS binding site provides for cleavage and replication of the viral genome. In an embodiment, the parvovirus B19 genome comprises one or more ITR sequences. Preferably, the B19 genome comprises an ITR sequence at the 5' end and the 3' end. An ITR may be about 350 nucleotides to about 400 nucleotides in length. An imperfect palindrome may be formed by about 350 to about 370 of the distal nucleotides, more preferably about 360 to about 365 of the distal nucleotides. Preferably the imperfect palindrome forms a double-stranded hairpin. In an embodiment, the ITRs are about 383 nucleotides in length, of which about 365 of the distal nucleotides are imperfect palindromes that form double-stranded hairpins. In another embodiment, the ITRs are about 381 nucleotides in length, of which about 361 of the distal nucleotides are imperfect palindromes that form double-stranded hairpins. In some embodiments, a B19 genome comprises at least 75% of the nucleotide sequence that forms the hairpin in the ITR at the 5' end and 3' end of the genome. In other embodiments, the ITRs may have 1 to about 5 nucleotides deleted from each end. In a further embodiment, the ITRs comprise a nucleic acid sequence of SEQ ID NO:1 and/or SEQ ID NO:2. The ITRs may be in the "flip" or "flop" orientation.

The term "permissive cells" means cells in which parvovirus B19 isolates can be cultured. The permissive cells are eukaryotic cells. Examples of permissive cells include, but are not limited to primary erythroid progenitor cells from bone marrow, blood, or fetal liver cells, megakaryoblast cells, UT7/Epo cells, UT7/Epo-S1 cells, KU812Ep6 cells, JK-1 cells, and MB-O2 cells.

"Percent (%) nucleic acid sequence identity" with respect to the nucleic acid sequences identified herein is defined as the percentage of nucleotides in a candidate sequence that are identical with the nucleotides in a reference B19 nucleic acid sequence, after aligning the sequences and introducing gaps, if necessary, to achieve the maximum percent sequence identity. In some embodiments, the reference B19 nucleic acid sequence is that of SEQ ID NO:5 or that of SEQ ID NO:24. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For purposes herein, the % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

100 times the fraction W/Z where W is the number of nucleotides scored as identical matches by the sequence alignment program in that program's alignment of A and B, and where Z is the total number of nucleotides in B. It will be appreciated that where the length of nucleic acid sequence A is not equal to the length of nucleic acid sequence B, the % nucleic acid sequence identity of A to B will not equal the % nucleic acid sequence identity of B to A.

"Recombinant" refers to a polynucleotide that has been isolated and/or altered by the hand of man or a B19 clone encoded by such a polynucleotide. A DNA sequence encoding all or a portion of a B19 viral genome may be isolated and combined with other control sequences in a vector. The other control sequences may be those that are found in the naturally occurring gene or others. The vector provides for introduction into host cells and amplification of the polynucleotide. The vectors described herein for B19 clones are introduced into cells and cultured under suitable conditions as known to those of skill in the art. Preferably, the host cell is a bacterial cell or a permissive cell.

The term "transformation" as used herein refers to introducing DNA into a bacterial cell so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation is electroporation.

The term "transfection" as used herein refers to introducing DNA into a eukaryotic cell so that the DNA is replicable, either as an extrachromosomal element or by chromosomal integrant. Depending on the host cell used, transfection is done using standard techniques appropriate to such cells. Methods for transfecting eukaryotic cells include polyethyleneglycol/DMSO, liposomes, electroporation, and electrical nuclear transport.

The term "transfection efficiency" as used herein means the percentage of total cells contacted with a nucleic acid, such as a plasmid, that take up one or more copies of the plasmid. Tranfection efficiency can also be expressed as the total number of cells that take up one or more copies of the plasmid per μg of plasmid. If the plasmid contains a reporter gene, transfection efficiency of cells can also be expressed in units of expression of the reporter gene per cell.

The term "replicable vector," as used herein, is intended to refer to a nucleic acid molecule capable of transporting another nucleic acid to which it has been linked into a cell and providing for amplification of the nucleic acid. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. In the present specification, "plasmid" and "vector" may be used interchangeably as the plasmid is the most commonly used form of vector. In some embodiments, the vector is a vector that can replicate to high copy number in a cell.

II. Modes for Carrying Out the Invention

Previous attempts to produce infectious clones of parvovirus B19 have been unsuccessful due to deletions in the ITR sequences (Shade et al., 1986, *J. Virol.,* 58:921-936) and the instability of the ITRs in bacterial cells. In addition, parvovirus B19 can be cultured in permissive cells but the amount of virus produced in these cells is very small. There have been no methods or clones of the viral genome that can provide for consistent production of infectious virus. Utilizing the methods of the invention, the genome of parvovirus B19 isolate was cloned and sequenced. A vector was prepared comprising a B19 viral genome and the vector was used to clone the viral genome. The parvovirus B19 clone can be introduced into other cells types (whether permissive or not) to produce infectious virus.

The infectious clone and methods described herein can be utilized in a variety of assays and to develop therapeutic products. The infectious clone is useful for producing infectious virus. An in vitro system for producing infectious virus particles can be used in screening methods to identify agents such as antibodies or antisense molecules that can inhibit viral infectivity or reproduction. The infectious virus and/or infectious virus in a host cell can be utilized to form immunogenic compositions to prepare therapeutic antibodies or vaccine components. Antibodies and primers can be developed to specifically identify different parvovirus B19 isolates. The ability to produce infectious virus in vitro is also useful to develop attenuated strains of the virus that may be utilized in vaccines.

A. Methods of the Invention

One aspect of the invention involves a method of cloning a viral genome that has one or more inverted repeats or secondary structure of nucleic acid that is unstable in cells. A method of the invention comprises introducing the viral genome into a bacterial cell that is deficient in recombinase enzymes such as recA1, end A1, recB, recJ or combinations thereof. The bacterial cells are incubated at a low temperature, for example about 25° C. to 35° C., preferably about 25° C. to 32° C., and more preferably about 28° C. to 31° C., and most preferably about 30° C. The cells are incubated for a time sufficient to allow amplification of the viral genome. Preferably, the incubation time is about 8 to 24 hours, more preferably about 8 to 12 hours. The viral genome is recovered from the bacterial cells.

In some embodiments, the methods of the invention include a method for cloning an infectious parvovirus B19 clone. In an embodiment, the method comprises introducing a replicable vector comprising a parvovirus B19 viral genome or portion thereof into prokaryotic cells that are deficient in major recombination genes, such as for example recA1, endA1, recB and/or recJ or combinations thereof. The cells are incubated at a low temperature for a time sufficient to allow amplification of the vector. The infectious clone is recovered from the prokaryotic cells. Once the infectious clone is prepared it can be introduced into other cell types, whether permissive or not, and provide infectious virus.

Preparing a Clone of the Viral Genome

The infectious clone is comprised of all or a portion of a viral genome of parvovirus B19 and a replicable vector that can provide for amplification of the viral genome in a cell, such as a bacterial cell. In some embodiments, the vector has a bacterial origin of replication. In some embodiments, the vector is a plasmid. In some embodiments, the vector can be selected based on the host cell as well as other characteristics such as compatibility with host cell, copy number, and restriction sites. Vectors that can be used in the invention include, without limitation, pBR322, pProExHTb, pUC19, and pBluescript KS.

The method of cloning a parvovirus genome can be applied to any parvovirus genome. The parvovirus genome includes those obtained from known isolates, those isolated from samples from infected tissues, or parvovirus genomes from any source including those that have been modified. All or a portion of the viral genome can be cloned. In some embodiments, the parvovirus B19 genome is a full-length genome. In other embodiments, a portion of the parvovirus genome comprises or consists of nucleic acid sequence encoding at least one ITR, VP2, NS and the 11 kDa protein in a single replicable vector. The portion of the viral genome is that portion that is sufficient to provide for production of infectious virus. In other embodiments, the parvovirus genome comprises or consists of a nucleic acid encoding an 11R at the 5' end and an ITR at the 3' end, VP2, NS and the 11 kDa protein in a single replicable vector. In an embodiment, the B19 genome comprises a polynucleotide encoding an infectious B19 clone having at least 90% nucleic acid sequence identity with SEQ ID NO:5 and/or SEQ ID NO:24. In another embodiment, the B19 genome comprises a nucleic acid sequence of SEQ ID NO:5.

The parvovirus B19 genome preferably comprises one or more ITR sequences. The ITRs include an imperfect palindrome that allows for the formation of a double stranded hairpin with some areas of mismatch that form bubbles. The ITRs serve as a primer for viral replication and contain a recognition site for NS protein that may be required for viral replication and assembling. In some embodiments, the nucleotide sequence that forms the hairpins is retained and conserved. In some embodiments, the location and number of the bubbles or areas of mismatch are conserved as well as the NS binding site. The NS binding site provides for cleavage and replication of the viral genome.

In an embodiment, the parvovirus B19 genome comprises one or more ITR sequences. Preferably, the B19 genome comprises an ITR sequence at the 5' end and the 3' end. An ITR may be about 350 nucleotides to about 400 nucleotides in length. An imperfect palindrome may be formed by about 350 to about 370 of the distal nucleotides, more preferably about 360 to about 365 of the distal nucleotides. Preferably the imperfect palindrome forms a double-stranded hairpin. In an embodiment, the ITRs are about 383 nucleotides in length, of which about 365 of the distal nucleotides are imperfect palindromes that form double-stranded hairpins. In another embodiment, the ITRs are about 381 nucleotides in length, of which about 361 of the distal nucleotides are imperfect palindromes that form double-stranded hairpins. In some embodiments, a B19 genome comprises at least 75% of the nucleotide sequence that forms the hairpin in the ITR at the 5' end and 3' end of the genome. In other embodiments, the ITRs may have 1 to about 5 nucleotides deleted from each end. In preferred embodiments, the ITR has at least about 94%, more preferably 95%, more preferably 96%, more preferably 97%, more preferably 98%, more preferably about 99%, and more preferably 100% of the sequence of that of viral genome isolated from nature, such as that of SEQ ID NO:5 or SEQ ID:24. In a further embodiment, the ITRs comprise a nucleic acid sequence of SEQ ID NO:1 and/or SEQ ID NO:2. The ITRs may be in the "flip" or "flop" orientation.

The parvovirus genome may have variation due to variation in naturally occurring isolates. For example, isolates of parvovirus B19 from infected tissues can have about 90% sequence identity or greater to that of parvovirus B19 Au (GeneBank accession number M13178; SEQ ID NO:24) In some embodiments, a parvovirus genome has at least 90% sequence identity, more preferably more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to that of a parvovirus B19 genome comprising a nucleic acid sequence of parvovirus B19 Au GeneBank accession number M13178; SEQ ID NO:24).

In some cases, alterations or modifications may be made to the nucleic acid sequence of the viral genome of a viral isolate using standard methods to form variant viral genomes. The alterations may be made to add or delete characteristics to the nucleic acid sequence. For example, it may be desirable to add or delete a restriction site or add a sequence that can serve to identify the viral genome. In a specific embodiment, a vector, identified as pB19-M20 comprises a full-length clone of parvovirus B19 having a sequence of SEQ ID NO:5 but with a change at nucleotide 2285 from a cytosine to a thymine, resulting in conversion of BsrI site to a Dde site. In another embodiment, a vector, identified as pB19-4244d comprises a full-length clone of parvovirus B19 having a sequence of SEQ ID NO:5 but with a change to eliminate an XbaI restriction site.

Alternatively it may be desirable to add a nucleic acid sequence that encodes a heterologous polypeptide to the infectious clone. Such a heterologous polypeptide may include tag polypeptides such as poly-histidine (poly-His) or poly-histidine-glycine (poly-His-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; an "-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)] The heterologous polypeptides are combined with viral proteins to form fusion proteins. Epitopes from heterologous proteins may be combined with parvovirus B19 proteins to form fusion proteins useful for immunogenic compositions.

Preferably, the variant viral genome has at least 90% sequence identity, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater sequence identity to that of a parvovirus B19 genome comprising a nucleic acid sequence of SEQ. ID. NO:5. In some embodiments, the parvovirus genome, preferably has 99.2% sequence identity, more preferably 99.3%, more preferably 99.4%, more preferably 99.5%, more preferably 99.6%, more preferably 99.7%, more preferably 99.8%, and more preferably 99.9% or greater sequence identity to that of a parvovirus B19 genome comprising a polynucleotide sequence of SEQ. M. NO:5.

Figure 3:
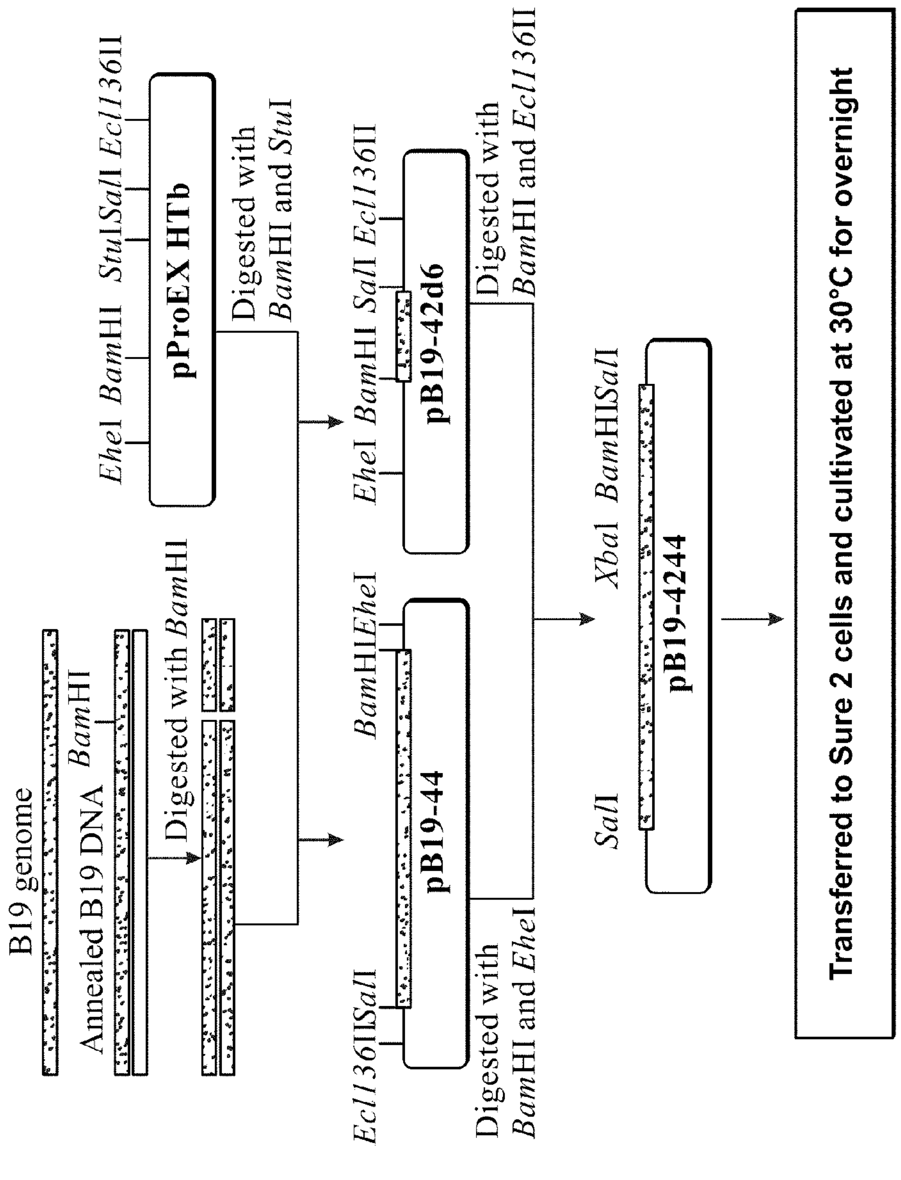
FIG. 3 shows the experimental strategy used to construct an infectious clone of parvovirus B19.
Figure 4:
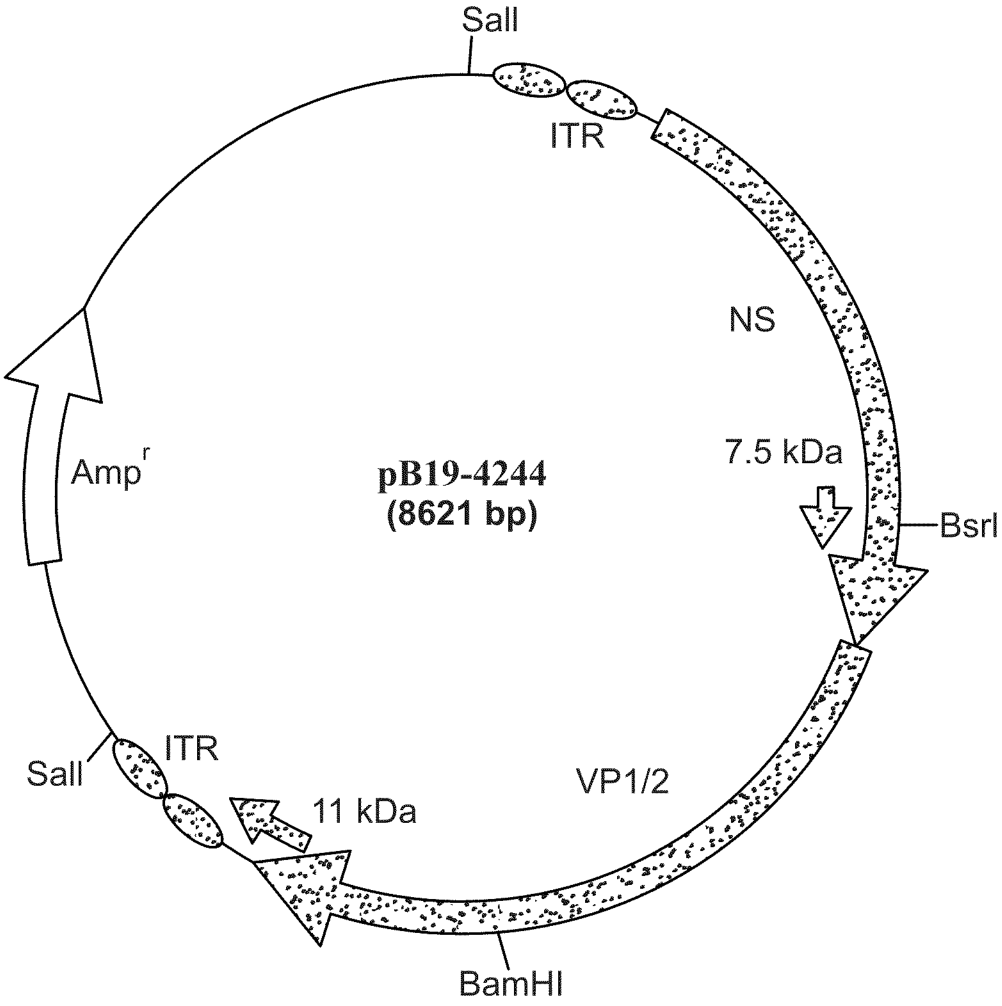
FIG. 4 shows a map of recombinant plasmid pB19-4244, which contains an insert comprising 5592 nucleotides of full-length B19 genome (SEQ ID NO:5). The arrows indicate genes. Shaded arrows indicate genes in the B19 genome. The shaded circles at the 5' and 3' ends of the B19 genome indicate the ITR sequences.

In some embodiments, the B19 genome is cloned by cloning at least two portions of the viral genome into separate vectors and recombining the two portions into a single vector. Preferably, the two portions of the viral genome comprise an ITR at the end of the portion. The portions of the viral genome can be obtained by digesting the genome with a restriction enzyme that cuts the genome at a location between the ITRs. Preferably the restriction enzyme cuts the genome at a location at least about 800 nucleotides from the ITR. The portions may be cut and religated to reduce the vector size and eliminate undesired restriction sites. For example, the B19 genome may be digested with BamHI. The two fragments (right end genome fragment and left end genome fragment) generated by BamHI digestion are ligated into separate BamHI-StuI digested pProEX HTb vectors (Invitrogen-Life Technologies). See, for example, FIG. 3. To reduce the vector size and eliminate undesired restriction sites, clones that contain the right end of the genome (pB19-42d6) may be digested with EcoRV and religated. The full-length genome is generated by digesting the plasmid containing the left end genome fragment (pB19-44) with BamHI and Ecl136II and cloning the fragment containing the left end genome fragment into the BamHI/EheI site of the pB19-42d6 plasmid (FIGS. 3 and 4).

In some embodiments, it may be desirable to achieve a high efficiency of ligation. In that case, it is preferred that at least about 0.25 μg of the viral genome is combined with about 1 μg of the vector, more preferably about 0.25 to about 0.5 μg of viral genome per 1 μg amount of vector. The viral genome can be obtained from serum or infected cells. The isolated virus may be high titer virus and/or concentrated to achieve the amount of viral genome necessary for ligation. In some embodiments, the parvovirus B19 isolated from a sample and used to prepare the clone is present in the sample at about $10^8$ to about $10^{14}$ genome copies/ml of original sample, more preferably about $10^8$ to about $10^{12}$ genome copies/ml of original sample. Virus can be concentrated from serum or infected cells using standard methods known in the art, such as for example, velocity and/or equilibrium density centrifugation using sucrose solutions in low-salt buffer. Preferably, viral genome is concentrated at about $10^8$ to about $10^{14}$ genome copies/100 μl of physiological solution, more preferably about $10^8$ to about $10^{12}$ genome copies/100 μl of physiological solution.

Introducing and Amplifying a Parvovirus B19 Clone in Prokaryotic Cells

According to the method of cloning a viral genome, a vector comprising all or a portion of the viral genome is introduced into a prokaryotic cell. Methods of introducing vectors into cells are known to those of skill in the art and include transformation methods such as calcium salt precipitation, liposomes, polyethylene glycol/DMSO, electroporation and electro nuclear transport. In some embodiments, the vector is introduced into bacterial cells by electroporation.

The bacterial cells are preferably deficient in recombinase enzymes such as recA1, endA1, recB, recJ, or combinations thereof. In some embodiments, the transformed bacterial cells are preferably *E. coli* cells. In an embodiment, the *E. coli* cells are McrA-, McrCB-, McrF-, Mrr-, HsdR-, and endA deficient. In another embodiment, the *E. coli* cells comprise a genotype of e14-(McrA-)Δ(mcrCB-hsdSMR-mrr)171 endA1 supE44 thi-1 gyrA96 relA1 lac recB recJ sbcC umuC::Tn5 (Kanr) uvrC [F' proAB lacIqZ.M15 Tn10 (Tetr)]; $F^-$ mcrA Δ(mrr-hsdRMS-mcrBC) recA1 endA1 lon gyrA96 thi-1 supE44 relA1$\lambda^-$ Δ(lac-proAB); or $F^-$ mcrA Δ(mcrBC-hsdRMS-mrr) recA1 endA1 lon gyrA96 thi supE44 relA1$\lambda^-$ Δ(lac-proAB). In another embodiment, the *E. coli* cells are cells, such as for example SURE2® cells (Stratagene, La Jolla, Calif.); Stbl2 cells or Stble 4 cells (Invitrogen, Carlsbad, Calif.).

In an embodiment, the incubation temperature for the transformed prokaryotic cells is about 25° C. to about 35° C., preferably, about 25° C. to about 32° C., more preferably about 30° C. to about 32° C., more preferably about 30° C. The prokaryotic cells preferably are plated immediately following introduction of the viral genome and incubated for a sufficient time to allow for amplification of the viral genome, preferably, from about 12 to about 24 hours, more preferably from about 16 to about 18 hours. The clone can be recovered from the cells using standard methods. Infectious clones are those that can produce viral DNA, proteins or particles when introduced into other cell types.

Introducing the Infectious Clone into Other Cell Types

Another aspect of the invention, provides a method of producing an infectious clone or infectious viral particles of parvovirus B19 in a eukaryotic cell. This method can also be utilized to identify and/or confirm that the parvovirus B19 clone produced is infectious. After the clone is amplified in a bacterial cell and recovered, the infectious clone may be introduced into other cell types (whether permissive or not) to identify whether the clone can produce infectious virus or for the production of infectious virus. The method provides for production of infectious virus in vitro. Utilizing an infectious clone allows introduction of the viral genome into a cell without the need for entry mediated by viral proteins such as the capsid protein. The method comprises introducing a vector comprising an infectious clone of parvovirus B19 or all or a portion of a viral genome into a eukaryotic cell and incubating the cell for a sufficient time to produce infectious virus and optionally, detecting production of infectious virus. The method of identifying an infectious clone comprises introducing a vector comprising all or a portion of a viral genome into a eukaryotic cell; incubating the cell for a sufficient time to produce infectious virus; and detecting production of infectious virus.

In some embodiments, a high efficiency of introduction of the vector into eukaryotic cells is desired. Preferably, the method of introduction employed achieves a transfection efficiency of at least about 15% to 100% efficiency, more preferably about 30 to 50% efficiency. The method is also selected to minimize cytotoxicity to the cells. Preferably, about 20% or greater of the cells are viable and more preferably about 50% of the cells or greater. In some embodiments, the vector may be cut with one or more restriction enzymes to enhance viral replication.

In an embodiment, eukaryotic cells are transfected with an electric current. Methods of transfecting eukaryotic cells utilizing an electric current are known in the art, such as for example, electroporation (Sambrook, et al., 1989, Molecular Cloning, A Laboratory Manual, Vols. 1-3, Cold Spring Harbor Press, Cold Spring Harbor, N.Y. or Davis et al., 1986, *Basic Methods in Molecular Biology*) and electrical nuclear transport (U.S. 20040014220).

In an embodiment, the eukaryotic cells are transfected by electrical nuclear transport. The cells are exposed to an electrical pulse comprising a field strength of about 2 kV/cm to about 10 kV/cm, a duration of about 10 μsec to about 200 μsec, and a current of at about 1 A to about 2.5 A followed by a current flow of about 1 A to about 2.5 A for about 1 msec to about 50 msec. A buffer suitable for use in electrical nuclear transport comprises 0.42 mM $Ca(NO_3)_2$, 5.36 mM KCl, 0.41 mM $MgSO_4$, 103 mM NaCl, 23.8 mM $NaHCO_3$, 5.64 mM $Na_2HPO_4$, 11.1 mM d(+) glucose, 3.25 μM glutathione, 20 mM Hepes, and pH 7.3. Following transformation, the permissive cells may be incubated for about 10 min at 37° C. before being plated in prewarmed (37° C.) culture medium with serum and incubated at 37° C.

Commercially available devices and buffer systems for electrical nuclear transport, such as for example the AMAXA CELL LINE NUCLEOFECTOR™ system (Amaxa Biosystems Inc., Nattermannallee, Germany; www-amaxa-com), have been customized to transduce specific types of eukaryotic cells such as, for example, UT7/Epo cells UT7/Epo-S1 cells. In an embodiment, UT7/Epo cells or UT7/Epo-S1 cells are transfected using NUCLEOFECTOR™ reagent R and program T-20 on the NUCLEOFECTOR™ device according to the manufacturer's instructions (Amaxa Biosystems Inc., Nattermannallee, Germany).

The eukaryotic cells include, but are not limited to, erythroid progenitor cells, fetal liver cells, UT7/EPO cells, UT7/EPO-S1 cells, or KU812Ep6 cells. In an embodiment, permissive cells include, but are not limited to, primary erythroid progenitor cells from bone marrow and blood; megakaryoblast cells, fetal liver cells; UT7/Epo cells, UT7/Epo-S1 cells, KU812Ep6 cells, JK-1 and MB-O2. Other eukaryotic cell types may also be utilized including 293 cells, CHO cells, Cos cells, Hela cells, BHK cells and SF9 cells.

The cells may be incubated in culture medium following introduction of the vector comprising a parvovirus B19 viral genome or plated in culture medium immediately following transfection. The cells may be incubated for about 10 min to about 30 min at about 25° C. to about 37° C., more preferably about 30° C. to about 37° C., more preferably 37° C. before plating the cells. Once plated, the cells are incubated under conditions sufficient to provide for production of infectious virus. In some embodiments, the cells are incubated at 37° C. for about 2 to about 4 hours, more preferably at least about 6 hours, more preferably at least about 12 hours, more preferably at least about 18 hours, more preferably at least about 24 hours. In an embodiment, the cells are incubated for about 72 hours post-transfection. Infectious virus particles can be isolated or recovered from cell lysates.

To determine if B19 virus produced by the methods of the invention is infectious, supernatants prepared from cell lysates of the cells can be used to infect non-transfected cells. In an embodiment, the non-transfected cells are UT7/Epo-S1 cells. Production of infectious B19 virus by the methods of the invention may be detected by analyzing the infected cells for spliced transcripts of B19 genes. Preferably the spliced transcripts are spliced capsid transcripts encoding, for example, VP1 or VP2. In an embodiment, infectious B19 is identified by contacting cells with supernatant from the transformed cells and analyzing the contacted cells for B19 spliced transcripts. Detection of spliced capsid transcripts indicates the parvovirus B19 is infectious. Production of infectious B19 virus may be detected by analyzing the infected cells for B19 viral proteins. Preferably the B19 viral proteins are capsid proteins, such as for example VP1 and VP2. In an embodiment, infectious parvovirus B19 virus is identified by contacting cells with supernatant from the transfected cells and analyzing the contacted cells for B19 viral proteins. Detection of B19 capsid proteins indicates the parvovirus B19 is infectious. In another embodiment, in vitro neutralization assays can be performed to test whether neutralizing monoclonal antibodies against parvovirus B19 capsids are able to block the infection caused by the cell lysates of transfected cells. Blocking of infectivity by neutralizing antibodies indicates the virus is infectious.

B. Infectious Parvovirus B19 Clones

The invention also provides infectious B19 clones and polynucleotides encoding the infectious clones. The infectious clones may be produced by the methods of the invention. The infectious clone is comprised of all or a portion of a viral genome of parvovirus B19 and a replicable vector that can provide for amplification of the viral genome in a bacterial cell, in some embodiments, the vector has a bacterial origin of replication. In some embodiments, the vector is a plasmid. In some embodiments, the vector can be selected based on the host cell as well as other characteristics such as compatibility with host cell, copy number, and restriction sites. Vectors that can be used in the invention include, without limitation, pBR322, pProExHTb, pUC19, and pBluescript KS. Preferably, the vector provides for high copy number of the infectious clone in bacterial cells, eg about 50-100 copies per cell. Several embodiments of the infectious clones are described in the Examples and the Figures.

The method of cloning a parvovirus genome can be applied to any parvovirus genome. Thus, an infectious clone can comprise a parvovirus genome obtained from known isolates, those isolated from samples from infected tissues, or parvovirus genomes from any source including those genomes that have been modified. All or a portion of the viral genome can be cloned. In some embodiments, the parvovirus B19 genome is a full length genome. In other embodiments, a portion of the parvovirus genome comprises or consists of nucleic acid sequence encoding at least one ITR, VP2, NS and the 11 kDa protein in a single replicable vector. The portion of the viral genome is that portion that is sufficient to provide for production of infectious virus. In other embodiments, the parvovirus genome comprises or consists of a nucleic acid encoding an ITR at the 5' end and an ITR at the 3' end, VP2, NS and the 11 kDa protein in a single replicable vector. In an embodiment, the B19 genome comprises a polynucleotide encoding an infectious B19 clone having at least 90% nucleic acid sequence identity with SEQ ID NO:5. In another embodiment, the B19 genome comprises a nucleic acid sequence of SEQ ID NO:5.

The parvovirus B19 genome preferably comprises one or more ITR sequences. “ITR” or “ITR sequence” refers to an inverted terminal repeat of nucleotides in a nucleic acid such as a viral genome. The ITRs include an imperfect palindrome that allows for the formation of a double stranded hairpin with some areas of mismatch that form bubbles. The ITRs serve as a primer for viral replication and contain a recognition site for NS protein that may be required for viral replication and assembling. In some embodiments, the location and number of the bubbles or areas of mismatch are conserved as well as the NS binding site. The NS binding site provides for cleavage and replication of the viral genome. In an embodiment, the parvovirus B19 genome comprises one or more ITR sequences. Preferably, the B19 genome comprises an ITR sequence at the 5' end and the 3' end. An ITR may be about 350 nucleotides to about 400 nucleotides in length. An imperfect palindrome may be formed by about 350 to about 370 of the distal nucleotides, more preferably about 360 to about 365 of the distal nucleotides. Preferably the imperfect palindrome forms a double-stranded hairpin. In an embodiment, the ITRs are about 383 nucleotides in length, of which about 365 of the distal nucleotides are imperfect palindromes that form double-stranded hairpins. In another embodiment, the ITRs are about 381 nucleotides in length, of which about 361 of the distal nucleotides are imperfect palindromes that form double-stranded hairpins. In some embodiments, a B19 genome comprises at least 75% of the nucleotide sequence that forms the hairpin in the ITR at the 5' end and 3' end of the genome. In other embodiments, the ITRs may have 1 to about 5 nucleotides deleted from each end. In preferred embodiments, the ITR has at least about 94%, more preferably 95%, more preferable 96%, more preferably 97%, more preferably 98%, more preferably about 99%, and more preferably 100% of the sequence of that of viral genome isolated from nature, such as that of SEQ ID NO:5 or SEQ ID:24. In a further embodiment, the ITRs comprise a nucleic acid sequence of SEQ ID NO:1 and/or SEQ ID NO:2. The ITRs may be in the “flip” or “flop” orientation.

The parvovirus genome may have variation due to variation in naturally occurring isolates. For example, isolates of parvovirus B19 from infected tissues can have about 90% sequence identity or greater to that of parvovirus B19-Au (GeneBank Accession No. M13178; SEQ ID NO:24). In some embodiments, a parvovirus genome has at least 90% sequence identity, more preferably more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater to that of a parvovirus B19 genome comprising a nucleic acid sequence of parvovirus B19 Au (GeneBank Accession No. M13178; SEQ ID NO:24).

In some cases, alterations or modifications may be made to the nucleic acid sequence of the viral genome using standard methods. The alterations may be made to add or delete characteristics to the nucleic acid sequence. For example, it may be desirable to add or delete a restriction site or add a sequence that can serve to identify the viral genome. In a specific embodiment, a vector, identified as pB19-M20 comprises a full length clone of parvovirus B19 having a sequence of SEQ ID NO:5 but with a change at nucleotide 2285 from a cytosine to a thymine, resulting in conversion of BsrI site to a Dde site. In another embodiment, a vector, identified as pB19-

4244d comprises a full length clone of parvovirus B19 having a sequence of SEQ ID NO:5 but with a change to eliminate an XbaI restriction site.

Alternatively it may be desirable to add a nucleic acid sequence that encodes a heterologous polypeptide to the infectious clone. Such a heterologous polypeptide may include tag polypeptides such as poly-histidine (poly-His) or poly-histidine-glycine (poly-His-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; an "-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)]. Heterologous polypeptides are combined with viral proteins to form fusion proteins. Epitopes from other proteins may be combined with parvovirus B19 proteins to form fusion proteins useful as immunogenic compositions.

Preferably, the viral genome has at least 90% sequence identity, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% or greater to that of a parvovirus B19 genome comprising a nucleic acid sequence of SEQ. ID. NO:5. In some embodiments, the parvovirus genome, preferably has 99.2% sequence identity, more preferably 99.3%, more preferably 99.4%, more preferably 99.5%, more preferably 99.6%, more preferably 99.7%, more preferably 99.8%, and more preferably 99.9% or greater sequence identity to that of a parvovirus B19 genome comprising a nucleic acid sequence of SEQ. ID. NO:5.

In some embodiments, the B19 genome is cloned by, cloning at least two portions of the viral genome into separate vectors and recombining the two portions into a single vector. Preferably, two portions of the viral genome comprise an ITR at the end of the portion. The portions of the viral genome can be obtained by digesting the genome with a restriction enzyme that cuts the genome at a location between the ITRs. Preferably the restriction enzyme cuts the genome at a location at least about 800 nucleotides from the ITR. The portions may be cut and religated to reduce the vector size and eliminate undesired restriction sites. For example, the B19 genome may be digested with BamHI. The two fragments (right end genome fragment and left end genome fragment) generated by BamHI digestion are ligated into separate BamHI-StuI digested pProEX HTb vectors (Invitrogen-Life Technologies). See, for example, FIG. 3. To reduce the vector size and eliminate undesired restriction sites, clones that contain the right end of the genome (pB19-42d6) may be digested with EcoRV and religated. The full-length genome is generated by digesting the plasmid containing the left end genome fragment (pB19-44) with BamHI and Ecl136II and cloning the fragment containing the left end genome fragment into the BamHI/EheI site of the pB19-42d6 plasmid (FIGS. 3 and 4).

In some embodiments, it may be desirable to achieve a high efficiency of ligation. In that case, it is preferred that at least about 0.25 μg of the viral genome is combined with about 1 μg of the vector, more preferably about 0.25 to about 0.5 μg or greater of viral genome per 1 μg amount of vector. The viral genome can be obtained from serum or infected cells. The isolated virus may be high titer virus and/or concentrated to achieve the amount of viral genome necessary for ligation. In some embodiments, the parvovirus B19 isolated from a sample and used to prepare the clone is present in the sample at about $10^8$ to about $10^{14}$ genome copies/ml of original sample, more preferably about $10^8$ to about $10^{12}$ genome copies/ml of original sample. Virus can be concentrated from serum or infected cells using standard methods known in the art, such as for example, velocity and/or equilibrium density centrifugation using sucrose solutions in low-salt buffer. Preferably, viral genome is concentrated at about $10^8$ to about $10^{14}$ genome copies/100 μl of physiological solution, more preferably about $10^8$ to about $10^{12}$ genome copies/100 μl of physiological solution.

The infectious clone is preferably stable and can be passaged through bacterial cell culture without loss of functional ITRs. The stability can be determined by introducing the infectious clone into bacterial cells and subcloning and religating several times. In preferred embodiments, the clone can be passaged in bacterial cells at temperatures ranging from about 30° C. to about 37° C. at least about 10 times without substantial loss of ITR nucleic acid sequence.

C. Recombinant Methods, Vectors, and Host Cells

The infectious B19 clones of the invention are produced by synthetic and recombinant methods. Accordingly, the invention relates to polynucleotides encoding the infectious B19 clones of the invention (such as for example a B19 genome) and host cells containing the infectious clone, as well as methods of making such vectors and host cells by recombinant methods.

The B19 clones of the invention may be synthesized or prepared by techniques well known in the art. Some nucleotide sequences for parvovirus B19 genomes are known and readily available, for example, on the Internet at GenBank (accessible at www-ncbi-nlm-nihgov/entrez). The nucleotide sequences encoding the B19 clones of the invention may be synthesized or amplified using methods known to those of ordinary skill in the art including utilizing DNA polymerases in a cell free environment.

The B19 clones of the invention can be produced from viral isolated obtained from biological samples. The polynucleotides may be produced by standard recombinant methods known in the art, such as polymerase chain reaction (Sambrook, et al., 1989, Molecular Cloning, A Laboratory Manual, Vols. 1-3, Cold Spring Harbor Press, Cold Spring Harbor, N.Y. Methods of altering or modifying nucleic acid sequences are also known to those of skill in the art.

As described herein in the methods of the invention, the B19 genome may be assembled from polymerase chain reaction cassettes sequentially cloned into a vector containing a selectable marker for propagation in a host. Such markers include dihydrofolate reductase or neomycin resistance for eukaryotic cell culture and tetracycline or ampicillin resistance genes for culturing in *E. coli* and other bacteria.

The polynucleotide may be inserted into a replicable vector for cloning (amplification of the DNA) as described in the methods herein. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques that are known to the skilled artisan.

Examples of suitable replicable vectors include, without limitation, pCR-Blunt II TOPO vector (Invitrogen, San Diego, Calif.), pProEX Htb vector (Invitrogen, San Diego, Calif.), and pBR332 (Deiss et al., 1990, *Virology,* 175:247-254), and pBluescipt SK. The polynucleotide can be operably linked to an appropriate promoter such as, for example, the parvovirus B19 p6 promoter. Additional suitable promoters are known in the art such as SV40 or CMV. The replicable vectors may further contain sites for transcription initiation, transcription termination, and a ribosome binding site for translation.

In an embodiment, the full length B19 genome is cloned by digesting the genome with a restriction enzyme that cuts the genome into two fragments, cloning the two fragments, and religating the two fragments to form the full-length genome. The B19 genome may be digested, for example, with BamHI. The two fragments (right end genome fragment and left end genome fragment) generated by BamHI digestion are ligated into separate BamHI-StuI digested pProEX HTb vectors (Invitrogen-Life Technologies). See, for example, FIG. 3. To reduce the vector size and eliminate undesired restriction sites, clones that contain the right end of the genome (pB19-42d6) may be digested with EcoRV and religated. The full-length genome is generated by digesting the plasmid containing the left end genome fragment (pB19-44) with BamHI and Ecl136II and cloning the fragment containing the left end genome fragment into the BamHI/EheI site of the pB19-42d6 plasmid (FIGS. 3 and 4).

Introduction of a recombinant vector comprising a B19 genome into a host cell, such as for example a bacterial cell or eukaryotic cell, can be affected by calcium phosphate transfection, DEAE-dextran mediated transfection, cationic lipid-mediated transfection, electroporation, electrical nuclear transport, chemical transduction, electrotransduction, infection, or other methods. Such methods are described in standard laboratory manuals such as Sambrook, et al., 1989, Molecular Cloning, A Laboratory Manual, Vols. 1-3, Cold Spring Harbor Press, Cold Spring Harbor, N.Y. or Davis et al., 1986*, Basic Methods in Molecular Biology*. Commercial transfection reagents, such as Lipofectamine (Invitrogen, Carlsbad, Calif.) and FuGENE 6™ (Roche Diagnostics, Indianapolis, Ind.), are also available. Preferably transfection efficiency of the host cells is about 15% or greater, more preferably about 20% or greater, more preferably about 30% or greater, more preferably about 40% or greater, more preferably about 50% or greater, more preferably about 70% or greater In an embodiment, eukaryotic cells are transfected with an electric current. Methods of transfecting eukaryotic cells utilizing an electric current are known in the art, such as for example, electroporation (Sambrook, et al., 1989, Molecular Cloning, A Laboratory Manual, Vols. 1-3, Cold Spring Harbor Press, Cold Spring Harbor, N.Y. or Davis et al., 1986*, Basic Methods in Molecular Biology*) and electrical nuclear transport (U.S. 20040014220).

In an embodiment, a eukaryotic cell is transfected by electrical nuclear transport. The permissive cells are exposed to an electrical pulse comprising a field strength of about 2 kV/cm to about 10 kV/cm, a duration of about 10 μsec to about 200 μsec, and a current of at about 1 A to about 2.5 A followed by a current flow of about 1 A to about 2.5 A for about 1 msec to about 50 msec. A buffer suitable for use in electrical nuclear transport comprises 0.42 mM $Ca(NO_3)_2$, 5.36 mM KCl, 0.41 mM $MgSO_4$, 103 mM NaCl, 23.8 mM $NaHCO_3$, 5.64 mM $Na_2HPO_4$, 11.1 mM d(+) glucose, 3.25 μM glutathione, 20 mM Hepes, and pH 7.3. Following transformation, the permissive cells may be incubated for about 10 min at 37° C. before being plated in prewarmed (37° C.) culture medium with serum and incubated at 37° C.

Commercially available devices and buffer systems for electrical nuclear transport, such as for example the AMAXA CELL LINE NUCLEOFECTOR™ system (Amaxa Biosystems Inc., Nattermannallee, Germany; www-amaxa-com), have been customized to transduce specific types of eukaryotic cells such as, for example, UT7/Epo cells UT7/Epo-S1 cells. In an embodiment, UT7/Epo cells or UT7/Epo-S1 cells are transfected using NUCLEOFECTOR™ reagent R and program T-20 on the NUCLEOFECTOR™ device according to the manufacturer's instructions (Amaxa Biosystems Inc., Nattermannallee, Germany).

D. Uses

The infectious clone and methods described herein can be utilized in a variety of assays and to develop therapeutic products. As discussed previously, methods for consistently obtaining infectious virus in cell culture were not previously known. An in vitro system for producing infectious virus particles can be used in screening methods to identify agents such as antibodies or antisense molecules that can inhibit viral infectivity or reproduction. The infectious virus and/or infectious virus in a host cell can be utilized to form immunogenic compositions to prepare therapeutic antibodies or vaccine components. Antibodies and primers can be developed to specifically identify different parvovirus B19 isolates. The ability to produce infectious virus consistently in vitro is also useful to produce attenuated virus that may be used in a vaccine.

The infectious B19 clones of the invention are useful in diagnostic assays. The presence or absence of an antibody in a biological sample that binds to a B19 clone of the invention can be determined using standard methods. Alternatively, the presence or absence of B19 parvovirus in a biological sample can be determined can be determined using PCR primers specific for nucleic acids encoding an infectious clone of the invention to amplify any parvovirus B19 DNA that may be present in the sample. Several primers have been described in the Examples. The primers and antibodies can be developed to specifically identify different viral isolates based on difference in nucleic acid or protein sequences.

The infectious B19 clones of the invention are also useful to produce antibodies to parvovirus B19. The antibodies are useful in diagnostic assays for detecting the presence of parvovirus B19 in a biological sample. Methods for developing antibodies are described below. One aspect of the invention provides a method for screening for parvovirus B19 infection, comprising contacting a biological sample with an anti-parvovirus B19 antibody and assaying the biological sample for anti-parvovirus B19 antibody binding. The antibodies, preferably recognize a particular isolate.

The invention also provides methods for screening for antibodies that may inhibit or antagonize B19 infection of permissive cells. The antagonist effect of anti-parvovirus B19 antibodies may determined by analyzing cells for B19 capsid proteins or B19 spliced capsid transcripts as described above. Antagonist antibodies can be prepared and screened as described below.

The infectious parvovirus B19 clone and/or host cells comprising the clone can be used as immunogenic compositions to prepare vaccine components and/or to develop antibodies that can be used in diagnostic or other assays. For example, host cell cultures comprising the parvovirus B19 clone can be heat inactivated and used as an immunogen. Passaging of an infectious clone in vitro can provide an attenuated strain of parvovirus B19 useful in vaccine compositions.

E. Production of Antibodies

1. Polyclonal Antibodies

Polyclonal antibodies to infectious B19 clones of the invention of the invention are preferably raised in animals by multiple subcutaneous (sc) or intraperitoneal (ip) injections of the relevant antigen and an adjuvant. The relevant antigen may be, for example, one or more B19 clones of the invention or one or more B19 proteins, such as NS, VP1, VP2, 11-kDa protein, 7.5-kDa protein, and/or protein X, derived from an infectious clone of the infection. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ½ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

In an alternative embodiment, the animals are immunized with a recombinant adenovirus vector expressing one or more viral proteins derived from an infectious clone of the invention, such as for example VP1 and/or VP2, followed by booster immunizations with the viral proteins. The polyclonal antibodies generated by the immunizations may undergo a screen for B19 antagonist activity. Preferably, antibodies to an infectious B19 clone of the invention inhibit the negative effect of B19 on erythocyte production. In an embodiment, antibodies that specifically bind a B19 clone encoded by a polynucleotide comprising a nucleic acid sequence of SEQ ID NO:5 inhibits infection of permissive cells.

The polyclonal antibodies are also screened by enzyme-linked immunoabsorbent assay (ELISA) to characterize binding. The antigen panel includes NS, VP1, VP2, 11-kDa protein, 7.5-kDa protein, and protein X. Animals with sera samples that test positive for binding to one or more experimental antigens in the panel are candidates for use in monoclonal antibody production. The criteria for selection for monoclonal antibody production is based on a number of factors including, but not limited to, binding patterns against a panel of B19 viral proteins.

2. Monoclonal Antibodies

Monoclonal antibodies to an infectious B19 clone of the invention may be made using the hybridoma method first described by Kohler et al., *Nature,* 256:495 (1975), or may be made by recombinant DNA methods (U.S. Pat. No. 4,816, 567).

In the hybridoma method, a mouse or other appropriate host animal, such as a hamster or macaque monkey, is immunized as described above to elicit lymphocytes that produce or are capable of producing antibodies that will specifically bind to a B19 clone of the invention or viral proteins derived from a B19 clone of the invention used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells are than seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen and HIV Env. Preferably, the binding specificity of monoclonal antibodies produced by hybridoma cells is determined by immunoprecipitation or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The monoclonal antibodies are characterized for specificity of binding using assays as described previously. Antibodies can also be screened for antagonist activity as described previously.

3. Human or Humanized Antibodies

Humanized forms of non-human (e.g., murine) antibodies are chimeric antibodies that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, rabbit or nonhuman primate having the desired specificity, affinity, and capacity.

Useful non-human antibodies are monoclonal antibodies that bind specifically to parvovirus B19. Useful non-human antibodies also include antibodies that inhibit B19 infection of permissive cells. In some instances, framework region (FR) residues of the human immunoglobulin are replaced by corresponding non-human residues. Furthermore, humanized antibodies may comprise residues that are not found in the recipient antibody or the donor antibody. These modifications may be made to improve antibody affinity or functional activity. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech* 5:428-433 (1994).

Human antibodies that specifically bind and/or antagonize parvovirus B19 can also be made using the transgenic mice available for this purpose or through use of phage display techniques.

An in vitro system for producing infectious virus particles can be used in screening methods to identify agents such as antibodies or antisense molecules that can inhibit viral infectivity or reproduction. A screening method comprises introducing the viral genome of an infectious clone of parvovirus B19 into a cell and contacting the cells with a potential inhibitory agent, and determining whether the inhibitory agent inhibits infectivity or replication of the viral genome in the cells. Methods for detecting infectivity and replication of the viral genome have been described herein. Potential inhibitory agents include antibodies and anti sense molecules.

The ability to produce infectious parvovirus in vitro may allow for the development of a vaccine or vaccine components. A vaccine can be comprised of heat inactivated virus or attenuated virus. Inactivated virus can be prepared from production of infectious clones using methods known to those of skill in the art. Attenuated virus can be obtained by serially passaging the virus under conditions that make the virus non pathological to humans. The attenuated virus is preferably passaged through a cell and under certain conditions that provide for an altered virus that is less pathological to humans. Vaccine components can also include one or more of the parvovirus proteins or parvovirus proteins combined with epitopes from other infectious agents.

All publications, patents, and patent applications cited herein are hereby incorporated in their entirety by reference. The following examples are provided for illustrative purposes only, and are in no way intended to limit the scope of the present invention.

Example 1

Cloning and Sequencing of Parvovirus B19 Isolate J35

Introduction

The nucleotide sequence of B19 was originally established by sequencing a viral isolate designated pvbaua obtained from the serum of a child with homozygous sickle cell disease (Shade et al. 1986, *J. Virol.,* 58: 921-936). Subsequently, many B19 isolates have been sequenced by multiple methods (Erdman et al. 1996, *J. Gen. Virol.,* 77: 2767-2774). Following alignment of the sequences, there is a 6% divergence amongst the various isolates (Heegaard & Brown, 2002, *Clin. Microbiol. Rev.,* 15: 485-505). The single nonstructural protein (NS1) gene is highly conserved, and the two capsid proteins, VP1 and VP2, occasionally have a greater variability of 2-3% (Hemauer et al. 1996, *J. Gen. Virol.,* 77: 1781-1785; Mori et al. 1987, *J. Gen. Virol,* 68: 2797-2806).

There is no animal model for B19, and virus can only be grown in culture with difficulty (Heegaard & Brown, 2002). Parvovirus B19 exhibits a selective tropism for erythroid progenitor cells, and can only be cultured in primary erythroid progenitor cells from bone marrow, blood, or fetal liver cells, megakaryoblast cells, UT7/Epo cells, UT7/Epo-S1 cells, KU812Ep6 cells, JK-1 cells, and MB-O2 cells. (Ozawa et al., 1986; Brown et al., 1991; Yaegashi et al., 1989; Komatsu et al., 1993; Shimomura et al.; 1992 Miyagawa et al., 1999). These series of examples establish a method of producing an infectious clone for parvovirus B19.

Methods

Parvovirus B19 (J35) was obtained from the serum of a child with sickle cell anemia undergoing aplastic crisis and sent to NIH for diagnostic purposes. The serum was found by dot blot assay (Nguyen et al., 2002) to contain approximately $10^{12}$ genome copies of B19/mL. UT7/Epo-S1 cells (Shimomura et al., 1992) (maintained in Iscove's modified Dulbecco's medium (IMDM) containing 10% fetal calf serum, 2 U/ml recombinant human erythropoietin (Amgen, Thousand Oaks, Calif.), and antibiotics at 37° C. in 5% $CO_2$) were infected with the J35 serum containing high titer B19 virus (Nguyen et al., 2002). DNA was extracted by the DNeasy® method (Qiagen Inc, Valencia, Calif.) and eluted into 100 μl of water.

To obtain the coding region of B19 genome, the primer B19-187FR (CGCTTGTCTTAGTGGCACGTCAAC) (SEQ ID NO:16) was designed from the hairpin region of the virus using sequences available in GenBank (19-HV; AF162273) (SEQ ID NO:17). High fidelity long PCR amplification was performed using the single primer B19-187FR with the HF-2 polymerase kit (BD Biosciences, Palo Alto, Calif.) with 25 cycles of amplification (94° C., 15 s; 55° C., 30 s; 72° C. 4 min; followed by 72° C. extension for 7 min). The amplicon was cloned by blunt ligation into a pCR-Blunt II TOPO® (Invitrogen, San Diego, Calif.) and transformed into One Shot® Top 10 competent *E. coli* cells (Invitrogen, San Diego, Calif.).

Colonies were screened by hybridization with a $^{32}$P-random-primed B19 probe obtained from pYT103 as previously described for dot blot hybridization (Nguyen et al., 2002), and positive clones were confirmed by sequencing the plasmids using BigDye® terminator cycle sequencing (ABI-Perkin Elmer, Foster City, Calif.). The full-length sequences of both strands were obtained by primer walking.

To obtain the complete hairpin sequence, primers (Table 1) were designed from the cloned sequence and from B19 sequences available in GenBank. PCR amplification was performed using ExTaq polymerase with 30 cycles of amplification. The PCR products were ligated into PCR2.1 TOPO® by TA Cloning® (Invitrogen-Life Technologies), Top10 cells transformed, and the products sequenced as above.

All DNA sequences, and the amino acid sequence of open reading frames, were analyzed using Lasergene® software (DNAStar, Inc., Madison, Wis.). DNA pairwise homology was determined by Lipman-Pearson method with a Ktuple of 2, gap penalty of 4, and deletion penalty of 12. Multiple sequence alignments were determined using the MegAlign program, using the Clustal method with a gap penalty of 10 and gap length penalty of 10.

TABLE 2

List of primer pairs used for PCR

| SEQ ID No. | Primer | Nucleotide Sequence (5'-3') | Product (bp) |
|---|---|---|---|
| 18 | B19-1F | CCACGATGCAGCTACAACTT | |
| 19 | B19-186R | GTGAGCGCGCCGCTTGTCTTAGTG | 186 |
| 20 | B19-181F | GTGAGCGCGCCGCTTGATCTTAGT | |
| 21 | B19-1372R | AACTTCCACTGTGACTACTG | 1195 |
| 22 | B19-181F | GTGAGCGCGCCGCTTGATCTTAGT | |
| 23 | B19-4899F | AACACCACAGGCATGGATAC | 518 |

Discussion

The complete B19 coding region, including half of each ITR, was amplified using PCR. Although several plasmids containing the B19 genome were obtained, only one clone, obtained using the primer B19-187FR, did not contain deletions. This plasmid, designated as pB19-N8 (FIG. 1), was sequenced, and contained a 4844-nucleotide sequence including the entire coding region, and 177 nucleotides of the ITR. The nucleotide sequence of this B19 isolate (J35) had 99.1% identity to that of B19-Au isolate (GenBank M13178) (SEQ ID No:24). The putative NS, VP1 and VP2 capsid proteins had 99.4%, 99.4% and 99.6% homology respectively, at the amino acid level compared to the B19-Au isolate.

The 135 isolate of B19 has a genome of 5592 nucleotides, possessing ITRs of 381 nucleotides in length. The distal 361 nucleotides of these repeats were imperfect palindromes that form double-stranded hairpins. This normally exist in two sequence orientations, "flip" or its reverse-complement "flop", believed to result from hairpin transfer during replication (Deiss et al., 1990).

The complete sequence analysis of the viral genome (J35) indicates that both the 5' and 3' ITRs have two sequence configurations (SEQ ID NO:1 and SEQ ID NO:2) analogous to the flip and flop formats previously reported by Deiss et al. (1990) (FIGS. 2A and 2B; SEQ ID NO:3 and SEQ ID NO:4). Although several base changes within the ITRs were identified compared to the previous published sequence of B19 (Deiss et al., 1990), the size and the positions of the bubbles formed by unpaired nucleotides in these palindromic sequences are conserved among different B19 isolates, suggesting an important role of these structures in the life cycle of B19 virus. In comparison to the previously reported B19 sequence, the hairpin of B19-J35 isolate was shorter by two nucleotides at both 5' and 3' ends, but this deletion does not appear to affect viral replication and infection. Unlike other parvoviruses, the hairpins of B19 do not appear to form a Y- or T-shape structure at the turnaround.

Example 2

Construction of B19 Clones

Introduction

There has only been one previous report of the intact ITRs of the human pathogenic parvovirus B19 (Deiss et al., 1990). In Deiss et al., the genome was cloned in two halves, and the sequence of the ITRs obtained. However, Deiss et al. were not unable to successfully ligate the two halves of the genome together nor could they confirm that the ITRs were correct by functional studies. Other attempts to produce an infectious clone were also unsuccessful due to deletions in the ITR sequences (Shade et al., 1986) and the instability of the ITRs in bacterial cells. Our attempts to construct a full-length clone by ligating the ITR sequences to pB19-N8 were repeatedly unsuccessful.

In the present examples, we successfully clone the full-length B19 genome using low incubation temperatures and Sure®2 competent *E. coli* cells (Strategene, La Jolla, Calif.) that are deficient in major recombination genes. B19 packages equal numbers of both positive and negative DNA strands (Summers et al., 1983) and has a unique BamHI restriction enzyme site in the genome (Cotmore & Tattersall, 1984). These properties were used to clone the full-length B19 genome in two halves (FIG. 3). We also tested whether the full-length B19 genome, especially the ITR sequences, would be stable in the plasmid backbone during the multiple steps of molecular cloning experiments.

Methods

B19 DNA was purified from 50 μl of viremic serum (J35) using the High Pure® Viral Nucleic Acid Kit (Roche, Indianapolis, Ind.) to obtain approximately 1.5 μg of double stranded B19 DNA. Double stranded viral DNA (0.5 μg) was digested with BamHI and both resulting fragments were ligated into BamHI-StuI digested pProEX HTb vector (Invitrogen-Life Technologies). The ligated products were electroporated into electrocompetent Sure®2 *E. coli* cells (Stratagene) using a BTX electroporator, then the bacteria were immediately plated and incubated overnight at 30° C. The resultant colonies were screened for inserts. To reduce the vector size and eliminate undesired restriction sites, clones that contained the right end of the genome were digested with EcoRV and religated (pB19-42d6). The insert of the plasmid, together with the insert of the left end containing plasmid (pB19-44) was completely sequenced. To create full-length clones, pB19-44 was digested with BamHI and Ecl136II and the fragments containing the left end of the genome were cloned into the BamHI/EheI site of the pB19-42d6 plasmid resulting in pB19-4244 (FIG. 4).

To test the stability of the plasmid containing full-length B19 genome, pB19-4244 was digested with BamHI and religated, and then transformed into Sure®2 cells. After incubation at 30° C. overnight, 18 colonies were picked up from the plates and the bacteria were propagated at 30° C. The plasmids were purified and mapped by restriction digestion with HindIII, BssHII, and SalI. The fragments were then analyzed by agarose-electrophoresis.

Discussion

Figure 2A:
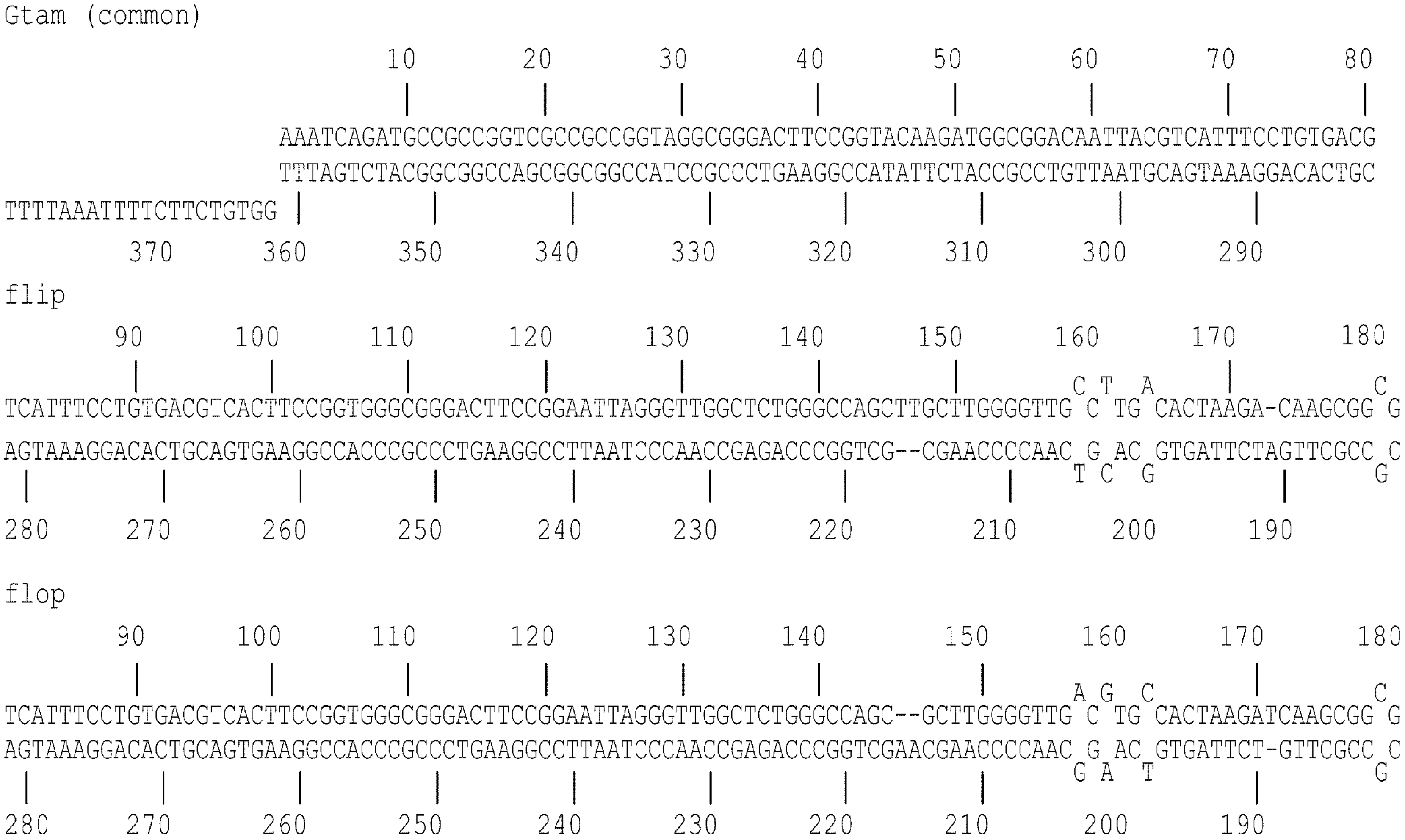
FIG. 2A shows the structure of the B19 terminal inverted repeats in hairpin form. The "flip" (SEQ ID NO:1) and "flop" (SEQ ID NO:2) orientations at the 5' end (+ strand) are shown.

Of the 192 clones that were analyzed, 5 contained the untruncated 5' end of the genome, and 2 clones contained the untruncated 3' end of the genome. All the untruncated clones had the same "flip" format for their ITRs (FIGS. 2A and 2B).

After ligation of the plasmids together, two identical clones consisting of the full-length B19 genome were selected and designated as B19-36 and pB19-4244; GenBank AY386330; SEQ ID NO: 25 (FIG. 4). These full-length clones were sequenced and the sequences of inserts showed 100% identity to the corresponding region in the pB19-N8. The full viral genome was 5592 nucleotides long, with terminal repeat sequences of 381 nucleotides that formed an imperfect palindrome. In comparison to the previously published sequences (Deiss et al., 1990), and the one unpublished sequence in GenBank (B19-HV; AF162273) (SEQ ID NO:17), there were two less nucleotides at the start and end of the genome, resulting in a palindromic sequence of 361. As showed in FIG. 2B, the nucleotide sequences of the flip and flop are slightly different from that reported by Deiss et al. (1990) but the numbers and positions of the unpaired nucleotides in these palindromic sequences are conserved among the two different B19 isolates.

We tested whether the full-length B19 genome, especially the ITR sequences, were able to be stabilized in the plasmid backbone during the multiple steps of molecular cloning experiments. The plasmid pB19-4244 was digested with BamHI and religated, and then transformed into Sure®2 cells. After incubation at 30° C. overnight, 18 colonies were picked up from the plate for purification and mapping by restriction digestion. All of the plasmids tested (18/18) had the correct restriction sites, and there were no deletions in the hairpin sequences. The plasmids were serially passed and then sequenced to confirm the absence of deletions in the hairpin sequences. We found no evidence of deletions under the conditions used in the present study.

Example 3

Introduction of Mutations into a B19 Infectious Clone

Introduction

As an experimental control, a second infectious clone was produced. This clone was generated to have the same nucleotide sequence as plasmid pB19-4244, except for a single nucleotide substitution to confirm that the infectious clone could generate infectious virus. The production of an infectious clone and the ability to manipulate the plasmid will allow the genome to be studied more systematically.

Method

Figure 5:
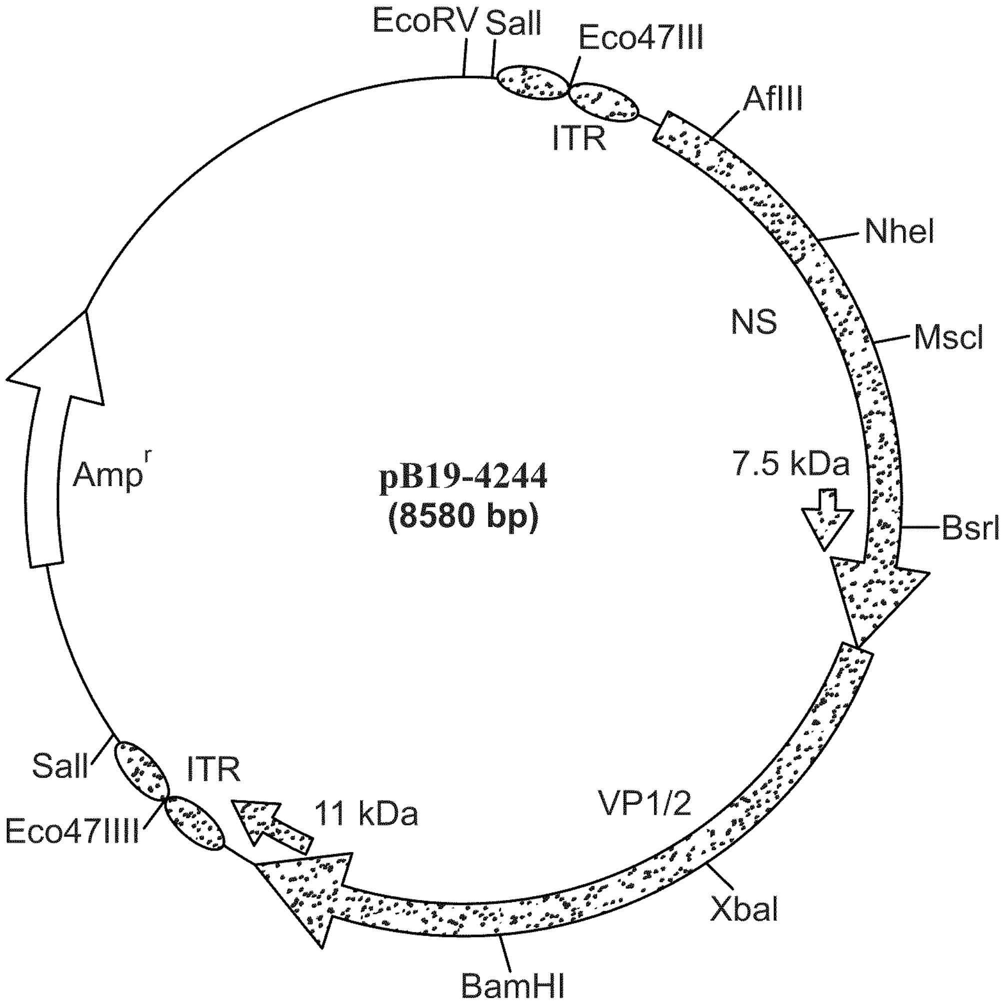
FIG. 5 shows a map of recombinant plasmid pB19-4244d. The arrows indicate genes. The shaded circles at the 5' and 3' ends of the B19 genome indicate the ITR sequences. Shaded arrows indicate genes in the B19 genome. Plasmid pB19-4244d was modified from pB19-4244 by XhoI-Ecl36II digestion to remove the undesired XbaI site.
Figure 6:
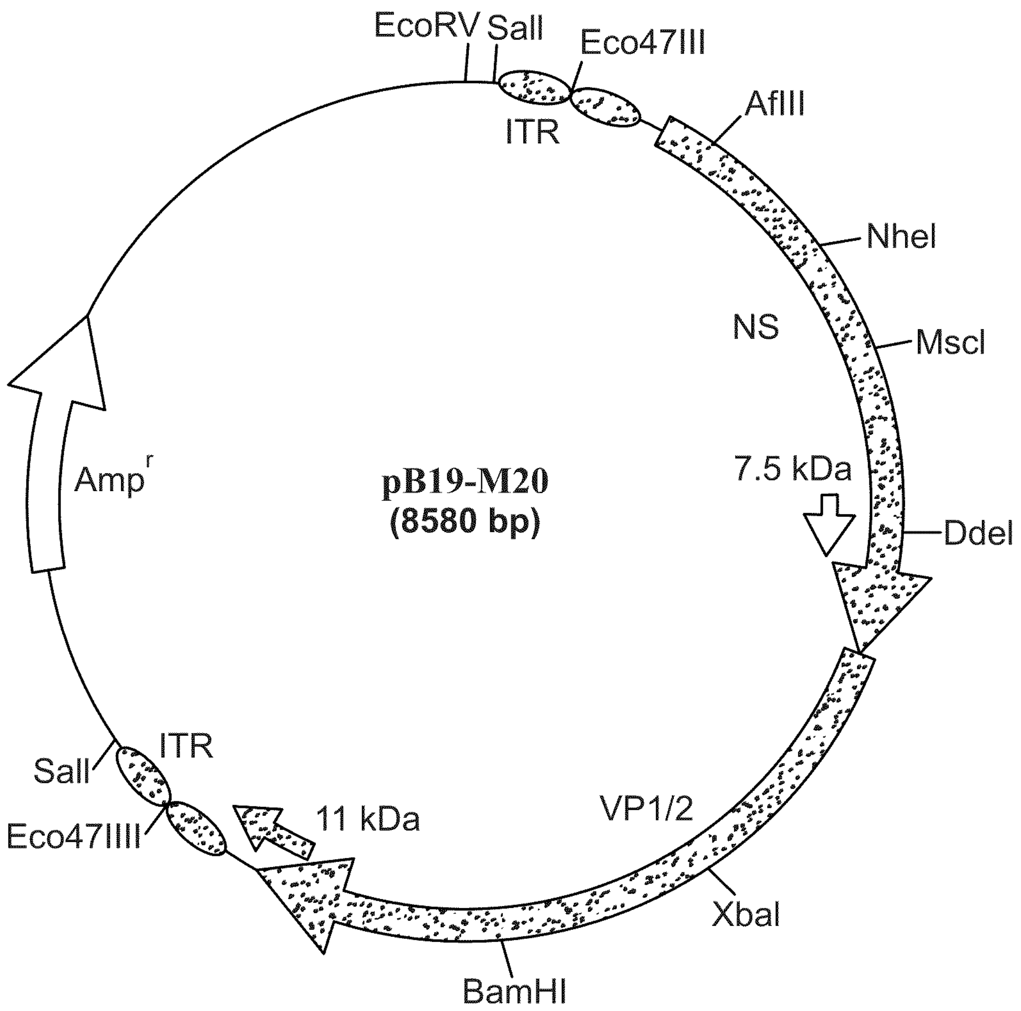
FIG. 6 shows a map of recombinant plasmid pB19-M20. The arrows indicate genes. Shaded arrows indicate genes in the B19 genome. The shaded circles at the 5' and 3' ends of the B19 genome indicate the ITR sequences. Nucleic acid residue 2285 was substituted (C2285T) generating a DdeI site in the B19 genome.

A second infectious clone was produced by site directed mutagenesis. The cytosine at position 2285 (B19-J35 isolate) was replaced with a thymine to generate a recognition site for restriction enzyme DdeI to produce a naturally existing variant of B19 (B19-Wi isolate, GenBank M24682; SEQ ID NO:26). The full-length plasmid pB19-4244 was cut with NheI and the 5' overhang filled in using T4 polymerase. The linearized plasmid was redigested with XbaI, the B19 fragment (from nucleotide 1247 to 3423 in the genome of B19-J35 isolate) ligated into an XbaI-Ecl136II-digested pBluescriptII® KS+ phagemid vector (Stratagene), and site-specific mutagenesis (C2285T) was performed using the QuikChange® Site-directed Mutagenesis Kit (Stratagene) and primers CMCf (CATTTGTCGGAAGCTCAGTTTCCTCCGAAG; SEQ ID NO:27) and CMCr (CTTCGGAGGAAACTGAGCTTCCGACAAATG; SEQ ID NO:28). To eliminate an undesired XbaI restriction site in the vector sequence of the plasmid pB19-4244, the plasmid was digested with Ecl136 II-XhoI enzymes, the XhoI overhang was blunted with T4 polymerase, and the plasmid was religated (plasmid pB19-4244d, FIG. 5). The plasmid with the B19 fragment containing C2285T mutation was digested with MscI-XbaI and the B19 fragment was ligated into the MscI-XbaI digested pB19-4244d plasmid resulting the pB19-M20 clone (FIG. 6).

Discussion

Although the cloned sequence was 99% identical to the B19-Au sequence, it was observed that there was a single nucleotide difference between the J35 sequence (and B19-Au) and the published sequence of another isolate B19-Wi (GenBank M24682) that would convert a BsrI site in J35 to a DdeI site. This site was within the RT-PCR product amplified with the primer pair of B19-2255 and B19-2543 and could potentially be used to distinguish transcripts, and hence, viruses with the different sequence. We therefore constructed a second plasmid, pB19-M20 (FIG. 6), that contained the identical full-length clone, but in which the cytosine at the nucleotide of 2285 was replaced by thymine (C2285T).

Example 4

Figure 7:
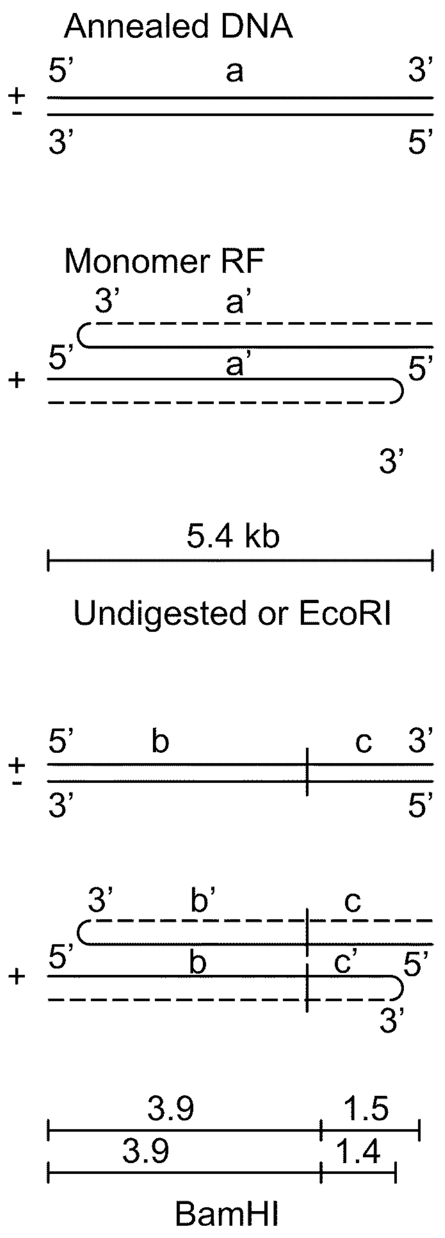
FIG. 7 shows a schematic representation of the replication of B19 viral genome. The replicative DNA form provides evidence of viral DNA replication and can be distinguished by BamHI restriction enzyme digestion.

Infection of Cells with B19 and Detection of Replicative Forms of B19 in Infected Cells Introduction During the replication of parvovirus B19, the viral single-stranded DNA is converted to a double-stranded replicative form which has either an “extended” or a “turnaround” form at the terminal regions. These intermediate structures provide evidence for viral DNA replication and can be distinguished by BamHI restriction enzyme digestion (Cotmore & Tattersall, 1984) (FIG. 7).

To test whether the B19 genome inserted in pB19-4244 could be excised from the flanking vector sequences and produce progeny viral DNA, we compared Southern blot analysis of the DNA purified from the cells transfected with either plasmids cut with SalI enzyme (which releases the full-length B19 genome from the plasmid, FIG. 4) or intact plasmids. Additionally, RT-PCR was used to detect transcripts for viral capsids in RNA recovered from transfected cells. The presence or absence of B19 capsid proteins was detected via immunofluorescent microscopy. By these experimental methods, the presence, transcription, and expression of the capsid gene could be confirmed.

Method

The conditions and reagents for transfecting plasmid DNA into UT7/Epo-S1 cells were first optimized using the plasmid pEGFP-F (BD Biosciences, Palo Alto, Calif.) that encodes farnesylated enhanced green fluorescent protein (EGFP). Cells were examined at daily intervals for expression of EGFP by UV microscopy and by FACS analysis. Conditions that gave the maximum number of cells expressing EGFP with minimum cytotoxicity were chosen. For subsequent experiments UT7/Epo-S1 cells were transfected using the AMAXA® Cell Line Nucleofector™ kit R according to manufacture's instruction (AMAXA Biosystems Inc., Nattermannallee, Germany). The cells were harvested at various times posttransfection and used for DNA, RNA, and immunofluorescence studies. For infection studies, cells were harvested at 72 h posttransfection, washed free of inoculums using fresh culture medium, and cell lysate prepared by three cycles of freeze/thawing. After centrifugation at 10,000 g for 10 min, the clarified supernatant was treated with RNase (final concentration of 1 U/μl, Roche Applied Science, Indianapolis, Ind.) and collected for further infections.

Total RNA was extracted from the UT7/Epo-S1 cells ($2\times10^5$) using RNA STAT60™ (Tel-Test Inc., Friendswood, Tex.). Residual DNA was removed by DNAse I treatment (final concentration, 90 U/ml) for 15 min at room temperature. RNA was converted to cDNA with random hexamers and SuperScript™ II (Invitrogen), and RT-PCR for the spliced capsid transcripts was performed with primers B19-1 (5'GTTTTTTGTGAGCTAACTA3'; SEQ ID NO:6) and B19-9 (5'CCACGATGCAAGCTACAACTT3; SEQ ID NO:7) as described in (Nguyen et al., 2002).

To exclude the possibility that the transcripts detected were derived from laboratory contamination of B19 viral RNA, the cDNA derived from the pM20-transfected cells were PCR amplified by using a primer pair of B19-2255 (GGAACCAGTTCAGGAGAATCA; SEQ ID NO:8) and B19-2543 (TGGCAGCTACATCGCACCAA; SEQ ID NO:9), which annealed proximal to the region containing the site of mutagenesis (C2285T). After purification using QIAquick® PCR Purification Kit (Qiagen Inc., Valencia, Calif.), the PCR products were digested with DdeI at 37° C. for 2 h.

Immunofluorescence. Infected or transfected cells were harvested and cytocentrifuged (1500 rpm for 8 mins in a Shandon cytospin 2 cytocentrifuge). The cells were fixed in acetone:methanol (1:1) at −20° C. for 5 min, washed twice in phosphate buffered saline (PBS) containing 0.1% fetal bovine serum, and incubated with a murine anti-B19 capsid protein monoclonal antibody (521-5D, gift of Larry Anderson, CDC) in PBS with 10% fetal calf serum for 1 hr at 37° C. After washing the slides twice in PBS, the slides were incubated with fluorescein isothiocyanate (FITC)-labeled goat anti-mouse IgG antibody (Jackson ImmunoResearch Laboratories, Inc., West Grove, Pa.) in PBS with 10% fetal calf serum and counterstained with Evans Blue for 30 mins at 37° C., washed in PBS, and examined by UV microscopy.

Southern blot analysis of B19 DNA. DNA was extracted from B19 infected UT7/Epo-S1 cells ($5\times10^5$) as previously described (Shimomura et al., 1992). Briefly, $5\times10^5$ cells were incubated with 100 mM NaCl, 10 mMTris-HCl (pH 7.5), 0.5% sodium dodecylsufate (SDS), 5 mM EDTA, and 200 µg/ml proteinase K overnight at 37° C. followed by phenol-chloroform extraction. For some experiments high and low-molecular weight DNA were separated by the Hirt method (Hirt, 1967). Purified DNA (400 ng) was digested with 20 U of BamH I (single cut in B19) or EcoRI (no cut in B19) at 37° C. for 4 h. The fragments were then separated by agarose-electrophoresis, transferred to a nylon membrane (Nylon+, Amersham), and hybridized with a $^{32}$P-random-primed probe of the complete B19 coding region as previously described (Shimomura et al., 1992).

Discussion

The plasmid pEGFP-F was used to optimize the conditions for transfecting UT7/Epo-S1 cells. Although standard electroporation and liposomes were also tried, the best results were obtained using the AMAXA® Cell Line Nucleofector System™. The highest transfection efficiency (~70%) with minimum cytotoxicity (~20%) was achieved with reagent R and T-20 program using 3 µg pEGFP DNA and $2\times10^6$UT7/Epo-S1 cells, following the manufacturer's instructions (AMAXA Biosystems Inc., Cologne, Germany).

Figure 8:
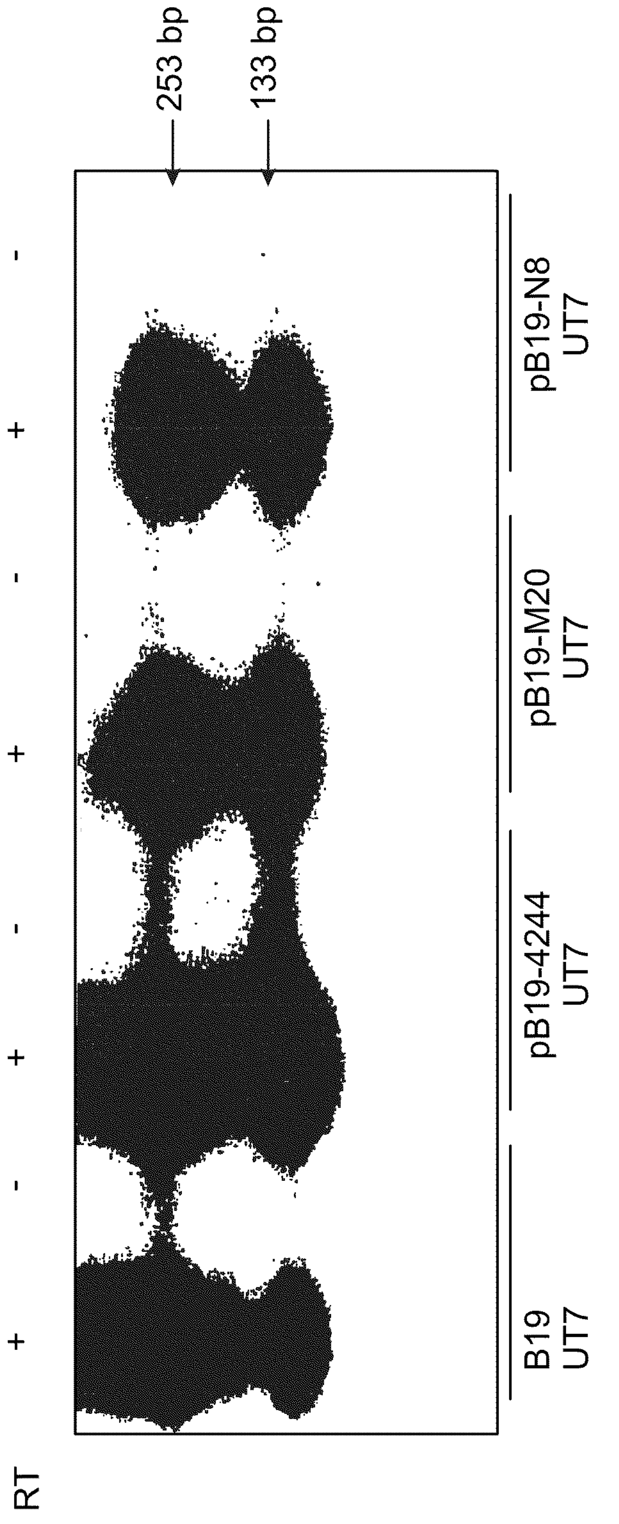
FIG. 8 shows RT-PCR analysis of UT7/Epo-S1 cells for B19 transcripts. The cells were transfected with recombinant plasmids or infected with B19 virus. Total RNA was extracted from the cells 72 h post-transfection or 72 h post-infection. RT-PCR was performed with a primer pair of B19-1 (SEQ ID NO:6) and B19-9 (SEQ ID NO:7). The PCR products were separated by agarose electrophoresis and analyzed by Southern blotting with an alkaline-phosphatase-labeled probe. (+) and (−) indicate the presence or absence respectively of reverse transcriptase in the PCR reaction. The numbers with arrows indicate amplicon size in base pairs (bp).
Figure 9A:
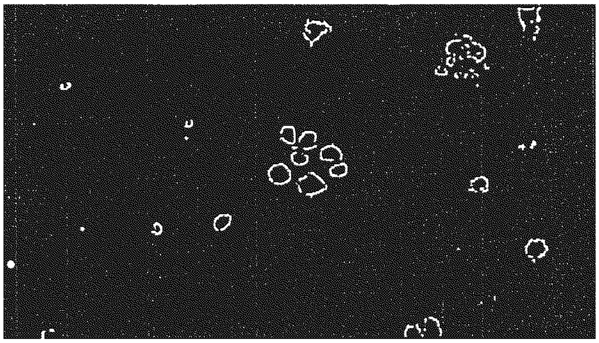
FIGS. 9A-C show detection of B19 capsid proteins in UT7/Epo-S1 cells infected with B19 virus (FIG. 9A), UT7/Epo-S1 cells transfected with pB19-M20 (FIG. 9B), and UT7/Epo-S1 cells transfected with pB19-N8 (FIG. 9C). The B19 capsid proteins were detected 72 h post-transfection or 72 h post-infection using monoclonal antibody 521-5D (gift from Dr. Larry Anderson, Centers for Disease Control and Prevention, Atlanta, Ga.). Magnification is 750×.
Figure 9B:
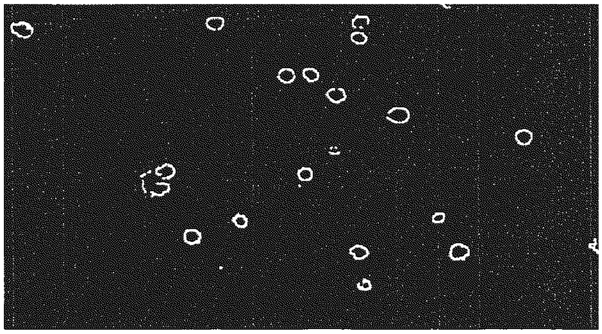
Figure 9C:
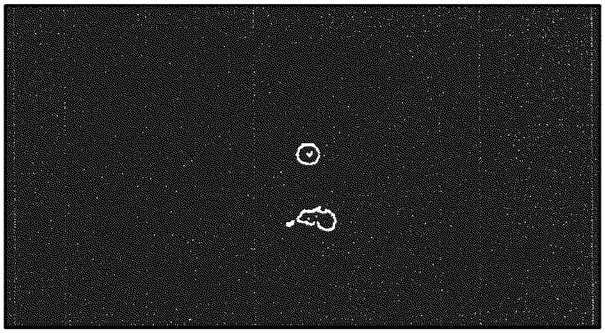

UT7/Epo-S1 cells were transfected with plasmids pB19-4244, pB19-M20, and pB19-N8 under the same conditions, and harvested at 72 h post-transfection. The RT-PCR and immunofluorescence assay were performed to detect the viral spliced transcripts and capsid proteins. After RT-PCR, two amplicons of 253 bp and 133 bp, representing the alternative spliced transcripts of B19 capsid gene, were detected in the cells transfected with either plasmid (FIG. 8). By immunofluorescence assay, B19 capsid protein was also detected in the transfected cells, with approximately 15% of the cells having a positive signal when transfected with pB19-4244 and (FIG. 9B) and 5% with pB19-pN8 (FIG. 9C). There was a significant difference in the number of positive cells between the two different plasmid constructs although the same amount of plasmid DNA was introduced into the cells under identical conditions. Infection with B19 wild-type virus (J35 isolate) gave approximately 20% positive cells (FIG. 9A).

Figure 10:
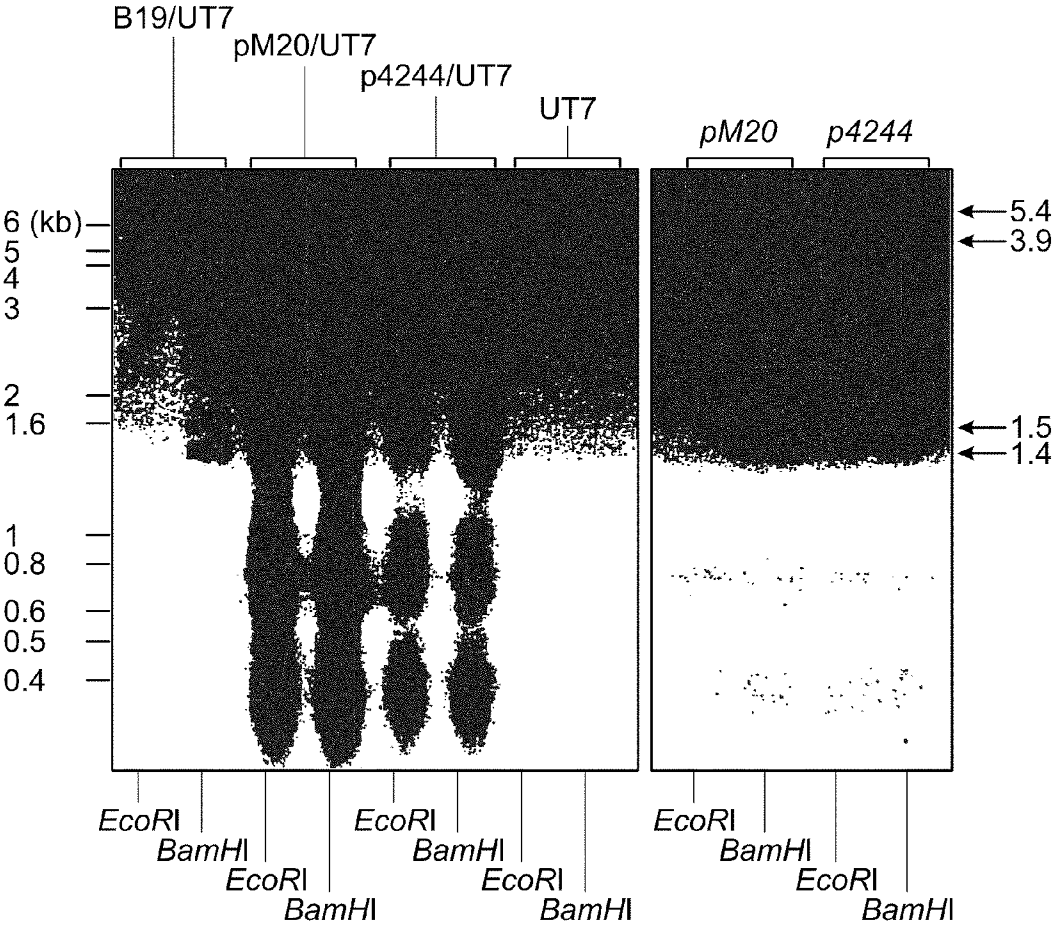
FIG. 10 shows Southern blot analysis of DNA purified from cells transfected with SalI digested fragment of pB19-M20 or pB19-4244. DNA from B19 virus was used as a positive control. The purified DNA was digested with BamHI or EcoRI and the fragments separated by agarose electrophoresis. The fragments were probed with a $^{32}$P-random-primed probed of the complete B19 coding region. Distinct doublets of 1.5 and 1.4 kb were detected in transfected cell samples digested with BamHI, but not in the plasmid controls. The 1.4 kb band is a definitive marker for viral genome replication.
Figure 11:
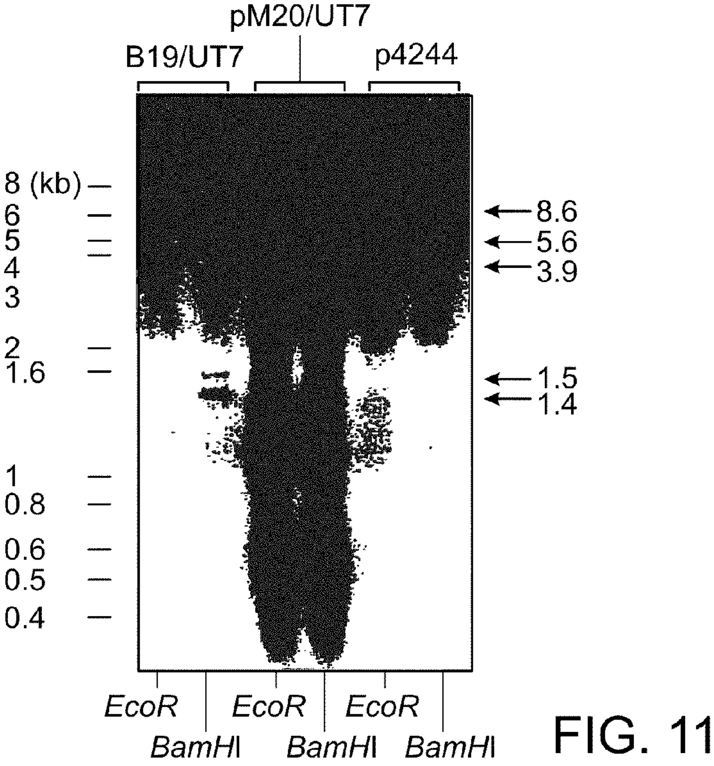
FIG. 11 shows Southern blot analysis of DNA purified from cells transfected with undigested pB19-M20 or pB19-4244. The purified DNA was digested with BamHI or EcoRI and the fragments separated by agarose electrophoresis. The fragments were detected with a $^{32}$P-random-primed probe of the complete B19 coding region. Distinct doublets of 1.5 and 1.4 kb were detected in transfected cell samples digested with BamHI. The 1.4 kb band is a definitive marker for viral genome replication. A band with a molecular size of 5.6 kb, which corresponds to the size of the B19 genome, was also detected in EcoRI digested DNA. The 5.6 kb band indicated that progeny viral DNA was produced by the transfected cells as neither the B19 genome nor the vector contained an EcoRI restriction enzyme site.

At 72 h posttransfection, the DNA was extracted from the cells and incubated with the restriction endonuclease EcoRI (no cuts in the parvovirus B19 genome) or BamHI (a single cut in the parvovirus genome). As in B19 infection of UT7/Epo-S1 cells, distinct doublets of 1.5 kb and 1.4 kb were detected in all the transfected cell samples digested with BamHI, but not in the plasmid controls (FIGS. 10 and 11). Although a portion of the signal for the 4.1 and 1.5 kb bands in FIG. 10 is contributed by the transfected DNA, the 1.4 kb band is a definitive marker for viral genome replication. In addition, a band with a molecular size of 5.6 kb, which corresponds to the size of the viral B19 genome, was detected in EcoRI-digested DNA from the cells transfected with undigested (SalI) plasmid pB19-M20 (FIG. 11). This indicated that viral progeny DNA was produced because neither the B19 genome nor vector contain an EcoRI restriction enzyme site. Although equal amounts of DNA of either SalI-digested plasmid or whole plasmid were introduced into the cells, the band density of the replication intermediates in the sample of SalI-digested fragment appeared to be stronger. This suggested that the replication process was facilitated when the viral genome was released from the vector backbone.

Example 5

Confirmation of B19 Infectious Virus

Introduction

To determine if infectious virus were generated from the UT7/Epo-S1 cells transfected with plasmid pB19-4244 or pB19-M20, the supernatant from the cell lysates was tested for the detection of spliced transcripts of viral capsid genes by RT-PCR. We also performed in vitro neutralization assays to confirm that the infectivity of the cell lysates was mediated by newly synthesized B19 virons. Finally to confirm that the viral transcripts in the inoculated cells were being generated from the infectious clone and not from laboratory contamination of wild type J35 virus, we also used the second infectious clone (pB19-M20) that carried a DdeI site that was present in other B19 isolates but not in J35 virus.

Method

For infection studies, $2\times10^4$ of UT7/Epo-S1 cells in 10 µl IMDM were mixed with an equal volume of sample or positive control (J35 serum diluted to contain $10^8$ B19 genome copies) and incubated at 4° C. for 2 h to allow for maximum virus-cell interaction. The cells were then diluted to $2\times10^5$ cells/ml in the culture medium, and incubated at 37° C., in 5% $CO_2$. Cells were harvested at 3 days post infection and tested for evidence of infection by detection of viral transcripts and protein expression. To determine if infectious virus were generated from the UT7/Epo-S1 cells transfected with plasmid pB19-4244 or pB19-M20, the supernatant from the cell lysates was tested for the detection of spliced transcripts of viral capsid genes by RT-PCR. Plasmid pB19-N8, which does not contain intact ITRs and should not produce infectious virus, was used as a negative control. B19 infected UT7/Epo-S1 cells were used as a positive control.

In vitro neutralization assays were performed to test whether neutralizing monoclonal antibodies against parvovirus B19 capsids were able to block the infection caused by the cell lysates of transfected cells. The clarified cell lysates prepared from the transfected cells were mixed with monoclonal antibody A and E (Yoshimoto et al., 1991) at a dilution of 1:10, and incubated at room temperature for 2 h. The anti-B19 monoclonal antibody A without neutralizing activities was used as control. The infection studies were performed as described above.

Discussion

Figure 12A:
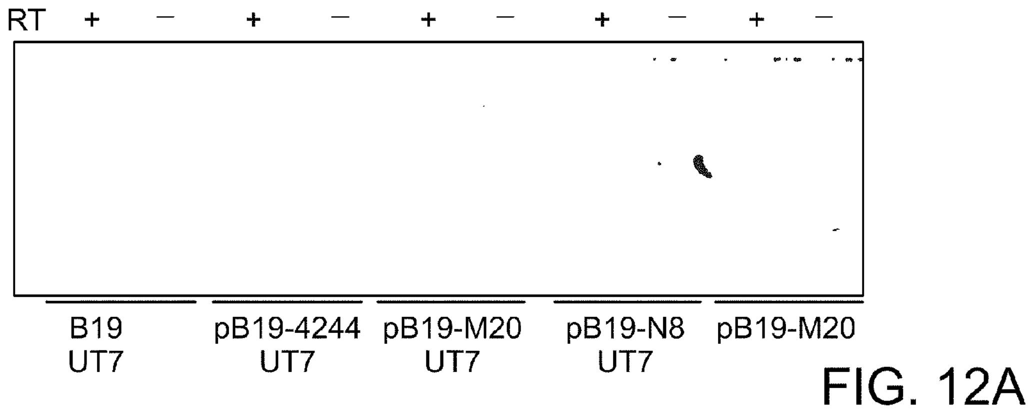
FIGS. 12A and 12B show RT-PCR analysis of UT7/Epo-S1 cells infected with clarified supernatant from B19-infected or p19-4244, pB19-M20, or pB19-N8 transfected cells for B19 transcripts. Total RNA was extracted from the cells 0 h (FIG. 12A) and 72 h (FIG. 12B) post-infection. RT-PCR was performed with a primer pair of B19-1 (SEQ ID NO:6) and B19-9 (SEQ ID NO:7). The PCR products were separated by agarose electrophoresis and analyzed by Southern blotting with an alkaline-phosphatase-labeled probe. (+) and (−) indicate the presence or absence respectively of reverse transcriptase in the PCR reaction. The numbers with arrows indicate amplicon size in base pairs (bp).
Figure 12B:
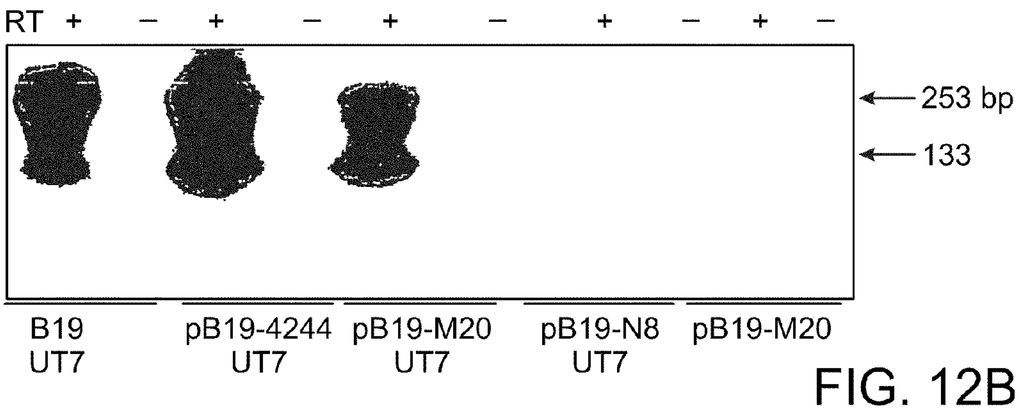

As observed previously, following transfection, spliced transcripts were detected in all the samples including cells transfected with pB19-N8 (FIG. 8). Immediately after inoculation of the clarified supernatant into the UT7/Epo-S1 cells, no RT-PCR product was detected in any of the sample (FIG. 12A), indicating that there was no carry-over of the RNA from the transfected cells. At 72 h post-inoculation spliced transcripts were detected in the samples derived from the cells transfected with pB19-4244 and pB19-M20, but not with pB19-N8 (FIG. 12B), confirming that the full-length viral genome containing complete ITRs is essential for generation of infectious viral particles. In addition, no viral transcripts were detected in cells in which the plasmids were directly incubated with the cells (no electroporation) (FIG. 12B), suggesting that the detection of transcripts in the cells inoculated with transfected-cell lysate was due to the production of infectious B19 virus from the plasmid.

Figure 13A:
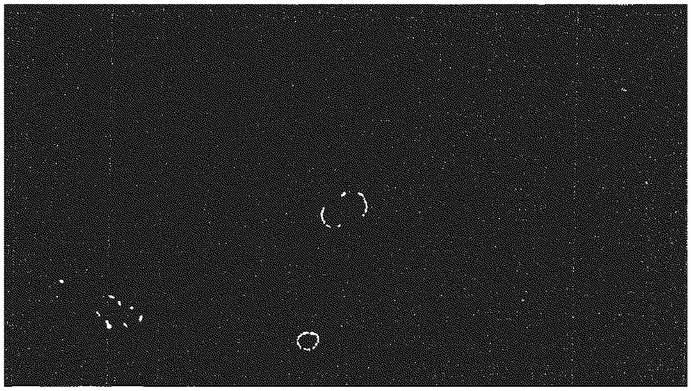
FIGS. 13A-C show detection of B19 capsid proteins in cells infected with clarified supernatant from B19-infected (FIG. 13A), or pB19-M20 (FIG. 13B) or pB19-N8 (FIG. 13C) transfected cells. B19 capsid proteins were detected 72 h post-infection using monoclonal antibody 521-5D. Magnification is 750×.
Figure 13B:
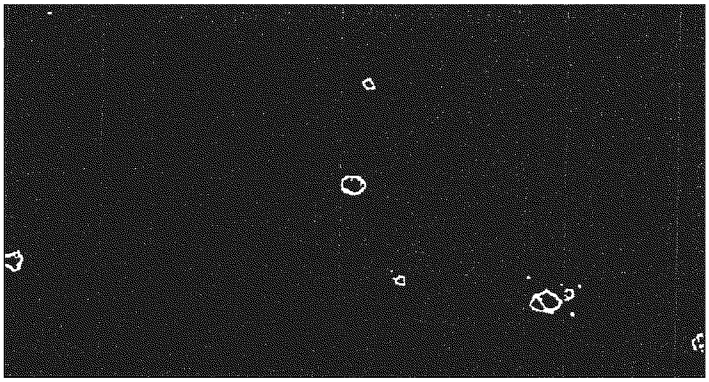
Figure 13C:

The infected cultures were also examined for the production of parvovirus B19 capsid proteins. At 72 h post-inoculation capsid proteins could be detected in the nuclei and cytoplasm of cells with the supernatants derived from either B19 infection or pB19-M20 transfection (FIGS. 13A and 13B), but not in the cells inoculated with either pB19-N8 cell lysate (FIG. 13C), or directly with plasmid.

We also performed in vitro neutralization assays to confirm that the infectivity of the cell lysates was mediated by newly synthesized B19 virons. Incubation of the cell lysates with neutralizing monoclonal antibody E (Yoshimoto et al., 1991) reduced the infectivity to undetectable levels in the WA testing. In contrast, incubation with a similar concentration of monoclonal antibody known to be non-neutralizing (monoclonal antibody A) had no effect on infection. This result further supports our infection experiment, indicating that infectious viral particles were produced from the cells transfected with the plasmids containing full-length B19 genome.

Figure 14:
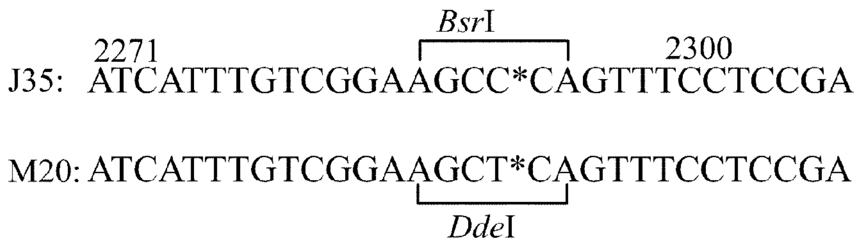
FIG. 14 shows a comparison of a portion of nucleic acid sequence from B19 clone J35 and B19 clone M20. M20 virus has a Ddel restriction site that is not present in J35 virus.
Figure 15:
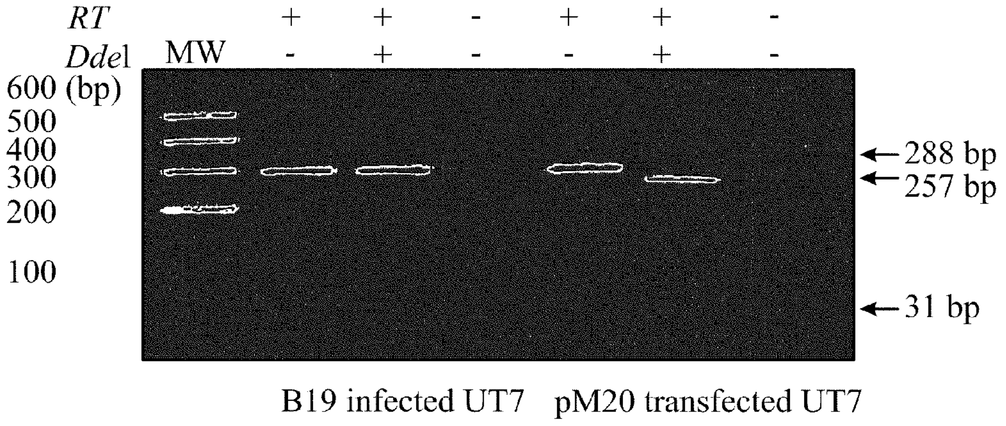
FIG. 15 shows RT-PCR analysis of B19 transcripts in UT7/Epo-S1 cells infected with J35 virus or infectious clone pB19-M20. cDNA derived from the infected cells was amplified using a primer pair of B19-2255 (SEQ ID NO:8) and B19-2543 (SEQ ID NO:9). The PCR products were digested with DdeI and analyzed by gel electrophoresis. (+) and (−) indicate the presence or absence respectively of reverse transcriptase in the PCR reaction. The numbers with arrows indicate amplicon size in base pairs (bp).

Finally to confirm that the viral transcripts in the inoculated cells were being generated from the infectious clone and not from laboratory contamination of wild type J35 virus, we constructed the second infectious clone (pB19-M20) that carried a DdeI site that was present in other B19 isolates but not in J35 virus. The sequencing analysis of the plasmids constructed in site-specific mutagenesis showed that full-length B19 genome including complete ITR was stable during serial passages in Sure2 bacteria cells, demonstrating the capacity for manipulating and stably passaging the infectious clone. After transfection, the viral transcripts were tested by restriction enzyme digestion for the presence of the artificially generated DdeI site (FIGS. 14 and 15). No DdeI site was present in transcripts generated by wild-type B19-J35 isolate infection. A DdeI was present only in transcripts from cells infected with lysate from pB19-M20-transfected cells (FIG. 15).

Example 6

Identification of Viral Proteins Involved in B19 Infection

Introduction

In common with other parvoviruses, B19 has a small (22 nm), nonenveloped, icosahedral capsid packaging a single-stranded DNA. The B19 genome has approximately 5,600 nucleotides. The ends of the genome are long inverted terminal repeats (ITR) of 383 nucleotides in length, of which the distal 365 nucleotides form an imperfect palindrome (Deiss et al., 1990). Transcription of the B19 viral genome is controlled by a single promoter p6 that regulates synthesis of nine viral transcripts to produce one nonstructural protein (NS), two capsid proteins (VP1 and VP2), and two small proteins (11-kDa and 7.5-kDa) of unknown function (St. Amand et al., 1993, *Virology,* 195:448-455). Additionally, there is a putative open reading frame encoding a functionally unknown small protein X (9-kDA).

In order to experimentally define the role of these genes, we utilized the infectious B19 clone described in Example 1 to generate knockout mutants in which the translational start codon for each of the described viral genes was substituted with a stop codon.

Methods

To knockout expression of VP1, 7.5-kDa protein, or protein X, the translational initiation site (ATG) at 5' of the gene was replaced with a stop codon (TAG). Plasmid pB19-M20/VP1(−) contained a knockout mutation for VP1. Plasmid pB19-M20/7.5(−) contained a knockout mutation for 7.5 kDa protein. Plasmid pB19-M20/X(−) contained a knockout mutation for protein X.

To prepare these knockout plasmids, the full-length plasmid pB19-4244 was cut with NheI and the 5' overhang filled in using T4 polymerase. The linearized plasmid was redigested with XbaI, the B19 fragment (from nucleotide 1249 to 3425 in the genome of B19-J35 isolate) ligated into an XbaI-Ecl13611-digested pBluescriptII KS+ cloning vector (Stratagene), and site-specific mutagenesis was performed using the Quickchange Site-directed Mutagenesis Kit (Stratagene). The primers shown in Table 3 were used in the site-specific mutagenesis.

TABLE 3

Knockout PCR primers

| Gene | Primer | Nucleotide Sequence | SEQ ID NO | Mutation |
|---|---|---|---|---|
| VP1 | Forward | 5'GCAAAGCTTTGTAGATTTAGAGTAAAGAAAGTGGCAAATGGTGGG3' | SEQ ID NO: 29 | A2624T and T2625A |
| | Reverse | 5'CCCACCATTTGCCACTTTCTTTACTCTAAATCTACAAAGCTTTGC3' | SEQ ID NO: 30 | |
| 7.5-kDa protein | Forward | 5'GATTTCCCTGGAATTATAGCAGATGCCCTCCACCCAGACC3' | SEQ ID NO: 31 | A2084T and T2083A |
| | Reverse | 5'GGTCTGGGTGGAGGGCATCTGCTATAATTCCAGGGAAATC3' | SEQ ID NO: 32 | |

TABLE 3-continued

Knockout PCR primers

| Gene | Primer | Nucleotide Sequence | SEQ ID NO | Mutation |
|---|---|---|---|---|
| Protein X | Forward | 5'AGTCATCATTTTCAAAGTCT AGGACAGTTATCTGACCACC3' | SEQ ID NO: 33 | A2874T and T2875A |
| | Reverse | 5'GGTGGTCAGATAACTGTCCT AGACTTTGAAAATGATGACT3' | SEQ ID NO: 34 | |

To eliminate an undesired XbaI restriction site in the vector sequence of the plasmid pB19-4244, the plasmid was digested with Ecl13611-XhoI enzymes, the XhoI overhang was blunted with T4 polymerase, and the plasmid was religated (plasmid pB19-4244d).

To knockout expression of 11-kDa protein, the third translational initiation site (ATG) at 5' of the 11-kDa protein gene was replaced with a stop codon (TAG). Plasmid pB19-M20/11(−) contained a knockout mutation for 11-kDa protein.

The full-length plasmid p1319-4244 described in Example 1 was cut with XabI and BbvCII and the B19 fragment (from nucleotide 1247 to 3423 in the genome of B19-J35 isolate) was ligated into an XbaI-BbvCI-digested pBluescriptII KS+cloning vector (Stratagene), and site-specific mutagenesis (A4917T, T4918A) was performed using the Quickchange Site-directed Mutagenesis Kit (Stratagene) and primers of P11(−)F3 (5'CACCACAGACATGGATTAGAAAAGCCTGAAGAATTGTGGAC3'; SEQ ID NO:35), and P11(−)R3 (5'GTCCACAATTCTTCAGGCTTTTCTAATCCATGTCTGTGGTG3'; SEQ ID NO:36). Plasmid with the B19 fragment containing both the A4917T and T4918A mutations was digested with XbaI-BbvCI and the fragment was ligated into XbaI-BbvCI aI digested pB19-4244d plasmid.

To disrupt the expression of NS protein, the full-length plasmid pB19-4244 was cut with AflII (at nucleotide 756 in B19 genome) and the 5' overhang filled in using T4 polymerase. The linearized plasmid was religated with T4 ligase, which generated a stop codon and disrupted the open reading frame of NS. The plasmid was named pB19-M20/NS(−).

To obtain the ITR deletion mutant, the primer B19-187FR (Table 1) was designed from the hairpin region of the virus using sequences available in GenBank (19-HV; Genbank accession number AF162273). High fidelity long PCR amplification was performed using the single primer B19-187FR with a HF-2 polymerase kit (BD Biosciences, Palo Alto, Calif.) with 25 cycles of amplification (94° C. for 15 sec; 55° C. for 30 sec; 72° C. for 4 min; followed by extension at 72° C. for 7 min). The amplicon was cloned by blunt ligation into a pCR-Blunt II TOPO (Invitrogen-Life Technologies, San Diego, Calif.) and transformed into Top10 cells (Invitrogen-Life Technologies).

Colonies were screened by hybridization with a $^{32}$P-random-primed B19 probe obtained from pYT103 as previously described for dotblot hybridization, (Nguyen et al., 2002) and positive clones confirmed by sequencing the plasmids using BigDye terminator cycle sequencing (ABI-Perkin Elmer, Foster City, Calif.). The full-length sequences of both strands were obtained by primer walking. One clone (pB19-N8) contained a 4844-nucleotide sequence including the entire coding region, and 177 nucleotides of the ITR at both 5' and 3' ends (GenBank AY386330).

UT7/Epo-S1 cells were transfected with the B19 variant plasmids using the AMAXA Cell Line Nucleofector™ kit R according to the manufacture's instructions (AMAXA Biosystems Inc., Cologne, Germany). The cells were harvested at various times post-transfection and used for DNA, RNA, and immunofluorescence studies. For infection studies, cells were harvested 72 h post-transfection, washed free of inoculums using fresh culture medium, and cell lysates prepared by three cycles of freeze/thawing. After centrifugation at 10,000 g for 10 min, the clarified supernatant was treated with RNase (final concentration of 1 U/μl, Roche) and collected for further infections.

B19 variant transcripts were detected using RT-PCR. Total RNA was extracted from the UT7/Epo-S1 cells ($2\times10^5$) using RNA STAT60 (Tel-Test Inc., Friendswood, Tex.). Residual DNA was removed by DNAse I treatment (final concentration, 90 U/ml) for 15 min at room temperature. RNA was converted to cDNA with random hexamers and SuperScript II and RT-PCR for the spliced capsid transcripts was performed with primers B19-1 and B19-9 as described in Example 4.

To exclude the possibility the detected transcripts detected were derived from laboratory contamination of B19 viral RNA, cDNA derived from pM20-transfected cells were PCR amplified by using a primer pair of B19-2255 and B19-2543 (Table 1), which targeted on the region containing the site of mutagenesis (C2285T). After purified by using QIAquick PCR Purification Kit (Qiagen Inc., Valencia, Calif.), the PCR products were digested with DdeI at 37° C. for 2 h.

B19 variants were analyzed for capsid protein expression using the indirect fluorescent antibody assay described in Example 4. Infected or transfected cells were harvested and cytocentrifuged (1500 rpm for 8 mins in a Shandon cytospin 2 cytocentrifge). The cells were fixed in acetone:methanol (1:1) at −20° C. for 5 min and washed twice in phosphate buffered saline (PBS) containing 0.1% fetal bovine serum, and incubated with a mouse monoclonal antibody specific to B19 capsid proteins (521-5D, obtained from Dr. Larry Anderson, CDC) or a rabbit polyclonal antibody to 11-kDa protein in PBS with 10% fetal calf serum for 1 hr at 37° C.

For double IFA staining, a lissamine rhodamine-labeled goat anti-mouse IgG and fluorescein isothiocyanate-labeled goat anti-rabbit IgG (Jackson ImmunoResearch Laboratories, Inc., West Grove, Pa.) were used as secondary antibodies. The B19 variants were then examined for capsid proteins using confocal microscopy (LSM 510, Leica).

Discussion

Figure 16A:
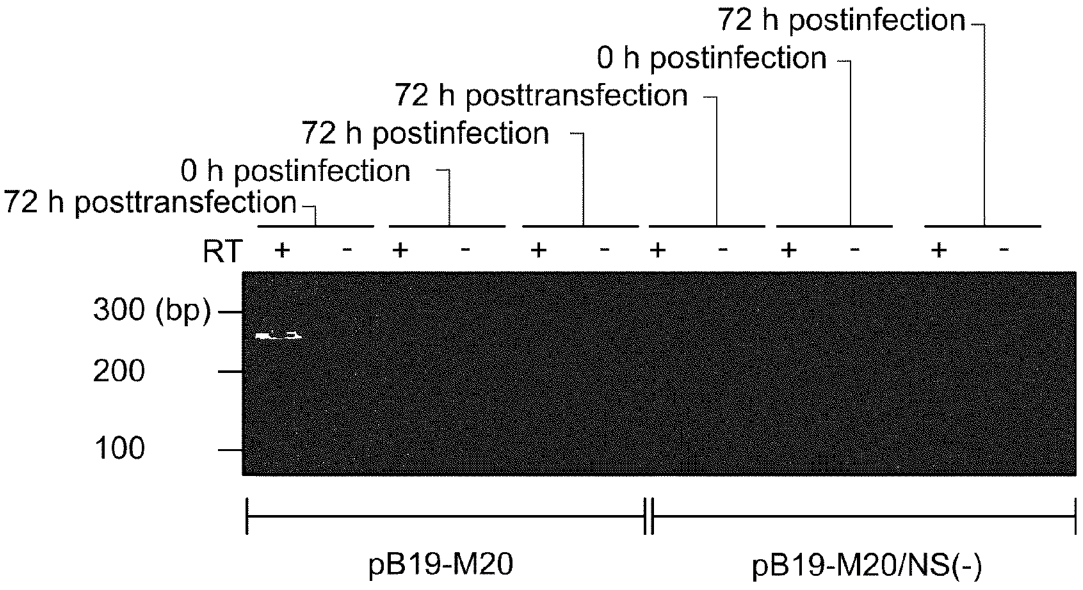
FIG. 16A-F shows RT-PCR analysis of B19 transcripts in UT7/Epo-S1 cells transfected with pB19-M20 (FIG. 16A), pB19-M20/NS (FIG. 16A), pB19-M20/VP1(−) (FIG. 16B), pB19-M20/11(−) (FIG. 16C), pB19-M20/7.5(−) (FIG. 16D), pB19-M20/X(−) (FIG. 16E), or pB19-N8 (FIG. 16F). At 72 h post-transfection, cells were infected with clarified supernatant from the transfected cells. Total RNA was extracted from the cells 72 h post-tranfection or 72 h post-infection. RT-PCR was performed with a primer pair of B19-1 (SEQ ID NO:6) and B19-9 (SEQ ID NO:7). The PCR products were separated by gel electrophoresis. (+) and (−) indicate the presence or absence respectively of reverse transcriptase in the PCR reaction.
Figure 16B:
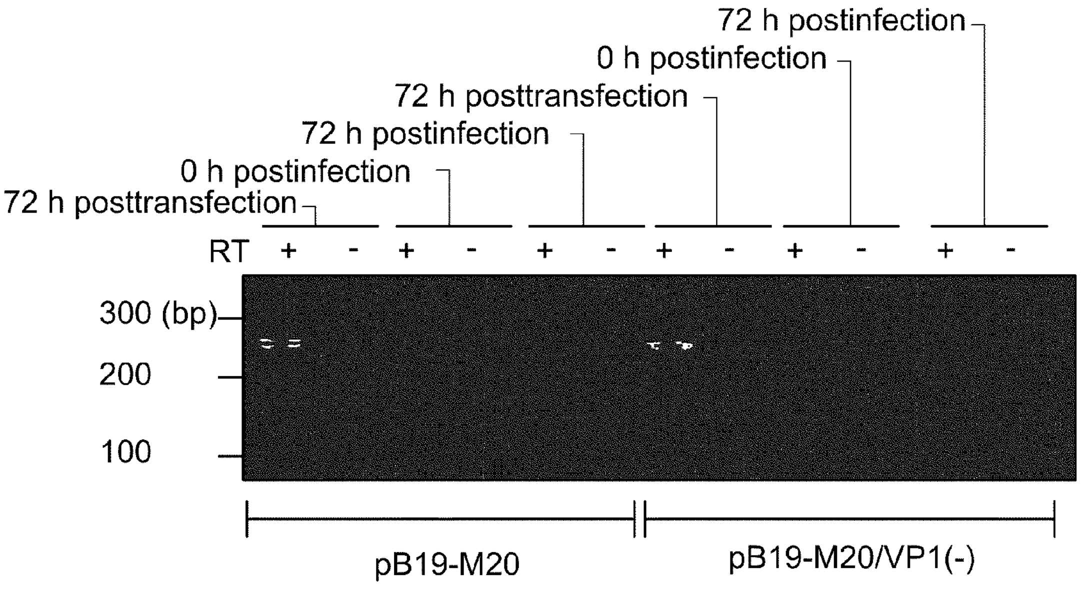
Figure 16C:
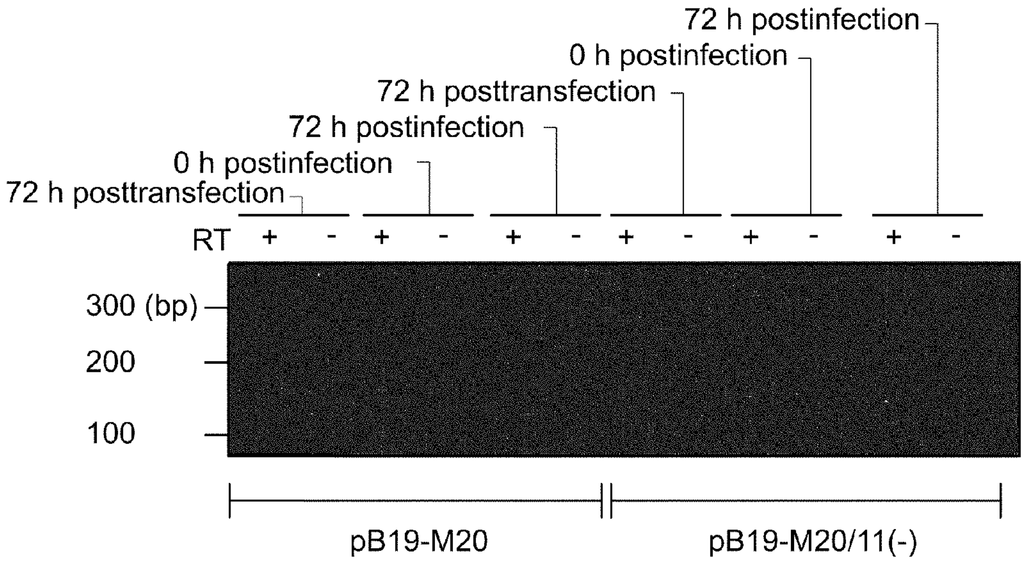
Figure 16D:
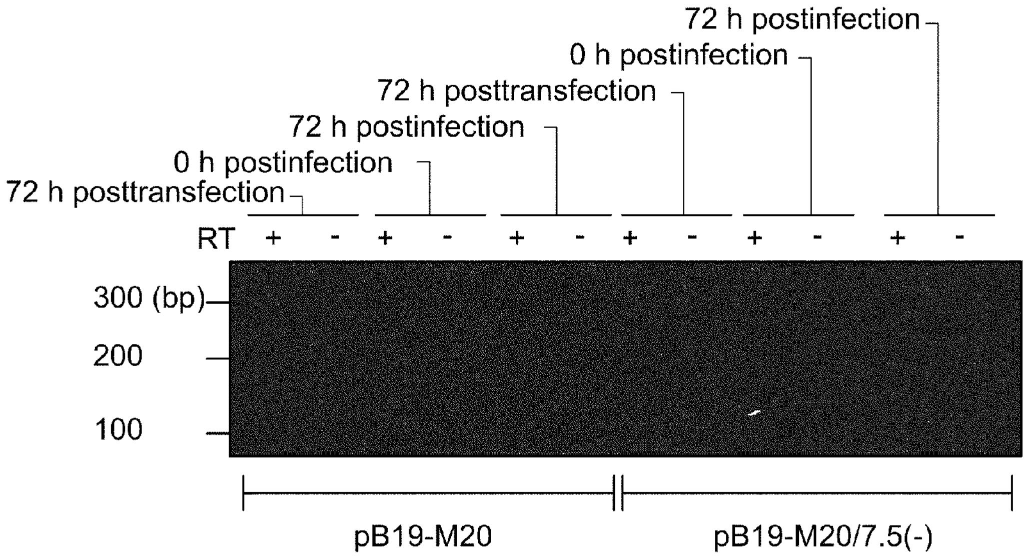
Figure 16E:
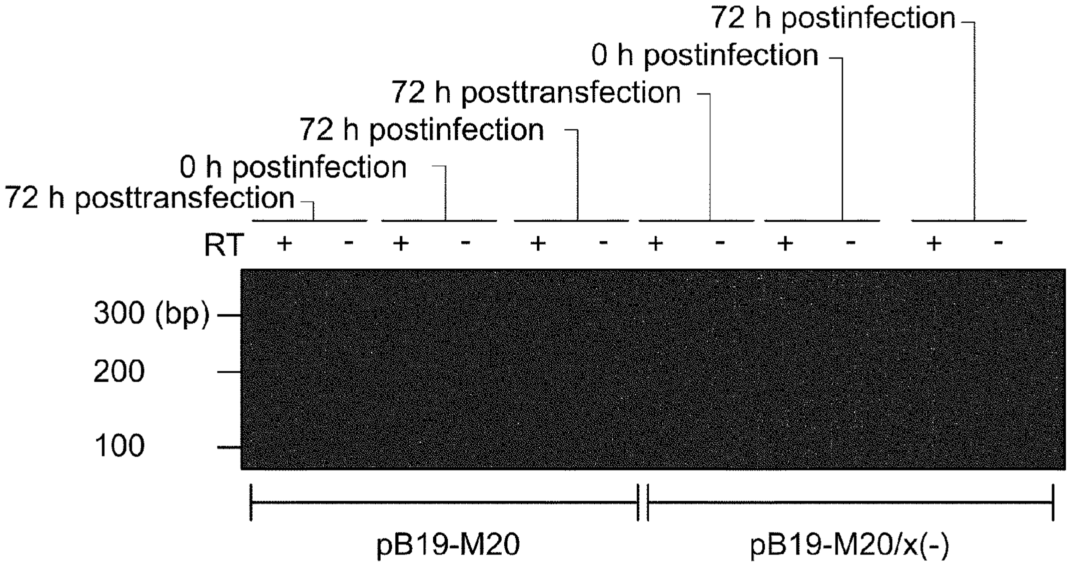
Figure 16F:
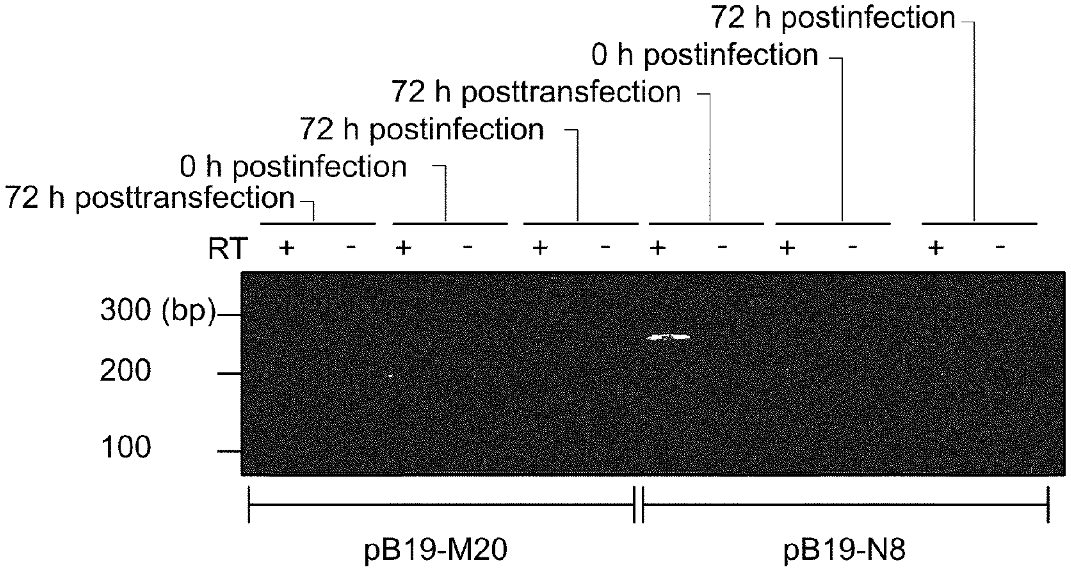
Figure 17A:
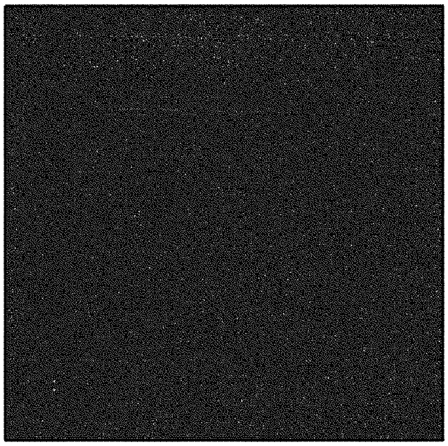
FIGS. 17A-D show detection of B19 capsid proteins and 11-kDa protein in cells transfected with pB19-M20 (FIGS. 17A and 17B respectively) or pB19-M20/11(−) (FIGS. 17C and 17D respectively). B19 capsid proteins were detected 72 h post-infection using monoclonal antibody 521-5D (FIG. 17A; 17C). 11-kDa protein was detected 72 h post-transfection using a rabbit polyclonal anti-11-kDa protein antibody (FIGS. 17B, 17D).
Figure 17B:
Figure 17C:
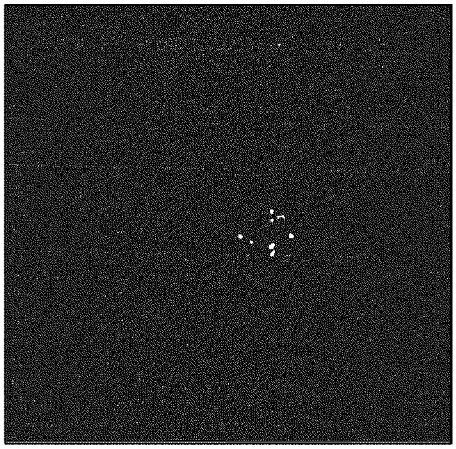
Figure 17D:
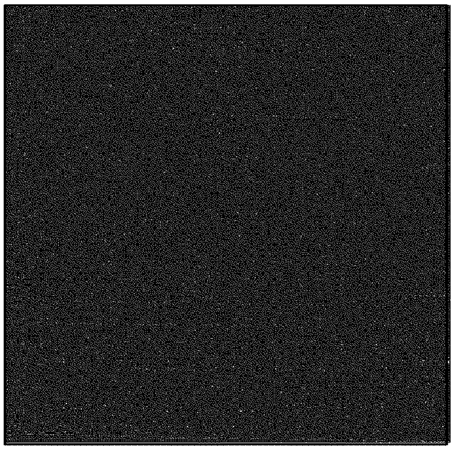

No infectious B19 virus was detected in cells transfected with NS, VP1, or 11-kDa protein knockout plasmids. As shown in FIGS. 16A-E, immediately following transfection, spliced transcripts were detected in cells transfected with pB19-M20 (FIG. 16A), pB19-M20/VP1(−) (FIG. 16B), pB19-M20/11(−) (FIG. 16C), pB19-M20/7.5(−) (FIG. 16D), pB19-M20/X (−) (FIG. 16E), or pB19-N8 (ITR deletion;

FIG. 16F). No spliced transcripts were detected in cells transfected with pB19-M20/NS(−) immediately following transfection (FIG. 16A).

Immediately following infection of UT7/Epo-S1 cells with clarified supernatant from the transfected cells, no RT-PCR product was detected in any of the cells, indicating that there was no carry-over of the RNA from the transfected cells (FIGS. 16A-F). Seventy-two h post-inoculation, spliced transcripts were detected in cells infected with supernatant derived from cells transfected with pB19-M20 (FIG. 16A), pB19-M20/7.5(−) (FIG. 16E), or pB19-M20/X (−) (FIG. 16E), but not pB19-M20/NS(−) (FIG. 16A), pB19-M20/VP1 (−) (FIG. 16B), pB19-M20/11(−) (FIG. 16C), or pB19-N8 (FIG. 16F). The data in FIG. 16 indicated that knocking out expression of 11-kDa protein, VP1, NS, or ITR reduced the production of infectious viral particles to an undetectable level.

Knocking out 11-kDa protein changed the expression and distribution pattern of B19 viral capsid protein (FIGS. 17A-D). In cells transfected with wild-type infectious clone, viral capsid protein first appeared in the host cell nucleus and was transported into the cytoplasm at a late stage of infection. Capsid protein was either evenly distributed or formed fine clusters in the cytoplasm and nucleus. In cells transfected with 11-kDa protein knockout plasmids, production of viral capsid protein was significantly decreased. Viral capsid protein formed rough clusters in the nucleus and could not be transported to cytoplasm (FIGS. 17 C and 17D), suggesting 11-kDa protein may be involved in regulation of viral promoter activity or viral capsid transportation.

Taken together, the data in FIGS. 16A-F and FIGS. 17A-D indicated that 11-kDa protein may play an important role in replication of B19 and confirmed that 11-kDa protein, in addition to ITR sequences and VP2, NS, and VP I proteins, is essential for production of infectious particles of B19 parvovirus.

We claim:

1. A method for cloning a parvovirus B19 viral genome comprising:

(a) introducing a vector comprising all or a portion of a parvovirus B19 genome into a prokaryotic cell that is deficient in at least one recombinase enzyme, wherein the method uses a full length inverted terminal repeat (ITR) at the 5' end and the 3' end of the genome, wherein the ITR located at the 5' end comprises SEQ ID NO:1 or SEQ ID NO:2, and wherein the ITR located at the 3' end comprises SEQ ID NO:1 or SEQ ID NO:2;

(b) incubating the cells at about 25° C. to 35° C.; and (c) recovering the vector from the prokaryotic cells.

2. The method of claim 1, wherein the ITR located at the 5' end or the 3' end comprises SEQ ID NO:1.

3. The method of claim 1, wherein the ITR located at the 5' end or the 3' end comprises SEQ ID NO:2.

4. The method of claim 1, wherein the viral genome further comprises a nucleic acid sequence encoding at least one or all of a parvovirus B19 VP1, a parvovirus B19 VP2, a parvovirus B19 nonstructural protein, or a parvovirus B19 11-kpa protein.

5. The method of claim 1, wherein the viral genome is a full length parvovirus B19 genome.

6. An isolated cell comprising an infectious clone of parvovirus comprising the parvovirus B19 ITR sequence set forth in SEQ ID NO: 1 and/or SEQ ID NO: 2.

7. A method for producing an infectious virus of parvovirus B19, comprising:

introducing a vector comprising an infectious clone of parvovirus B19 into a population of cells, wherein the infectious clone of parvovirus B19 comprises a parvovirus B19 genome, wherein the genome comprises a full length inverted terminal repeat (ITR) at the 5' end and the 3' end, wherein the ITR located at the 5' end comprises SEQ ID NO:1 or SEQ ID NO:2, wherein the ITR located at the 3' end comprises SEQ ID NO:1 or SEQ ID NO:2; and wherein the vector is present in at least about 15% of the cells; and incubating the cells under conditions to allow for viral replication.

8. The method of claim 7, wherein the cells are eukaryotic cells.

9. The method of claim 7, wherein introducing the vector into the population of cells is conducted by electric current.

10. The method of claim 9, wherein the cells are exposed to an electrical pulse comprising a field strength of about 2kV/cm to about 10kV/cm, a duration of at least about usec, and a current of at least about 1 A followed by a current flow of about 1 A to about 3 A for at least 10 msec.

* * * * *

```
                              SEQUENCE LISTING

<160> NUMBER OF SEQ ID NOS: 40

<210> SEQ ID NO 1
<211> LENGTH: 381
<212> TYPE: DNA
<213> ORGANISM: Parvovirus B19

<400> SEQUENCE: 1

aaatcagatg ccgccggtcg ccgccggtag gcgggacttc cggtacaaga tggcggacaa     60

ttacgtcatt tcctgtgacg tcatttcctg tgacgtcact tccggtgggc gggacttccg    120

gaattagggt tggctctggg ccagcttgct tggggttgcc ttgacactaa gacaagcggc    180

gcgccgcttg atcttagtgg cacgtcaacc ccaagcgctg gcccagagcc aaccctaatt    240

ccggaagtcc cgcccaccgg aagtgacgtc acaggaaatg acgtcacagg aaatgacgta    300

attgtccgcc atcttgtacc ggaagtcccg cctaccggcg gcgaccggcg gcatctgatt    360

tggtgtcttc ttttaaattt t                                               381


<210> SEQ ID NO 2
<211> LENGTH: 381
<212> TYPE: DNA
<213> ORGANISM: Parvovirus B19

<400> SEQUENCE: 2

aaatcagatg ccgccggtcg ccgccggtag gcgggacttc cggtacaaga tggcggacaa     60

ttacgtcatt tcctgtgacg tcatttcctg tgacgtcact tccggtgggc gggacttccg    120

gaattagggt tggctctggg ccagcgcttg gggttgacgt gccactaaga tcaagcggcg    180

cgccgcttgt cttagtgtca aggcaacccc aagcaagctg gcccagagcc aaccctaatt    240

ccggaagtcc cgcccaccgg aagtgacgtc acaggaaatg acgtcacagg aaatgacgta    300

attgtccgcc atcttgtacc ggaagtcccg cctaccggcg gcgaccggcg gcatctgatt    360

tggtgtcttc ttttaaattt t                                               381


<210> SEQ ID NO 3
<211> LENGTH: 365
<212> TYPE: DNA
<213> ORGANISM: Parvovirus B19

<400> SEQUENCE: 3
```

-continued

```
ccaaatcaga tgccgccggt cgccgccggt aggcgggact tccggtacaa gatggcggac     60

aattacgtca tttcctgtga cgtcatttcc tgtgacgtca cttccggtgg gcgggacttc    120

cggaattagg gttggctctg ggccagcgct tggggttgcc ttgacactaa gacaagcggc    180

gcgccgcttg atcttagtgg cacgtcaacc ccaagcaagc tggcccagag ccaaccctaa    240

ttccggaagt cccgcccacc ggaagtgacg tcacaggaaa tgacgtcaca ggaaatgacg    300

taattgtccg ccatcttgta ccggaagtcc cgcctaccgg cggcgaccgg cggcatctga    360

tttgg                                                                365
```

<210> SEQ ID NO 4
<211> LENGTH: 365
<212> TYPE: DNA
<213> ORGANISM: Parvovirus B19

<400> SEQUENCE: 4

```
ccaaatcaga tgccgccggt cgccgccggt aggcgggact tccggtacaa gatggcggac     60

aattacgtca tttcctgtga cgtcatttcc tgtgacgtca cttccggtgg gcgggacttc    120

cggaattagg gttggctctg ggccagcttg cttggggttg acgtgccact aagatcaagc    180

ggcgcgccgc ttgtcttagt gtcaaggcaa ccccaagcgc tggcccagag ccaaccctaa    240

ttccggaagt cccgcccacc ggaagtgacg tcacaggaaa tgacgtcaca ggaaatgacg    300

taattgtccg ccatcttgta ccggaagtcc cgcctaccgg cggcgaccgg cggcatctga    360

tttgg                                                                365
```

<210> SEQ ID NO 5
<211> LENGTH: 5592
<212> TYPE: DNA
<213> ORGANISM: Parvovirus B19

<400> SEQUENCE: 5

```
aaatcagatg ccgccggtcg ccgccggtag gcgggacttc cggtacaaga tggcggacaa     60

ttacgtcatt tcctgtgacg tcatttcctg tgacgtcact tccggtgggc gggacttccg    120

gaattagggt tggctctggg ccagcttgct tggggttgcc ttgacactaa gacaagcggc    180

gcgccgcttg atcttagtgg cacgtcaacc ccaagcgctg gcccagagcc aaccctaatt    240

ccggaagtcc cgcccaccgg aagtgacgtc acaggaaatg acgtcacagg aaatgacgta    300

attgtccgcc atcttgtacc ggaagtcccg cctaccggcg gcgaccggcg gcatctgatt    360

tggtgtcttc ttttaaattt tagcgggctt ttttcccgcc ttatgcaaat gggcagccat    420

tttaagtgtt ttactataat tttattggtc agttttgtaa cggttaaaat gggcggagcg    480

taggcgggga ctacagtata tatagcacag cactgccgca gctctttctt tctgggctgc    540

tttttcctgg actttcttgc tgttttttgt gagctaacta acaggtattt atactacttg    600

ttaatatact aacatggagc tatttagagg ggtgcttcaa gtttcttcta atgttctgga    660

ctgtgctaac gataactggt ggtgctcttt actagattta gacacttctg actgggaacc    720

actaactcat actaacagac taatggcaat atacttaagc agtgtggctt ctaagcttga    780

ccttaccggg ggccactag cagggtgctt gtactttttt caagcagaat gtaacaaatt    840

tgaagaaggc tatcatattc atgtggttat tggggggcca gggttaaacc ccagaaacct    900

cacagtgtgt gtagaggggt tatttaataa tgtactttat cactttgtaa ctgaaaatgt    960

gaagctaaaa tttttgccag gaatgactac aaaaggcaaa tactttagag atggagagca   1020

gtttatagaa aactatttaa tgaaaaaaat acctttaaat gttgtatggt gtgttactaa   1080
```

-continued

```
tattgatgga tatatagata cctgtatttc tgctactttt agaaggggag cttgccatgc   1140
caagaaaccc cgcattacca cagccataaa tgatactagt agcgatgctg gggagtctag   1200
cggcacaggg gcagaggttg tgccatttaa tgggaaggga actaaggcta gcataaagtt   1260
tcaaactatg gtaaactggt tgtgtgaaaa cagagtgttt acagaggata agtggaaact   1320
agttgacttt aaccagtaca ctttactaag cagtagtcac agtggaagtt ttcaaattca   1380
aagtgcacta aaactagcaa tttataaagc aactaattta gtgcctacta gcacattttt   1440
attgcataca gactttgagc aggttatgtg tattaaagac aataaaattg ttaaattgtt   1500
actttgtcaa aactatgacc ccctattggt ggggcagcat gtgttaaagt ggattgataa   1560
aaaatgtggc aagaaaaata cactgtggtt ttatgggccg ccaagtacag gaaaaacaaa   1620
cttggcaatg gccattgcta aaagtgttcc agtatatggc atggttaact ggaataatga   1680
aaactttcca tttaatgatg tagcaggaaa aagcttggtg gtctgggatg aaggtattat   1740
taagtctaca attgtagaag ctgcaaaagc cattttaggc gggcaaccca ccagggtaga   1800
tcaaaaaatg cgtggaagtg tagctgtgcc tggagtacct gtggttataa ccagcaatgg   1860
tgacattact tttgttgtaa gcgggaacac tacaacaact gtacatgcta aagccttaaa   1920
agagcgcatg gtaaagttaa actttactgt aagatgcagc cctgacatgg ggttactaac   1980
agaggctgat gtacaacagt ggcttacatg gtgtaatgca caaagctggg accactatga   2040
aaactgggca ataaactaca cttttgattt ccctggaatt aatgcagatg ccctccaccc   2100
agacctccaa accaccccaa ttgtcacaga caccagtatc agcagcagtg gtggtgaaag   2160
ctctgaagaa ctcagtgaaa gcagcttttt taacctcatc accccaggcg cctggaacac   2220
tgaaaccccg cgctctagta cgcccatccc cgggaccagt tcaggagaat catttgtcgg   2280
aagcccagtt tcctccgaag ttgtagctgc atcgtgggaa gaagccttct acacaccttt   2340
ggcagaccag tttcgtgaac tgttagttgg ggttgattat gtgtgggacg gtgtaagggg   2400
tttacctgtg tgttgtgtgc aacatattaa caatagtggg ggaggcttgg gactttgtcc   2460
ccattgcatt aatgtagggg cttggtataa tggatggaaa tttcgagaat ttaccccaga   2520
tttggtgcga tgtagctgcc atgtgggagc ttctaatccc ttttctgtgc taacctgcaa   2580
aaaatgtgct tacctgtctg gattgcaaag ctttgtagat tatgagtaaa gaaagtggca   2640
aatggtggga aagtgatgat gaatttgcta aagctgtgta tcagcaattt gtggaatttt   2700
atgaaaaggt tactggaaca gacttagagc ttattcaaat attaaaagat cattataata   2760
tttctttaga taatccccta gaaaacccat cctctctgtt tgacttagtt gctcgcatta   2820
aaaataacct taaaaattct ccagacttat atagtcatca ttttcaaagt catggacagt   2880
tatctgacca cccccatgcc ttatcatcca gtagcagtca tgcagaacct agaggagaag   2940
atgcagtatt atctagtgaa gacttacaca agcctgggca agttagcgta caactacccg   3000
gtactaacta tgttgggcct ggcaatgagc tacaagctgg gcccccgcaa agtgctgttg   3060
acagtgctgc aaggattcat gactttaggt atagccaact ggctaagttg ggaataaatc   3120
catatactca ttggactgta gcagatgaag agcttttaaa aaatataaaa aatgaaactg   3180
ggtttcaagc acaagtagta aaagactact ttactttaaa aggtgcagct gcccctgtgg   3240
cccattttca aggaagtttg ccggaagttc ccgcttacaa cgcctcagaa aaatacccaa   3300
gcatgacttc agttaattct gcagaagcca gcactggtgc aggagggggg ggcagtaatc   3360
ctgtcaaaag catgtggagt gagggggcca cttttagtgc caactctgtg acttgtacat   3420
tttctagaca gtttttaatt ccatatgacc cagagcacca ttataaggtg ttttctcccg   3480
```

-continued

```
cagcaagtag ctgccacaat gccagtggaa aggaggcaaa ggtttgcacc attagtccca   3540

taatgggata ctcaacccca tggagatatt tagattttaa tgctttaaac ttattttttt   3600

cacctttaga gtttcagcac ttaattgaaa attatggaag tatagctcct gatgctttaa   3660

ctgtaaccat atcagaaatt gctgttaagg atgttacaga caaaactgga ggggggggtgc   3720

aggttactga cagcactaca gggcgcctat gcatgttagt agaccatgaa tacaagtacc   3780

catatgtgtt agggcaaggt caagatactt tagccccaga acttcctatt tgggtatact   3840

ttcccccctca atatgcttac ttaacagtag gagatgttaa cacacaagga atttctggag   3900

acagcaaaaa attagcaagt gaagaatcag cattttatgt tttggaacac agttcttttc   3960

agcttttagg tacaggaggt acagcaacta tgtcttataa gtttcctcca gtgccccccag   4020

aaaatttaga gggctgcagt caacactttt atgagatgta caatccctta tacggatccc   4080

gcttaggggt tcctgacaca ttaggaggtg acccaaaatt tagatcttta acacatgaag   4140

accatgcaat tcagccccaa aacttcatgc cagggccact agtaaactca gtgtctacaa   4200

aggagggaga cagctctaat actggagctg ggaaagcctt aacaggcctt agcacaggta   4260

cctctcaaaa cactagaata tccttacgcc cggggccagt gtctcagccg taccaccact   4320

gggacacaga taaatatgtc acaggaataa atgctatttc tcatggtcag accacttatg   4380

gtaacgctga agacaaagag tatcagcaag gagtgggtag atttccaaat gaaaaagaac   4440

agctaaaaca gttacagggt ttaaacatgc acacctactt tcccaataaa ggaacccagc   4500

aatatacaga tcaaattgag cgccccctaa tggtgggttc tgtatggaac agaagagccc   4560

ttcactatga aagccagctg tggagtaaaa ttccaaattt agatgacagt tttaaaactc   4620

agtttgcagc cttaggagga tggggtttgc atcagccacc tcctcaaata tttttaaaaa   4680

tattaccaca aagtgggcca attggaggta ttaaatcaat gggaattact accttagttc   4740

agtatgccgt gggaattatg acagtaacca tgacatttaa attggggccc cgtaaagcta   4800

cgggacggtg gaatcctcaa cctggagtat atcccccgca cgcagcaggt catttaccat   4860

atgtactata tgaccctaca gctacagatg caaaaacaaca ccacagacat ggatatgaaa   4920

agcctgaaga attgtggaca gccaaaagcc gtgtgcaccc attgtaaaca ctccccaccg   4980

tgccctcagc caggatgcgt aactaaacgc ccaccagtac cacccagact gtacctgccc   5040

cctcctatac ctataagaca gcctaacaca aaagatatag acaatgtaga atttaagtat   5100

ttaaccagat atgaacaaca tgttattaga atgttaagat tgtgtaatat gtatcaaaat   5160

ttagaaaaat aaacgtttgt tgtggttaaa aaattatgtt gttgcgcttt aaaaatttaa   5220

aagaagacac caaatcagat gccgccggtc gccgccggta ggcgggactt ccggtacaag   5280

atggcggaca attacgtcat ttcctgtgac gtcatttcct gtgacgtcac ttccggtggg   5340

cggaacttcc ggaattaggg ttggctctgg gccagcgctt ggggttgacg tgccactaag   5400

atcaagcggc gcgccgcttg tcttagtgtc aaggcaaccc caagcaagct ggcccagagc   5460

caaccctaat tccggaagtc ccgcccaccg gaagtgacgt cacaggaaat gacgtcacag   5520

gaaatgacgt aattgtccgc catcttgtac cggaagtccc gcctaccggc ggcgaccggc   5580

ggcatctgat tt                                                       5592
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gttttttgtg agctaacta 19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ccacgatgca agctacaact t 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ggaaccagtt caggagaatc a 21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
tggcagctac atcgcaccaa 20

<210> SEQ ID NO 10
<211> LENGTH: 94
<212> TYPE: PRT
<213> ORGANISM: Parvovirus B19

<400> SEQUENCE: 10

```
Met Gln Asn Asn Thr Thr Asp Met Asp Met Lys Ser Leu Lys Asn Cys
1               5                   10                  15

Gly Gln Pro Lys Ala Val Cys Thr His Cys Lys His Ser Pro Pro Cys
            20                  25                  30

Pro Gln Pro Gly Cys Val Thr Lys Arg Pro Pro Val Pro Pro Arg Leu
        35                  40                  45

Tyr Leu Pro Pro Pro Ile Pro Ile Arg Gln Pro Asn Thr Lys Asp Ile
    50                  55                  60

Asp Asn Val Glu Phe Lys Tyr Leu Thr Arg Tyr Glu Gln His Val Ile
65                  70                  75                  80

Arg Met Leu Arg Leu Cys Asn Met Tyr Gln Asn Leu Glu Lys
                85                  90
```

<210> SEQ ID NO 11
<211> LENGTH: 671
<212> TYPE: PRT
<213> ORGANISM: Parvovirus B19

<400> SEQUENCE: 11

```
Met Glu Leu Phe Arg Gly Val Leu Gln Val Ser Ser Asn Val Leu Asp
1               5                   10                  15
```

-continued

```
Cys Ala Asn Asp Asn Trp Trp Cys Ser Leu Leu Asp Leu Asp Thr Ser
            20                  25                  30

Asp Trp Glu Pro Leu Thr His Thr Asn Arg Leu Met Ala Ile Tyr Leu
        35                  40                  45

Ser Ser Val Ala Ser Lys Leu Asp Leu Thr Gly Gly Pro Leu Ala Gly
    50                  55                  60

Cys Leu Tyr Phe Phe Gln Ala Glu Cys Asn Lys Phe Glu Glu Gly Tyr
65                  70                  75                  80

His Ile His Val Val Ile Gly Gly Pro Gly Leu Asn Pro Arg Asn Leu
                85                  90                  95

Thr Val Cys Val Glu Gly Leu Phe Asn Asn Val Leu Tyr His Phe Val
            100                 105                 110

Thr Glu Asn Val Lys Leu Lys Phe Leu Pro Gly Met Thr Thr Lys Gly
        115                 120                 125

Lys Tyr Phe Arg Asp Gly Glu Gln Phe Ile Glu Asn Tyr Leu Met Lys
    130                 135                 140

Lys Ile Pro Leu Asn Val Val Trp Cys Val Thr Asn Ile Asp Gly Tyr
145                 150                 155                 160

Ile Asp Thr Cys Ile Ser Ala Thr Phe Arg Arg Gly Ala Cys His Ala
                165                 170                 175

Lys Lys Pro Arg Ile Thr Thr Ala Ile Asn Asp Thr Ser Ser Asp Ala
            180                 185                 190

Gly Glu Ser Ser Gly Thr Gly Ala Glu Val Val Pro Phe Asn Gly Lys
        195                 200                 205

Gly Thr Lys Ala Ser Ile Lys Phe Gln Thr Met Val Asn Trp Leu Cys
    210                 215                 220

Glu Asn Arg Val Phe Thr Glu Asp Lys Trp Lys Leu Val Asp Phe Asn
225                 230                 235                 240

Gln Tyr Thr Leu Leu Ser Ser Ser His Ser Gly Ser Phe Gln Ile Gln
                245                 250                 255

Ser Ala Leu Lys Leu Ala Ile Tyr Lys Ala Thr Asn Leu Val Pro Thr
            260                 265                 270

Ser Thr Phe Leu Leu His Thr Asp Phe Glu Gln Val Met Cys Ile Lys
        275                 280                 285

Asp Asn Lys Ile Val Lys Leu Leu Leu Cys Gln Asn Tyr Asp Pro Leu
    290                 295                 300

Leu Val Gly Gln His Val Leu Lys Trp Ile Asp Lys Lys Cys Gly Lys
305                 310                 315                 320

Lys Asn Thr Leu Trp Phe Tyr Gly Pro Pro Ser Thr Gly Lys Thr Asn
                325                 330                 335

Leu Ala Met Ala Ile Ala Lys Ser Val Pro Val Tyr Gly Met Val Asn
            340                 345                 350

Trp Asn Asn Glu Asn Phe Pro Phe Asn Asp Val Ala Gly Lys Ser Leu
        355                 360                 365

Val Val Trp Asp Glu Gly Ile Ile Lys Ser Thr Ile Val Glu Ala Ala
    370                 375                 380

Lys Ala Ile Leu Gly Gly Gln Pro Thr Arg Val Asp Gln Lys Met Arg
385                 390                 395                 400

Gly Ser Val Ala Val Pro Gly Val Pro Val Val Ile Thr Ser Asn Gly
                405                 410                 415

Asp Ile Thr Phe Val Val Ser Gly Asn Thr Thr Thr Thr Val His Ala
            420                 425                 430

Lys Ala Leu Lys Glu Arg Met Val Lys Leu Asn Phe Thr Val Arg Cys
```

```
        435                 440                 445

Ser Pro Asp Met Gly Leu Leu Thr Glu Ala Asp Val Gln Gln Trp Leu
    450                 455                 460

Thr Trp Cys Asn Ala Gln Ser Trp Asp His Tyr Glu Asn Trp Ala Ile
465                 470                 475                 480

Asn Tyr Thr Phe Asp Phe Pro Gly Ile Asn Ala Asp Ala Leu His Pro
                485                 490                 495

Asp Leu Gln Thr Thr Pro Ile Val Thr Asp Thr Ser Ile Ser Ser Ser
            500                 505                 510

Gly Gly Glu Ser Ser Glu Glu Leu Ser Glu Ser Ser Phe Phe Asn Leu
        515                 520                 525

Ile Thr Pro Gly Ala Trp Asn Thr Glu Thr Pro Arg Ser Ser Thr Pro
    530                 535                 540

Ile Pro Gly Thr Ser Ser Gly Glu Ser Phe Val Gly Ser Pro Val Ser
545                 550                 555                 560

Ser Glu Val Val Ala Ala Ser Trp Glu Glu Ala Phe Tyr Thr Pro Leu
                565                 570                 575

Ala Asp Gln Phe Arg Glu Leu Leu Val Gly Val Asp Tyr Val Trp Asp
            580                 585                 590

Gly Val Arg Gly Leu Pro Val Cys Cys Val Gln His Ile Asn Asn Ser
        595                 600                 605

Gly Gly Gly Leu Gly Leu Cys Pro His Cys Ile Asn Val Gly Ala Trp
    610                 615                 620

Tyr Asn Gly Trp Lys Phe Arg Glu Phe Thr Pro Asp Leu Val Arg Cys
625                 630                 635                 640

Ser Cys His Val Gly Ala Ser Asn Pro Phe Ser Val Leu Thr Cys Lys
                645                 650                 655

Lys Cys Ala Tyr Leu Ser Gly Leu Gln Ser Phe Val Asp Tyr Glu
            660                 665                 670


<210> SEQ ID NO 12
<211> LENGTH: 781
<212> TYPE: PRT
<213> ORGANISM: Parvovirus B19

<400> SEQUENCE: 12

Met Ser Lys Glu Ser Gly Lys Trp Trp Glu Ser Asp Asp Glu Phe Ala
1               5                   10                  15

Lys Ala Val Tyr Gln Gln Phe Val Glu Phe Tyr Glu Lys Val Thr Gly
            20                  25                  30

Thr Asp Leu Glu Leu Ile Gln Ile Leu Lys Asp His Tyr Asn Ile Ser
        35                  40                  45

Leu Asp Asn Pro Leu Glu Asn Pro Ser Ser Leu Phe Asp Leu Val Ala
    50                  55                  60

Arg Ile Lys Asn Asn Leu Lys Asn Ser Pro Asp Leu Tyr Ser His His
65                  70                  75                  80

Phe Gln Ser His Gly Gln Leu Ser Asp His Pro His Ala Leu Ser Ser
                85                  90                  95

Ser Ser Ser His Ala Glu Pro Arg Gly Glu Asp Ala Val Leu Ser Ser
            100                 105                 110

Glu Asp Leu His Lys Pro Gly Gln Val Ser Val Gln Leu Pro Gly Thr
        115                 120                 125

Asn Tyr Val Gly Pro Gly Asn Glu Leu Gln Ala Gly Pro Pro Gln Ser
    130                 135                 140

Ala Val Asp Ser Ala Ala Arg Ile His Asp Phe Arg Tyr Ser Gln Leu
```

-continued

```
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Val
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser Met Thr Ser Val Asn Ser Ala Glu Ala Ser Thr Gly Ala
225                 230                 235                 240

Gly Gly Gly Gly Ser Asn Pro Val Lys Ser Met Trp Ser Glu Gly Ala
                245                 250                 255

Thr Phe Ser Ala Asn Ser Val Thr Cys Thr Phe Ser Arg Gln Phe Leu
            260                 265                 270

Ile Pro Tyr Asp Pro Glu His His Tyr Lys Val Phe Ser Pro Ala Ala
        275                 280                 285

Ser Ser Cys His Asn Ala Ser Gly Lys Glu Ala Lys Val Cys Thr Ile
    290                 295                 300

Ser Pro Ile Met Gly Tyr Ser Thr Pro Trp Arg Tyr Leu Asp Phe Asn
305                 310                 315                 320

Ala Leu Asn Leu Phe Phe Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350

Ile Ala Val Lys Asp Val Thr Asp Lys Thr Gly Gly Gly Val Gln Val
        355                 360                 365

Thr Asp Ser Thr Thr Gly Arg Leu Cys Met Leu Val Asp His Glu Tyr
    370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Val
                405                 410                 415

Gly Asp Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Gln Leu
        435                 440                 445

Leu Gly Thr Gly Gly Thr Ala Thr Met Ser Tyr Lys Phe Pro Pro Val
    450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Val Asn Ser Val Ser Thr Lys Glu
        515                 520                 525

Gly Asp Ser Ser Asn Thr Gly Ala Gly Lys Ala Leu Thr Gly Leu Ser
    530                 535                 540

Thr Gly Thr Ser Gln Asn Thr Arg Ile Ser Leu Arg Pro Gly Pro Val
545                 550                 555                 560

Ser Gln Pro Tyr His His Trp Asp Thr Asp Lys Tyr Val Thr Gly Ile
                565                 570                 575
```

-continued

```
Asn Ala Ile Ser His Gly Gln Thr Thr Tyr Gly Asn Ala Glu Asp Lys
            580                 585                 590

Glu Tyr Gln Gln Gly Val Gly Arg Phe Pro Asn Glu Lys Glu Gln Leu
        595                 600                 605

Lys Gln Leu Gln Gly Leu Asn Met His Thr Tyr Phe Pro Asn Lys Gly
    610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
                645                 650                 655

Ile Pro Asn Leu Asp Asp Ser Phe Lys Thr Gln Phe Ala Ala Leu Gly
            660                 665                 670

Gly Trp Gly Leu His Gln Pro Pro Pro Gln Ile Phe Leu Lys Ile Leu
        675                 680                 685

Pro Gln Ser Gly Pro Ile Gly Gly Ile Lys Ser Met Gly Ile Thr Thr
    690                 695                 700

Leu Val Gln Tyr Ala Val Gly Ile Met Thr Val Thr Met Thr Phe Lys
705                 710                 715                 720

Leu Gly Pro Arg Lys Ala Thr Gly Arg Trp Asn Pro Gln Pro Gly Val
                725                 730                 735

Tyr Pro Pro His Ala Ala Gly His Leu Pro Tyr Val Leu Tyr Asp Pro
            740                 745                 750

Thr Ala Thr Asp Ala Lys Gln His His Arg His Gly Tyr Glu Lys Pro
        755                 760                 765

Glu Glu Leu Trp Thr Ala Lys Ser Arg Val His Pro Leu
    770                 775                 780


<210> SEQ ID NO 13
<211> LENGTH: 554
<212> TYPE: PRT
<213> ORGANISM: Parvovirus B19

<400> SEQUENCE: 13

Met Thr Ser Val Asn Ser Ala Glu Ala Ser Thr Gly Ala Gly Gly Gly
1               5                   10                  15

Gly Ser Asn Pro Val Lys Ser Met Trp Ser Glu Gly Ala Thr Phe Ser
            20                  25                  30

Ala Asn Ser Val Thr Cys Thr Phe Ser Arg Gln Phe Leu Ile Pro Tyr
        35                  40                  45

Asp Pro Glu His His Tyr Lys Val Phe Ser Pro Ala Ala Ser Ser Cys
    50                  55                  60

His Asn Ala Ser Gly Lys Glu Ala Lys Val Cys Thr Ile Ser Pro Ile
65                  70                  75                  80

Met Gly Tyr Ser Thr Pro Trp Arg Tyr Leu Asp Phe Asn Ala Leu Asn
                85                  90                  95

Leu Phe Phe Ser Pro Leu Glu Phe Gln His Leu Ile Glu Asn Tyr Gly
            100                 105                 110

Ser Ile Ala Pro Asp Ala Leu Thr Val Thr Ile Ser Glu Ile Ala Val
        115                 120                 125

Lys Asp Val Thr Asp Lys Thr Gly Gly Gly Val Gln Val Thr Asp Ser
    130                 135                 140

Thr Thr Gly Arg Leu Cys Met Leu Val Asp His Glu Tyr Lys Tyr Pro
145                 150                 155                 160

Tyr Val Leu Gly Gln Gly Gln Asp Thr Leu Ala Pro Glu Leu Pro Ile
                165                 170                 175
```

-continued

```
Trp Val Tyr Phe Pro Pro Gln Tyr Ala Tyr Leu Thr Val Gly Asp Val
            180                 185                 190

Asn Thr Gln Gly Ile Ser Gly Asp Ser Lys Lys Leu Ala Ser Glu Glu
        195                 200                 205

Ser Ala Phe Tyr Val Leu Glu His Ser Ser Phe Gln Leu Leu Gly Thr
    210                 215                 220

Gly Gly Thr Ala Thr Met Ser Tyr Lys Phe Pro Pro Val Pro Pro Glu
225                 230                 235                 240

Asn Leu Glu Gly Cys Ser Gln His Phe Tyr Glu Met Tyr Asn Pro Leu
                245                 250                 255

Tyr Gly Ser Arg Leu Gly Val Pro Asp Thr Leu Gly Gly Asp Pro Lys
            260                 265                 270

Phe Arg Ser Leu Thr His Glu Asp His Ala Ile Gln Pro Gln Asn Phe
        275                 280                 285

Met Pro Gly Pro Leu Val Asn Ser Val Ser Thr Lys Glu Gly Asp Ser
    290                 295                 300

Ser Asn Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
            340                 345                 350

Ser His Gly Gln Thr Thr Tyr Gly Asn Ala Glu Asp Lys Glu Tyr Gln
        355                 360                 365

Gln Gly Val Gly Arg Phe Pro Asn Glu Lys Glu Gln Leu Lys Gln Leu
    370                 375                 380

Gln Gly Leu Asn Met His Thr Tyr Phe Pro Asn Lys Gly Thr Gln Gln
385                 390                 395                 400

Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
            420                 425                 430

Leu Asp Asp Ser Phe Lys Thr Gln Phe Ala Ala Leu Gly Gly Trp Gly
        435                 440                 445

Leu His Gln Pro Pro Pro Gln Ile Phe Leu Lys Ile Leu Pro Gln Ser
    450                 455                 460

Gly Pro Ile Gly Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro
                485                 490                 495

Arg Lys Ala Thr Gly Arg Trp Asn Pro Gln Pro Gly Val Tyr Pro Pro
            500                 505                 510

His Ala Ala Gly His Leu Pro Tyr Val Leu Tyr Asp Pro Thr Ala Thr
        515                 520                 525

Asp Ala Lys Gln His His Arg His Gly Tyr Glu Lys Pro Glu Glu Leu
    530                 535                 540

Trp Thr Ala Lys Ser Arg Val His Pro Leu
545                 550
```

<210> SEQ ID NO 14
<211> LENGTH: 74
<212> TYPE: PRT
<213> ORGANISM: Parvovirus B19

<400> SEQUENCE: 14

```
Met Gln Met Pro Ser Thr Gln Thr Ser Lys Pro Pro Gln Leu Ser Gln
1               5                   10                  15

Thr Pro Val Ser Ala Ala Val Val Val Lys Ala Leu Lys Asn Ser Val
            20                  25                  30

Lys Ala Ala Phe Leu Thr Ser Ser Pro Gln Ala Pro Gly Thr Leu Lys
        35                  40                  45

Pro Arg Ala Leu Val Arg Pro Ser Pro Gly Pro Val Gln Glu Asn His
    50                  55                  60

Leu Ser Glu Ala Gln Phe Pro Pro Lys Leu
65                  70


<210> SEQ ID NO 15
<211> LENGTH: 81
<212> TYPE: PRT
<213> ORGANISM: Parvovirus B19

<400> SEQUENCE: 15

Met Asp Ser Tyr Leu Thr Thr Pro Met Pro Tyr His Pro Val Ala Val
1               5                   10                  15

Met Gln Asn Leu Glu Glu Lys Met Gln Tyr Tyr Leu Val Lys Thr Tyr
            20                  25                  30

Thr Ser Leu Gly Lys Leu Ala Tyr Asn Tyr Pro Val Leu Thr Met Leu
        35                  40                  45

Gly Leu Ala Met Ser Tyr Lys Leu Gly Pro Arg Lys Val Leu Leu Thr
    50                  55                  60

Val Leu Gln Gly Phe Met Thr Leu Gly Ile Ala Asn Trp Leu Ser Trp
65                  70                  75                  80

Glu


<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

cgcttgtctt agtggcacgt caac                                              24


<210> SEQ ID NO 17
<211> LENGTH: 5594
<212> TYPE: DNA
<213> ORGANISM: Parvovirus B19

<400> SEQUENCE: 17

ccaaatcaga tgccgccggt cgccgccggt aggcgggact tccggtacaa gatggcggac      60

aattacgtca tttcctgtga cgtcatttcc tgtgacgtca cttccggtgg gcgggacttc     120

cggaattagg gttggctctg ggccagcttg cttggggttg ccttgacact aagacaagcg     180

gcgcgccgct tgtcttagtg gcacgtcaac cccaagcgct ggcccagagc caaccctaat     240

tccggaagtc ccgcccaccg gaagtgacgt cacaggaaat gacgtcacag gaaatgacgt     300

aattgtccgc catcttgtac cggaagtccc gcctaccggc ggcgaccggc ggcatctgat     360

ttggtgtctt cttttaaatt ttagcgggct tttttcccgc cttatgcaaa tgggcagcca     420

ttttaagtgt ttcactataa ttttattggt cagttttgta acggttaaaa tgggcggagc     480

gtaggcgggg actacagtat atatagcacg gcactgccgc agctctttct ttctgggctg     540

ctttttcctg gactttcttg ctgttttttg tgagctaact aacaggtatt tatactactt     600
```

-continued

```
gttaacatac taacatggag ctatttagag gggtgcttca agtttcttct aatgttctgg    660
actgtgctaa cgataactgg tggtgctctt tactggattt agacacttct gactgggaac    720
cactaactca tactaacaga ctaatggcaa tatacttaag cagtgtggct tctaagcttg    780
actttaccgg ggggccacta gcggggtgct tgtacttttt tcaagtagaa tgtaacaaat    840
ttgaagaagg ctatcatatt catgtggtta ttggggggcc agggttaaac cccagaaacc    900
tcacagtgtg tgtagagggg ttatttaata atgtacttta tcaccttgta actgaaaatg    960
taaagctaaa atttttgcca ggaatgacta caaaaggcaa atactttaga gatggagagc   1020
agtttataga aaactattta atgaaaaaaa tacctttaaa tgttgtatgg tgtgttacta   1080
atattgatgg atatatagat acctgtattt ctgctacttt tagaagggga gcttgccatg   1140
ccaagaaacc ccgcattacc acagccataa atgacactag tagtgatgct ggggagtcta   1200
gcggcacagg ggcagaggtt gtgccaatta atgggaaggg aactaaggct agcataaagt   1260
ttcaaactat ggtaaactgg ttgtgtgaaa acagagtgtt tacagaggat aagtggaaac   1320
tagttgactt taaccagtac actttactaa gcagtagtca cagtggaagt tttcaaattc   1380
aaagtgcact aaaactagca atttataaag caactaattt agtgcctaca agcacatttc   1440
tattgcatac agactttgag caggttatgt gtattaaaga caataaaatt gttaaattgt   1500
tactttgtca aaactatgac cccctattag tggggcagca tgtgttaaag tggattgata   1560
aaaaatgtgg caagaaaaat acactgtggt tttatgggcc gccaagtaca ggaaaaacaa   1620
acttggcaat ggccattgct aaaagtgttc cagtatatgg catggttaac tggaataatg   1680
aaaactttcc atttaatgat gtagcaggga aaagcttggt ggtctgggat gaaggtatta   1740
ttaagtctac aattgtagaa gctgcaaaag ccattttagg cgggcaaccc accagggtag   1800
atcaaaaaat gcgtggaagt gtagctgtgc ctggagtacc tgtggttata accagcaatg   1860
gtgacattac ttttgttgta agcgggaaca ctacaacaac tgtacatgct aaagccttaa   1920
aagagcgaat ggtaaagtta aactttactg taagatgcag ccctgacatg ggggttactaa  1980
cagaggctga tgtacaacag tggcttacat ggtgtaatgc acaaagctgg gaccactatg   2040
aaaactgggc aataaactac acttttgatt tccctggaat taatgcagat gccctccacc   2100
cagacctcca aaccaccccca attgtcacag acaccagtat cagcagcagt ggtggtgaaa  2160
gctctgaaga actcagtgaa agcagctttt ttaacctcat caccccaggc gcctggaaca   2220
ctgaaacccc gcgctctagt acgcccatcc ccgggaccag ttcaggagaa tcatttgtcg   2280
gaagctcagt ttcctccgaa gttgtagctg catcgtggga agaagccttc tacacacctt   2340
tggcagacca gtttcgtgaa ctgttagttg gggttgatta tgtgtgggac ggtgtaaggg   2400
gtttacctgt gtgttgtgtg caacatatta acaatagtgg gggaggcttg ggactttgtc   2460
cccattgcat taatgtaggg gcttggtata atggatggaa atttcgagaa tttaccccag   2520
atttggtgcg gtgtagctgc catgtgggag cttctaatcc cttttctgtg ctaacctgca   2580
aaaaatgtgc ttacctgtct ggattgcaaa gctttgtaga ttatgagtaa agaaagtggc   2640
aaatggtggg aaagtgatga taaatttgct aaagctgtgt atcagcaatt tgtggaattt   2700
tatgaaaagg ttactggaac agacttagag cttattcaaa tattaaaaga tcactataat   2760
atttctttag ataatcccct agaaaaccca tcctctctgt ttgacttagt tgctcgtatt   2820
aaaaataacc ttaaaaactc tccagactta tatagtcatc attttcaaag tcatggacag   2880
ttatctgacc acccccatgc cttatcatcc agtagcagtc atgcagaacc tagaggagaa   2940
aatgcagtat tatctagtga agacttacac aagcctgggc aagttagcgt acaactaccc   3000
```

-continued

```
ggtactaact atgttgggcc tggcaatgag ctacaagctg ggcccccgca aagtgctgtt   3060
gacagtgctg caaggattca tgactttagg tatagccaac tggctaagtt gggaataaat   3120
ccatatactc attggactgt agcagatgaa gagcttttaa aaaatataaa aaatgaaact   3180
gggtttcaag cacaagtagt aaaagactac tttactttaa aaggtgcagc tgcccctgtg   3240
gcccattttc aaggaagttt gccggaagtt cccgcttaca acgcctcaga aaaataccca   3300
agcatgactt cagttaattc tgcagaagcc agcactggtg caggaggggg tggcagtaat   3360
cctgtcaaaa gcatgtggag tgagggggcc acttttagtg ccaactctgt aacttgtaca   3420
ttttccagac agtttttaat tccttatgac ccagagcacc attataaggt gttttctccc   3480
gcagcaagca gctgccacaa tgccagtgga aaggaggcaa aggtttgcac aattagtccc   3540
ataatgggat actcaacccc atggagatat ttagatttta atgctttaaa tttatttttt   3600
tcacctttag agtttcagca cttaattgaa aattatggaa gtatagctcc tgatgcttta   3660
actgtaacca tatcagaaat tgctgttaag gatgttacag acaaaactgg agggggggta   3720
caggttactg acagcactac agggcgccta tccatgttag tagaccatga atacaagtac   3780
ccatatgtgt taggacaagg tcaggatact ttagccccag aacttcctat ttgggtatac   3840
tttcccccctc aatatgctta cttaacagta ggagatgtta acacacaagg aatctctgga   3900
gacagcaaaa aattagcaag tgaagaatca gcattttatg ttttggaaca cagttctttt   3960
cagcttttag gtacaggagg tacagcaact atgtcttata agtttcctcc agtgccccca   4020
gaaaatttag agggctgcag tcaacacttt tatgaaatgt acaatccctt atacggatcc   4080
cgcttagggg ttcctgacac attaggaggt gacccaaaat ttagatcttt aacacatgaa   4140
gaccatgcaa ttcagcccca aaacttcatg ccagggccac tagtaaactc agtgtctaca   4200
aaggagggag acagctctaa tactggagct ggaaaagcct taacaggcct tagcacaggc   4260
acctctcaaa acactagaat atccttacgc cctgggccag tgtcacagcc ataccaccac   4320
tgggacacag ataaatatgt tccaggaata aatgccattt ctcatggtca gaccacttat   4380
ggtaacgctg aagacaaaga gtatcagcaa ggagtgggta gatttccaaa tgaaaaagaa   4440
cagctaaaac agttacaggg tttaaacatg cacacctatt tccccaataa aggaacccag   4500
caatatacag atcaaattga gcgcccccta atggtgggtt ctgtatggaa cagaagagcc   4560
cttcactatg aaagccagct gtggagtaaa attccaaatt tagatgacag ttttaaaact   4620
cagtttgcag ccttaggagg atggggtttg catcagccac ctcctcaaat atttttaaaa   4680
atattaccac aaagtgggcc aattggaggt attaaatcaa tgggaattac taccttagtt   4740
cagtatgccg tgggaattat gacagtaact atgacattta aattggggcc ccgtaaagct   4800
acgggacggt ggaatcctca acctggagta tatcccccgc acgcagcagg tcatttacca   4860
tatgtactat atgaccccac agctacagat gcaaaacaac accacaggca tggatacgaa   4920
aagcctgaag aattgtggac agccaaaagc cgtgtgcacc cattgtaaac actccccacc   4980
gtgccctcag ccaggatgcg taactaaacg cccaccagta ccacccagac tgtacctgcc   5040
ccctcctgta cctataagac agcctaacac aaaagatata gacaatgtag aatttaagta   5100
cttaaccaga tatgaacaac atgttattag aatgttaaga ttgtgtaata tgtatcaaaa   5160
tttagaaaaa taaacatttg ttgtggttaa aaaattatgt tgttgcgctt taaaaattta   5220
aaagaagaca ccaaatcaga tgccgccggt cgccgccggt aggcgggact tccggtacaa   5280
gatggcggac aattacgtca tttcctgtga cgtcatttcc tgtgacgtca cttccggtgg   5340
gcgggacttc cggaattagg gttggctctg ggccagcgct tggggttgac gtgccactaa   5400
```

gacaagcggc gcgccgcttg tcttagtgtc aaggcaaccc caagcaagct ggcccagagc 5460
caaccctaat tccggaagtc ccgcccaccg gaagtgacgt cacaggaaat gacgtcacag 5520
gaaatgacgt aattgtccgc catcttgtac cggaagtccc gcctaccggc ggcgaccggc 5580
ggcatctgat ttgg 5594

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ccacgatgca gctacaactt 20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gtgagcgcgc cgcttgtctt agtg 24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gtgagcgcgc cgcttgatct tagt 24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
aacttccact gtgactactg 20

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gtgagcgcgc cgcttgatct tagt 24

<210> SEQ ID NO 23
<211> LENGTH: 20
<212> TYPE: DNA
<213> ORGANISM: Artificial Sequence
<220> FEATURE:

<223> OTHER INFORMATION: Description of Artificial Sequence: Synthetic primer

<400> SEQUENCE: 23
aacaccacag gcatggatac 20

<210> SEQ ID NO 24
<211> LENGTH: 5112
<212> TYPE: DNA
<213> ORGANISM: Parvovirus B19

<400> SEQUENCE: 24
gaattccgcc aaatcagatg ccgccggtcg ccgccggtag gcgggacttc cggtacaaga 60
tggcggacaa ttacgtcatt tcctgtgacg tcatttcctg tgacgtcaca ggaaatgacg 120
taattgtccg ccatcttgta ccggaagtcc cgcctaccgg cggcgaccgg cggcatctga 180
tttggtgtct tcttttaaat tttagcgggc ttttttcccg ccttatgcaa atgggcagcc 240 atttaagtg ttttactata attttattgg ttagttttgt aacggttaaa atgggcggag 300
cgtaggcggg gactacagta tatatagcac ggtactgccg cagctctttc tttctgggct 360
gctttttcct ggactttctt gctgtttttt gtgagctaac taacaggtat ttatactact 420
tgttaacatc ctaacatgga gctatttaga ggggtgcttc aagtttcttc taatgttcta 480
gactgtgcta acgataactg gtggtgctct ttactggatt tagacacttc tgactgggaa 540
ccactaactc atactaacag actaatggca atatacttaa gcagtgtggc ttctaagctt 600
gactttaccg gggggccact agcagggtgc ttgtactttt ttcaagtaga atgtaacaaa 660
tttgaagaag gctatcatat tcatgtggtt actgggggc cagggttaaa ccccagaaac 720
cttacagtgt gtgtagaggg gttatttaat aatgtacttt atcaccttgt aactgaaaat 780
gtgaagctaa aatttttgcc aggaatgact acaaaaggca aatactttag agatggagag 840
cagtttatag aaaactattt aatgaaaaaa atacctttaa atgttgtatg gtgtgttact 900
aatattgatg gatatataga tacctgtatt tctgctactt ttagaagggg agcttgccat 960
gccaagaaac cccgcattac cacagccata aatgatacta gtagtgatgc tggggagtct 1020
agcggcacag gggcagaggt tgtgccattt aatgggaagg gaactaaggc tagcataaag 1080
tttcaaacta tggtaaactg gttgtgtgaa aacagagtgt ttacagagga taagtggaaa 1140
ctagttgact ttaaccagta cactttacta agcagtagtc acagtggaag ttttcaaatt 1200
caaagtgcac taaaactagc aatttataaa gcaactaatt tagtgcctac tagcacattt 1260
ttattgcata cagactttga gcaggttatg tgtattaaag acaataaaat tgttaaattg 1320
ttactttgtc aaaactatga ccccctattg gtggggcagc atgtgttaaa gtggattgat 1380
aaaaaatgtg gtaagaaaaa tacactgtgg ttttatgggc cgccaagtac aggaaaaaca 1440
aacttggcaa tggccattgc taaaagtgtt ccagtatatg gcatggttaa ctggaataat 1500
gaaaactttc catttaatga tgtagcagga aaaagcttgg tggtctggga tgaaggtatt 1560
attaagtcta caattgtaga agctgcaaaa gccattttag gcgggcaacc caccagggta 1620
gatcaaaaaa tgcgtggaag tgtagctgtg cctggagtac ctgtggttat aaccagcaat 1680
ggtgacatta cttttgttgt aagcgggaac actacaacaa ctgtacatgc taaagcctta 1740
aaagagcgca tggtaaagtt aaactttact gtaagatgca gccctgacat ggggttacta 1800
acagaggctg atgtacaaca gtggcttaca tggtgtaatg cacaaagctg ggaccactat 1860
gaaaactggg caataaacta cacttttgat ttccctggaa ttaatgcaga tgccctccac 1920
ccagacctcc aaaccacccc aattgtcaca gacaccagta tcagcagcag tggtggtgaa 1980

-continued

```
agctctgaag aactcagtga aagcagcttt tttaacctca tcaccccagg cgcctggaac   2040
actgaaaccc cgcgctctag tacgcccatc cccgggacca gttcaggaga atcatttgtc   2100
ggaagcccag tttcctccga agttgtagct gcatcgtggg aagaagcctt ctacacacct   2160
ttggcagacc agtttcgtga actgttagtt ggggttgatt atgtgtggga cggtgtaagg   2220
ggtttacctg tgtgttgtgt gcaacatatt aacaatagtg gggagagggtt gggactttgt  2280
ccccattgca ttaatgtagg ggcttggtat aatggatgga aatttcgaga atttacccca   2340
gatttggtgc gatgtagctg ccatgtggga gcttctaatc ccttttctgt gctaacctgc   2400
aaaaaatgtg cttacctgtc tggattgcaa agctttgtag attatgagta aaaaaagtgg   2460
caaatggtgg gaaagtgatg ataaatttgc taaagctgtg tatcagcaat ttgtggaatt   2520
ttatgaaaag gttactggaa cagacttaga gcttattcaa atattaaaag atcattataa   2580
tatttcttta gataatcccc tagaaaaccc atcctctctg tttgacttag ttgctcgtat   2640
taaaaataac cttaaaaact ctccagactt atatagtcat cattttcaaa gtcatggaca   2700
gttatctgac cacccccatg ccttatcatc cagtagcagt catgcagaac ctagaggaga   2760
aaatgcagta ttatctagtg aagacttaca caagcctggg caagttagcg tacaactacc   2820
cggtactaac tatgttgggc ctggcaatga gctacaagct gggcccccgc aaagtgctgt   2880
tgacagtgct gcaaggattc atgactttag gtatagccaa ctggctaagt tgggaataaa   2940
tccatatact cattggactg tagcagatga agagctttta aaaaatataa aaaatgaaac   3000
tgggtttcaa gcacaagtag taaaagacta ctttacttta aaaggtgcag ctgcccctgt   3060
ggcccatttt caaggaagtt tgccggaagt tcccgcttac aacgcctcag aaaaataccc   3120
aagcatgact tcagttaatt ctgcagaagc cagcactggt gcaggagggg ggggcagtaa   3180
ttctgtcaaa agcatgtgga gtgagggggc cacttttagt gctaactctg taacttgtac   3240
attttccaga cagtttttaa ttccatatga cccagagcac cattataagg tgttttctcc   3300
cgcagcgagt agctgccaca atgccagtgg aaaggaggca aaggtttgca ccatcagtcc   3360
cataatggga tactcaaccc catggagata tttagatttt aatgctttaa atttattttt   3420
ttcaccttta gagtttcagc acttaattga aaattatgga agtatagctc ctgatgcttt   3480
aactgtaacc atatcagaaa ttgctgttaa ggatgttaca gacaaaactg gagggggggt   3540
acaggttact gacagcacta cagggcgcct atgcatgtta gtagaccatg aatacaagta   3600
cccatatgtg ttagggcaag gtcaggatac tttagcccca gaacttccta tttgggtata   3660
ctttcccccct caatatgctt acttaacagt aggagatgtt aacacacaag gaatttctgg  3720
agacagcaaa aaattagcaa gtgaagaatc agcattttat gttttggaac acagttcttt   3780
tcagctttta ggtacaggag gtacagcatc tatgtcttat aagtttcctc cagtgccccc   3840
agaaaattta gagggctgca gtcaacactt ttatgaaatg tacaatccct tatacggatc   3900
ccgcttaggg gttcctgaca cattaggagg tgacccaaaa tttagatctt taacacatga   3960
agaccatgca attcagcccc aaaacttcat gccagggcca ctagtaaact cagtgtctac   4020
aaaggaggga gacagctcta atactggagc tggaaaagcc ttaacaggcc ttagcacagg   4080
tacctctcaa aacactagaa tatccttacg ccctgggcca gtgtctcagc cataccacca   4140
ctgggacaca gataaatatg tcacaggaat aaatgccatt tctcatggtc agaccactta   4200
tggtaacgct gaagacaaag agtatcagca aggagtgggt agatttccaa atgaaaaaga   4260
acagctaaaa cagttacagg gtttaaacat gcacacctac tttcccaata aaggaaccca   4320
gcaatataca gatcaaattg agcgccccct aatggtgggt tctgtatgga acagaagagc   4380
```

```
ccttcactat gaaagccagc tgtggagtaa aattccaaat ttagatgaca gttttaaaac   4440
tcagtttgca gccttaggag gatggggttt gcatcagcca cctcctcaaa tatttttaaa   4500
aatattacca caaagtgggc caattggagg tattaaatca atgggaatta ctaccttagt   4560
tcagtatgcc gtgggaatta tgacagtaac tatgacattt aaattggggc cccgtaaagc   4620
tacgggacgg tggaatcctc aacctggagt atatcccccg cacgcagcag gtcatttacc   4680
atatgtacta tatgacccca cagctacaga tgcaaaacaa caccacagac atggatatga   4740
aaagcctgaa gaattgtgga cagccaaaag ccgtgtgcac ccattgtaaa cactccccac   4800
cgtgccctca gccaggatgc gtaactaaac gcccaccagt accacccaga ctgtacctgc   4860
cccctcctgt acctataaga cagcctaaca caaaagatat agacaatgta gaatttaagt   4920
acttaaccag atatgaacaa catgttatta gaatgttaag attgtgtaat atgtatcaaa   4980
atttagaaaa ataaacattt gttgtggtta aaaaattatg ttgttgcgct ttaaaaattt   5040
aaaagaagac accaaatcag atgccgccgg tcggccggta ggcgggactt ccggtacaag   5100
atggcggaat tc                                                        5112
```

<210> SEQ ID NO 25
<211> LENGTH: 5596
<212> TYPE: DNA
<213> ORGANISM: Parvovirus B19

<400> SEQUENCE: 25

```
ccaaatcaga tgccgccggt cgccgccggt aggcgggact tccggtacaa gatggcggac     60
aattacgtca tttcctgtga cgtcatttcc tgtgacgtca cttccggtgg gcgggacttc    120
cggaattagg gttggctctg ggccagcttg cttggggttg ccttgacact aagacaagcg    180
gcgcgccgct tgatcttagt ggcacgtcaa ccccaagcgc tggcccagag ccaaccctaa    240
ttccggaagt cccgcccacc ggaagtgacg tcacaggaaa tgacgtcaca ggaaatgacg    300
taattgtccg ccatcttgta ccggaagtcc cgcctaccgg cggcgaccgg cggcatctga    360
tttggtgtct tcttttaaat tttagcgggc ttttttcccg ccttatgcaa atgggcagcc    420
attttaagtg ttttactata attttattgg tcagttttgt aacggttaaa atgggcggag    480
cgtaggcggg gactacagta tatatagcac agcactgccg cagctctttc tttctgggct    540
gctttttcct ggactttctt gctgtttttt gtgagctaac taacaggtat ttatactact    600
tgttaatata ctaacatgga gctatttaga ggggtgcttc aagtttcttc taatgttctg    660
gactgtgcta acgataactg gtggtgctct ttactagatt tagacacttc tgactgggaa    720
ccactaactc atactaacag actaatggca atatacttaa gcagtgtggc ttctaagctt    780
gaccttaccg gggggccact agcagggtgc ttgtactttt ttcaagcaga atgtaacaaa    840
tttgaagaag gctatcatat tcatgtggtt attgggggc cagggttaaa ccccagaaac    900
ctcacagtgt gtgtagaggg gttatttaat aatgtacttt atcactttgt aactgaaaat    960
gtgaagctaa aatttttgcc aggaatgact acaaaaggca aatactttag agatggagag   1020
cagtttatag aaaactattt aatgaaaaaa atacctttaa atgttgtatg gtgtgttact   1080
aatattgatg gatatataga tacctgtatt tctgctactt ttagaagggg agcttgccat   1140
gccaagaaac cccgcattac cacagccata aatgatacta gtagcgatgc tggggagtct   1200
agcggcacag gggcagaggt tgtgccattt aatgggaagg gaactaaggc tagcataaag   1260
tttcaaacta tggtaaactg gttgtgtgaa aacagagtgt ttacagagga taagtggaaa   1320
ctagttgact ttaaccagta cactttacta agcagtagtc acagtggaag ttttcaaatt   1380
```

-continued

```
caaagtgcac taaaactagc aatttataaa gcaactaatt tagtgcctac tagcacattt   1440
ttattgcata cagactttga gcaggttatg tgtattaaag acaataaaat tgttaaattg   1500
ttactttgtc aaaactatga cccccctattg gtggggcagc atgtgttaaa gtggattgat   1560
aaaaaatgtg gcaagaaaaa tacactgtgg ttttatgggc cgccaagtac aggaaaaaca   1620
aacttggcaa tggccattgc taaaagtgtt ccagtatatg gcatggttaa ctggaataat   1680
gaaaactttc catttaatga tgtagcagga aaaagcttgg tggtctggga tgaaggtatt   1740
attaagtcta caattgtaga agctgcaaaa gccattttag gcgggcaacc caccagggta   1800
gatcaaaaaa tgcgtggaag tgtagctgtg cctggagtac ctgtggttat aaccagcaat   1860
ggtgacatta cttttgttgt aagcgggaac actacaacaa ctgtacatgc taaagcctta   1920
aaagagcgca tggtaaagtt aaactttact gtaagatgca gccctgacat ggggttacta   1980
acagaggctg atgtacaaca gtggcttaca tggtgtaatg cacaaagctg ggaccactat   2040
gaaaactggg caataaacta cacttttgat ttccctggaa ttaatgcaga tgccctccac   2100
ccagacctcc aaaccacccc aattgtcaca gacaccagta tcagcagcag tggtggtgaa   2160
agctctgaag aactcagtga aagcagcttt tttaacctca tcaccccagg cgcctggaac   2220
actgaaaccc cgcgctctag tacgcccatc cccgggacca gttcaggaga atcatttgtc   2280
ggaagcccag tttcctccga agttgtagct gcatcgtggg aagaagcctt ctacacacct   2340
ttggcagacc agtttcgtga actgttagtt ggggttgatt atgtgtggga cggtgtaagg   2400
ggtttacctg tgtgttgtgt gcaacatatt aacaatagtg gggaggctt gggactttgt   2460
ccccattgca ttaatgtagg ggcttggtat aatggatgga aatttcgaga atttacccca   2520
gatttggtgc gatgtagctg ccatgtggga gcttctaatc ccttttctgt gctaacctgc   2580
aaaaaatgtg cttacctgtc tggattgcaa agctttgtag attatgagta aagaaagtgg   2640
caaatggtgg gaaagtgatg atgaatttgc taaagctgtg tatcagcaat ttgtggaatt   2700
ttatgaaaag gttactggaa cagacttaga gcttattcaa atattaaaag atcattataa   2760
tatttcttta gataatcccc tagaaaaccc atcctctctg tttgacttag ttgctcgcat   2820
taaaaataac cttaaaaatt ctccagactt atatagtcat cattttcaaa gtcatggaca   2880
gttatctgac caccccccatg ccttatcatc cagtagcagt catgcagaac ctagaggaga   2940
agatgcagta ttatctagtg aagacttaca caagcctggg caagttagcg tacaactacc   3000
cggtactaac tatgttgggc ctggcaatga gctacaagct gggcccccgc aaagtgctgt   3060
tgacagtgct gcaaggattc atgactttag gtatagccaa ctggctaagt tgggaataaa   3120
tccatatact cattggactg tagcagatga agagctttta aaaaatataa aaaatgaaac   3180
tgggtttcaa gcacaagtag taaaagacta ctttacttta aaaggtgcag ctgcccctgt   3240
ggcccatttt caaggaagtt tgccggaagt tcccgcttac aacgcctcag aaaaataccc   3300
aagcatgact tcagttaatt ctgcagaagc cagcactggt gcaggagggg ggggcagtaa   3360
tcctgtcaaa agcatgtgga gtgagggggc cacttttagt gccaactctg tgacttgtac   3420
attttctaga cagtttttaa ttccatatga cccagagcac cattataagg tgttttctcc   3480
cgcagcaagt agctgccaca atgccagtgg aaaggaggca aaggtttgca ccattagtcc   3540
cataatggga tactcaaccc catggagata tttagatttt aatgctttaa acttattttt   3600
ttcaccttta gagtttcagc acttaattga aaattatgga agtatagctc ctgatgcttt   3660
aactgtaacc atatcagaaa ttgctgttaa ggatgttaca gacaaaactg gagggggggt   3720
gcaggttact gacagcacta cagggcgcct atgcatgtta gtagaccatg aatacaagta   3780
```

-continued

```
cccatatgtg ttagggcaag gtcaagatac tttagcccca gaacttccta tttgggtata   3840

ctttcccccct caatatgctt acttaacagt aggagatgtt aacacacaag gaatttctgg   3900

agacagcaaa aaattagcaa gtgaagaatc agcattttat gttttggaac acagttcttt   3960

tcagctttta ggtacaggag gtacagcaac tatgtcttat aagtttcctc cagtgccccc   4020

agaaaattta gagggctgca gtcaacactt ttatgagatg tacaatccct tatacggatc   4080

ccgcttaggg gttcctgaca cattaggagg tgacccaaaa tttagatctt taacacatga   4140

agaccatgca attcagcccc aaaacttcat gccagggcca ctagtaaact cagtgtctac   4200

aaaggaggga gacagctcta atactggagc tgggaaagcc ttaacaggcc ttagcacagg   4260

tacctctcaa aacactagaa tatccttacg cccggggcca gtgtctcagc cgtaccacca   4320

ctgggacaca gataaatatg tcacaggaat aaatgctatt tctcatggtc agaccactta   4380

tggtaacgct gaagacaaag agtatcagca aggagtgggt agatttccaa atgaaaaaga   4440

acagctaaaa cagttacagg gtttaaacat gcacacctac tttcccaata aaggaaccca   4500

gcaatataca gatcaaattg agcgcccccct aatggtgggt tctgtatgga acagaagagc   4560

ccttcactat gaaagccagc tgtggagtaa aattccaaat ttagatgaca gttttaaaac   4620

tcagtttgca gccttaggag gatggggttt gcatcagcca cctcctcaaa tatttttaaa   4680

aatattacca caaagtgggc caattggagg tattaaatca atgggaatta ctaccttagt   4740

tcagtatgcc gtgggaatta tgacagtaac catgacattt aaattggggc cccgtaaagc   4800

tacgggacgg tggaatcctc aacctggagt atatcccccg cacgcagcag gtcatttacc   4860

atatgtacta tatgacccta cagctacaga tgcaaaacaa caccacagac atggatatga   4920

aaagcctgaa gaattgtgga cagccaaaag ccgtgtgcac ccattgtaaa cactccccac   4980

cgtgccctca gccaggatgc gtaactaaac gcccaccagt accacccaga ctgtacctgc   5040

cccctcctat acctataaga cagcctaaca caaaagatat agacaatgta gaatttaagt   5100

atttaaccag atatgaacaa catgttatta gaatgttaag attgtgtaat atgtatcaaa   5160

atttagaaaa ataaacgttt gttgtggtta aaaaattatg ttgttgcgct ttaaaaattt   5220

aaaagaagac accaaatcag atgccgccgg tcgccgccgg taggcgggac ttccggtaca   5280

agatggcgga caattacgtc atttcctgtg acgtcatttc ctgtgacgtc acttccggtg   5340

ggcggaactt ccggaattag ggttggctct gggccagcgc ttggggttga cgtgccacta   5400

agatcaagcg gcgcgccgct tgtcttagtg tcaaggcaac cccaagcaag ctggcccaga   5460

gccaacccta attccggaag tcccgcccac cggaagtgac gtcacaggaa atgacgtcac   5520

aggaaatgac gtaattgtcc gccatcttgt accggaagtc ccgcctaccg gcggcgaccg   5580

gcggcatctg atttgg                                                   5596
```

<210> SEQ ID NO 26
<211> LENGTH: 5255
<212> TYPE: DNA
<213> ORGANISM: Parvovirus B19

<400> SEQUENCE: 26

```
cgccaaatca gatgccgccg gtcgccgccg gtaggcggga cttccggtac aagatggcgg     60

acaattacgt catttcctgt gacgtcacag gaaatgacgt cacaggaaat gacgtaattg    120

tccgccatct tgtaccggaa gtcccgccta ccggcggcga ccggcggcat ctgatttggt    180

gtcttctttt aaattttagc gggctttttt cccgccttat gcaaatgggc agccatttta    240

agtgttttac tataatttta ttggtcagtt ttgtaacggt taaaatgggc ggagcgtagg    300
```

-continued

```
cggggactac agtatatata gcagggcact gccgcagctc tttctttctg ggctgctttt    360
tcctggactt tcttgctgtt ttttgtgagc taactaacag gtatttatac tacttgttaa    420
catactaaca tggagctatt tagaggggtg cttcaagttt cttctaatgt tctggactgt    480
gctaacgata actggtggtg ctctttactg gatttagaca cttctgactg ggaaccacta    540
actcatacta acagactaat ggcaatatac ttaagcagtg tggcttctaa gcttgacttt    600
accgggggc cactagcagg gtgcttgtac ttttttcaag tagaatgtaa caaatttgaa    660
gaaggctatc atattcatgt ggttattggg gggccagggt taaaccccag aaacctcaca    720
gtgtgtgtag aggggttatt taataatgta ctttatcacc ttgtaactga aaatgtgaag    780
ctaaaatttt tgccaggaat gactacaaaa ggcaaatact ttagagatgg agagcagttt    840
atagaaaact atttaatgaa aaaaatacct ttaaatgttg tatggtgtgt tactaatatt    900
gatggatata tagatacctg tatttctgct acttttagaa ggggagcttg ccatgccaag    960
aaaccccgca ttaccacagc cataaatgat gctagtagtg atccgggga gtctagcggc   1020
acaggggcag aggttgtgcc atttaatggg aagggaacta aggctagcat aaagtttcaa   1080
actatggtaa actggttgtg tgaaaacaga gtgtttacag aggataagtg gaaactagtt   1140
gactttaacc agtacacttt actaagcagt agtcacagtg gaagttttca aattcagagt   1200
gcactaaaac tagcaattta taaagcaact aatttagtgc ctactagcac atttttattg   1260
catacagact ttgagcagat tatgtgtatt aaagacaata aaattgttaa attgttactt   1320
tgtcaaaact atgacccct attggtgggg cagcatgtgt taaagtggat tgataaaaaa   1380
tgtggcaaga aaaatacact gtggttttat gggccgccaa gtacaggaaa aacaaacttg   1440
gcaatggcca ttgctaaaag tgttccagta tatggcatgg ttaactggaa taatgaaaac   1500
tttccattta atgatgtagc agggaaaagc ttggtggtct gggatgaagg tattattaag   1560
tctacaattg tggaagctgc aaaagccatt ttaggcgggc aacccaccag ggtagatcaa   1620
aaaatgcgtg gaagtgtagc tgtgcctgga gtacctgtgg ttataaccag caatggtgac   1680
attacttttg ttgtaagcgg gaacactaca acaactgtac atgctaaagc cttaaaagag   1740
cgaatggtaa agttaaactt tactgtaaga tgcagccctg acatggggtt actaacagag   1800
gctgatgtac aacagtggct tacatggtgt aatgcacaaa gctgggacca ctatgaaaac   1860
tgggcaataa actacacttt tgatttccct ggaattaatg cagatgccct ccacccagac   1920
ctccaaacca ccccaattgt cacagacacc agtatcagca gcagtggtgg tgaaagctct   1980
gaagaactca gtgaaagcag ctttttttaac ctcatcaccc caggcgcctg gaacactgaa   2040
accccgcgct ctagtacgcc catccccggg accagttcag gagaatcatt tgtcggaagc   2100
tcagtttcct ccgaagttgt agctgcatcg tgggaagaag ccttctacac acctttggca   2160
gaccagtttc gtgaactgtt agttggggtt gattatgtgt gggacggtgt aaggggttta   2220
cctgtgtgtt gtgtgcaaca tattaacaat agtgggggag gcttgggact ttgtccccat   2280
tgcattaatg taggggcttg gtataatgga tggaaatttc gagaatttac cccagatttg   2340
gtgcggtgta gctgccatgt gggagcttct aatccctttt ctgtgctaac ctgcaaaaaa   2400
tgtgcttacc tgtctggatt gcaaagcttt gtagattatg agtaaagaaa gtggcaaatg   2460
gtgggaaagt gatgataaat ttgctaaagc tgtgtatcag caatttgtgg aattttatga   2520
gaaggttact ggaacagact tagagcttat tcaaatatta aaagatcatt ataatatttc   2580
tttagatcat cccctagaaa acccatcctc tctgtttaac ttagttgctc gtattaaaaa   2640
taaccttaaa aactctccag acttatatag tcatcatttt caaagtcatg gacagttatc   2700
```

-continued

```
tgaccacccc catgccttat catccagtag cagtcatgca gaacctagag gagaaaatgc   2760
agtattatct agtgaagact tacacaagcc tgggcaagtt agcgtacaac tacccggtac   2820
taactatgtt gggcctggca atgagctaca agctgggccc ccgcaaagtg ctgttgacag   2880
tgctgcaagg attcatgact ttaggtatag ccaactggct aagttgggaa taaatccata   2940
tactcattgg actgtagcag atgaagagct tttaaaaaat ataaaaaatg aaactgggtt   3000
tcaagcacaa gtagtaaaag actactttac tttaaaaggt gcagctgccc ctgtggccca   3060
ttttcaagga agtttgccgg aagttcccgc ttacaacgcc tcagaaaaat acccaagcat   3120
gacttcagtt aattctgcag aagccagcac tggtgcagga gggggtggca gtaatcctgt   3180
caaaagcatg tggagtgagg gggccacttt tagtgccaac tctgtaactt gtacattttc   3240
cagacagttt ttaattccat atgacccaga gcaccattat aaggtgtttt ctcccgcagc   3300
aagtagctgc cacaatgcca gtggaaagga ggcaaaggtt tgcaccatta gtcccataat   3360
gggatactca accccatgga gatatttaga ttttaatgct ttaaatttat ttttttcacc   3420
tttagagttt cagcacttaa ttgaaaatta tggaagtata gctcctgatg ctttaactgt   3480
aaccatatca gaaattgctg ttaaggatgt tacagacaaa actggagggg gggtacaggt   3540
tactgacagc actacagggc gcctatgcat gttagtagac catgaataca agtacccata   3600
tgtgttaggg caaggtcagg atactttagc cccagaactt cctatttggg tatactttcc   3660
ccctcaatat gcttacttaa cagtgggaga tgtcaacaca caaggaatct ctggagacag   3720
caaaaaatta gcaagtgaag aatcagcatt ttatgttttg gaacacagtt cctttcagct   3780
tttaggtaca ggaggtacag caactatgtc ttataagttt cctccagtgc ccccagaaaa   3840
tttagagggc tgcagtcaac acttttatga aatgtacaat cccttatacg gatcccgctt   3900
aggggttcct gacacattag gaggtgaccc aaaatttaga tctttaacac atgaagacca   3960
tgcaattcag ccccaaaact ttatgccagg gccactagta aactcagtgt ctacaaagga   4020
gggagacagc tctaatactg gagctggaaa agccttaaca ggccttagca caggtacctc   4080
tcaaaacact agaatatcct tacgccctgg gccagtgtct cagccatacc accactggga   4140
cacagataaa tatgttacag gaataaatgc catttctcat ggtcaaacca cttatggtaa   4200
cgctgaagac aaagagtatc agcaaggagt gggtagattt ccaaatgaaa aagaacagct   4260
aaaacagtta cagggtttaa acatgcacac ctatttcccc aataaaggaa cccagcaata   4320
tacagatcaa attgagcgcc ccctaatggt gggttctgta tggaacagaa gagcccttca   4380
ctatgaaagc cagctgtgga gtaaaattcc aaatttagat gacagtttta aaactcagtt   4440
tgcagcctta ggaggatggg gtttgcatca gccacctcct caaatatttt taaaaatatt   4500
accacaaagt gggccaattg gaggtattaa atcaatggga attactacct tagttcagta   4560
cgccgtggga attatgacag taactatgac atttaaattg gggccccgta aagctacggg   4620
acggtggaat cctcaacctg gagtatatcc cccgcacgca gcaggtcatt taccatatgt   4680
actatatgac cccacagcta cagatgcaaa acaacaccac agacatggat atgaaaagcc   4740
tgaagaattg tggacagcca aaagccgtgt gcacccattg taaacactcc ccaccgtgcc   4800
ctcagccaag atgcgtaact aaacgcccac cagtaccacc cagactgtac ctgccccctc   4860
ctgtacctat aagacagcct aacacaaaag acatagacaa tgtagaattt aagtacttaa   4920
ccagatatga acaacatgtt attagaatgt taagattgtg taatatgtat caaaatttag   4980
aaaaataaac atttgttgtg gttaaaaaat tatgttgttg cgctttaaaa atttaaaaga   5040
agacaccaaa tcagatgccg ccggtcggcc ggtaggcggg acttccggta caagatggcg   5100
```

gacaattacg tcatttcctg tgacgtcatt tcctgtgacg tcacttccgg tgagcggaac 5160
ttccggaagt gacgtcacag gaaatgacgt cacaggaaat gacgtaattg tccgccatct 5220
tgtaccggaa gtcccgccta ccggccgacc ggcgg 5255

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
catttgtcgg aagctcagtt tcctccgaag 30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cttcggagga aactgagctt ccgacaaatg 30

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gcaaagcttt gtagatttag agtaaagaaa gtggcaaatg gtggg 45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
cccaccattt gccactttct ttactctaaa tctacaaagc tttgc 45

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gatttccctg gaattatagc agatgccctc cacccagacc 40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ggtctgggtg gagggcatct gctataattc cagggaaatc 40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
agtcatcatt ttcaaagtct aggacagtta tctgaccacc 40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ggtggtcaga taactgtcct agactttgaa aatgatgact 40

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
caccacagac atggattaga aaagcctgaa gaattgtgga c 41

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gtccacaatt cttcaggctt ttctaatcca tgtctgtggt g 41

<210> SEQ ID NO 37
<211> LENGTH: 362
<212> TYPE: DNA
<213> ORGANISM: Parvovirus B19

<400> SEQUENCE: 37
ccaaatcaga tgccgccggt cgccgccggt aggcgggact tccggtacaa gatggcggac 60
aattacgtca tttcctgtga cgtcatttcc tgtgacgtca cttccggtgg gcgggacttc 120
cggaattagg gttggctctg ggccagcttg cttggggttg ccttgacact aagacaagcg 180
gcgcgccgct tgtcttagtg gcacgtcaac cccaagcgct ggcccagagc caaccctaat 240
tccggaagtc ccgcccaccg gaagtgacgt cacaggaaat gacgtcacag gaaatgacgt 300
aattgtccgc catcttgtac cggaagtccc gcctaccggc ggcgaccggc ggcatctgat 360
tt 362

<210> SEQ ID NO 38
<211> LENGTH: 5596
<212> TYPE: DNA
<213> ORGANISM: Parvovirus B19

<400> SEQUENCE: 38

```
ccaaatcaga tgccgccggt cgccgccggt aggcgggact tccggtacaa gatggcggac     60

aattacgtca tttcctgtga cgtcatttcc tgtgacgtca cttccggtgg gcgggacttc    120

cggaattagg gttggctctg ggccagcttg cttggggttg ccttgacact aagacaagcg    180

gcgcgccgct tgatcttagt ggcacgtcaa ccccaagcgc tggcccagag ccaaccctaa    240

ttccggaagt cccgcccacc ggaagtgacg tcacaggaaa tgacgtcaca ggaaatgacg    300

taattgtccg ccatcttgta ccggaagtcc cgcctaccgg cggcgaccgg cggcatctga    360

tttggtgtct tcttttaaat tttagcgggc ttttttcccg ccttatgcaa atgggcagcc    420

attttaagtg ttttactata attttattgg tcagttttgt aacggttaaa atgggcggag    480

cgtaggcggg gactacagta tatatagcac agcactgccg cagctctttc tttctgggct    540

gctttttcct ggactttctt gctgtttttt gtgagctaac taacaggtat ttatactact    600

tgttaatata ctaacatgga gctatttaga ggggtgcttc aagtttcttc taatgttctg    660

gactgtgcta acgataactg gtggtgctct ttactagatt tagacacttc tgactgggaa    720

ccactaactc atactaacag actaatggca atatacttaa gcagtgtggc ttctaagctt    780

gaccttaccg gggggccact agcagggtgc ttgtactttt ttcaagcaga atgtaacaaa    840

tttgaagaag gctatcatat tcatgtggtt attgggggggc cagggttaaa ccccagaaac    900

ctcacagtgt gtgtagaggg gttatttaat aatgtacttt atcactttgt aactgaaaat    960

gtgaagctaa aatttttgcc aggaatgact acaaaaggca aatactttag agatggagag   1020

cagtttatag aaaactattt aatgaaaaaa atacctttaa atgttgtatg gtgtgttact   1080

aatattgatg gatatataga tacctgtatt tctgctactt ttagaagggg agcttgccat   1140

gccaagaaac cccgcattac cacagccata aatgatacta gtagcgatgc tggggagtct   1200

agcggcacag gggcagaggt tgtgccattt aatgggaagg gaactaaggc tagcataaag   1260

tttcaaacta tggtaaactg gttgtgtgaa aacagagtgt ttacagagga taagtggaaa   1320

ctagttgact ttaaccagta cactttacta agcagtagtc acagtggaag ttttcaaatt   1380

caaagtgcac taaaactagc aatttataaa gcaactaatt tagtgcctac tagcacattt   1440

ttattgcata cagactttga gcaggttatg tgtattaaag acaataaaat tgttaaattg   1500

ttactttgtc aaaactatga ccccctattg gtggggcagc atgtgttaaa gtggattgat   1560

aaaaaatgtg gcaagaaaaa tacactgtgg ttttatgggc cgccaagtac aggaaaaaca   1620

aacttggcaa tggccattgc taaaagtgtt ccagtatatg gcatggttaa ctggaataat   1680

gaaaactttc catttaatga tgtagcagga aaaagcttgg tggtctggga tgaaggtatt   1740

attaagtcta caattgtaga agctgcaaaa gccattttag gcgggcaacc caccagggta   1800

gatcaaaaaa tgcgtggaag tgtagctgtg cctggagtac ctgtggttat aaccagcaat   1860

ggtgacatta cttttgttgt aagcgggaac actacaacaa ctgtacatgc taaagcctta   1920

aaagagcgca tggtaaagtt aaactttact gtaagatgca gccctgacat ggggttacta   1980

acagaggctg atgtacaaca gtggcttaca tggtgtaatg cacaaagctg ggaccactat   2040

gaaaactggg caataaacta cacttttgat ttccctggaa ttaatgcaga tgccctccac   2100

ccagacctcc aaaccacccc aattgtcaca gacaccagta tcagcagcag tggtggtgaa   2160

agctctgaag aactcagtga aagcagcttt tttaacctca tcaccccagg cgcctggaac   2220
```

-continued

```
actgaaaccc cgcgctctag tacgcccatc cccgggacca gttcaggaga atcatttgtc   2280
ggaagcccag tttcctccga agttgtagct gcatcgtggg aagaagcctt ctacacacct   2340
ttggcagacc agtttcgtga actgttagtt ggggttgatt atgtgtggga cggtgtaagg   2400
ggtttacctg tgtgttgtgt gcaacatatt aacaatagtg ggggaggctt gggactttgt   2460
ccccattgca ttaatgtagg ggcttggtat aatggatgga aatttcgaga atttacccca   2520
gatttggtgc gatgtagctg ccatgtggga gcttctaatc ccttttctgt gctaacctgc   2580
aaaaaatgtg cttacctgtc tggattgcaa agctttgtag attatgagta aagaaagtgg   2640
caaatggtgg gaaagtgatg atgaatttgc taaagctgtg tatcagcaat ttgtggaatt   2700
ttatgaaaag gttactggaa cagacttaga gcttattcaa atattaaaag atcattataa   2760
tatttcttta gataatcccc tagaaaaccc atcctctctg tttgacttag ttgctcgcat   2820
taaaaataac cttaaaaatt ctccagactt atatagtcat cattttcaaa gtcatggaca   2880
gttatctgac cacccccatg ccttatcatc cagtagcagt catgcagaac ctagaggaga   2940
agatgcagta ttatctagtg aagacttaca caagcctggg caagttagcg tacaactacc   3000
cggtactaac tatgttgggc ctggcaatga gctacaagct gggcccccgc aaagtgctgt   3060
tgacagtgct gcaaggattc atgactttag gtatagccaa ctggctaagt tgggaataaa   3120
tccatatact cattggactg tagcagatga agagctttta aaaaatataa aaaatgaaac   3180
tgggtttcaa gcacaagtag taaaagacta ctttacttta aaaggtgcag ctgcccctgt   3240
ggcccatttt caaggaagtt tgccggaagt tcccgcttac aacgcctcag aaaaataccc   3300
aagcatgact tcagttaatt ctgcagaagc cagcactggt gcaggagggg ggggcagtaa   3360
tcctgtcaaa agcatgtgga gtgagggggc cacttttagt gccaactctg tgacttgtac   3420
attttctaga cagtttttaa ttccatatga cccagagcac cattataagg tgttttctcc   3480
cgcagcaagt agctgccaca atgccagtgg aaaggaggca aaggtttgca ccattagtcc   3540
cataatggga tactcaaccc catggagata tttagatttt aatgctttaa acttattttt   3600
ttcaccttta gagtttcagc acttaattga aaattatgga agtatagctc ctgatgcttt   3660
aactgtaacc atatcagaaa ttgctgttaa ggatgttaca gacaaaactg gagggggggt   3720
gcaggttact gacagcacta cagggcgcct atgcatgtta gtagaccatg aatacaagta   3780
cccatatgtg ttagggcaag gtcaagatac tttagcccca gaacttccta tttgggtata   3840
ctttcccccct caatatgctt acttaacagt aggagatgtt aacacacaag gaatttctgg   3900
agacagcaaa aaattagcaa gtgaagaatc agcattttat gttttggaac acagttcttt   3960
tcagctttta ggtacaggag gtacagcaac tatgtcttat aagtttcctc cagtgccccc   4020
agaaaattta gagggctgca gtcaacactt ttatgagatg tacaatccct tatacggatc   4080
ccgcttaggg gttcctgaca cattaggagg tgacccaaaa tttagatctt taacacatga   4140
agaccatgca attcagcccc aaaacttcat gccagggcca ctagtaaact cagtgtctac   4200
aaaggaggga gacagctcta atactggagc tgggaaagcc ttaacaggcc ttagcacagg   4260
tacctctcaa aacactagaa tatccttacg cccggggcca gtgtctcagc cgtaccacca   4320
ctgggacaca gataaatatg tcacaggaat aaatgctatt tctcatggtc agaccactta   4380
tggtaacgct gaagacaaag agtatcagca aggagtgggt agatttccaa atgaaaaaga   4440
```

-continued

```
acagctaaaa cagttacagg gtttaaacat gcacacctac tttcccaata aaggaaccca   4500

gcaatataca gatcaaattg agcgccccct aatggtgggt tctgtatgga acagaagagc   4560

ccttcactat gaaagccagc tgtggagtaa aattccaaat ttagatgaca gttttaaaac   4620

tcagtttgca gccttaggag gatggggttt gcatcagcca cctcctcaaa tatttttaaa   4680

aatattacca caaagtgggc caattggagg tattaaatca atgggaatta ctaccttagt   4740

tcagtatgcc gtgggaatta tgacagtaac catgacattt aaattggggc cccgtaaagc   4800

tacgggacgg tggaatcctc aacctggagt atatcccccg cacgcagcag gtcatttacc   4860

atatgtacta tatgacccta cagctacaga tgcaaaacaa caccacagac atggatatga   4920

aaagcctgaa gaattgtgga cagccaaaag ccgtgtgcac ccattgtaaa cactccccac   4980

cgtgccctca gccaggatgc gtaactaaac gcccaccagt accacccaga ctgtacctgc   5040

cccctcctat acctataaga cagcctaaca caaaagatat agacaatgta gaatttaagt   5100

atttaaccag atatgaacaa catgttatta gaatgttaag attgtgtaat atgtatcaaa   5160

atttagaaaa ataaacgttt gttgtggtta aaaaattatg ttgttgcgct ttaaaaattt   5220

aaaagaagac accaaatcag atgccgccgg tcgccgccgg taggcgggac ttccggtaca   5280

agatggcgga caattacgtc atttcctgtg acgtcatttc ctgtgacgtc acttccggtg   5340

ggcggaactt ccggaattag ggttggctct gggccagcgc ttggggttga cgtgccacta   5400

agatcaagcg gcgcgccgct tgtcttagtg tcaaggcaac cccaagcaag ctggcccaga   5460

gccaacccta attccggaag tcccgcccac cggaagtgac gtcacaggaa atgacgtcac   5520

aggaaatgac gtaattgtcc gccatcttgt accggaagtc ccgcctaccg gcggcgaccg   5580

gcggcatctg atttgg                                                   5596


<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

atcatttgtc ggaagcccag tttcctccga                                      30


<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

atcatttgtc ggaagctcag tttcctccga                                      30
```